United States Patent [19]

Soma et al.

[11] 4,371,644

[45] Feb. 1, 1983

[54] PIPERIDINE DERIVATIVES AND THEIR USE AS POLYMER STABILIZERS

[75] Inventors: Nobuo Soma; Syoji Moromura; Takao Yoshioka; Tomoyuki Kurumada, all of Hiromachi, Japan

[73] Assignee: Sankyo Company Ltd., Tokyo, Japan

[21] Appl. No.: 168,271

[22] Filed: Jul. 10, 1980

Related U.S. Application Data

[62] Division of Ser. No. 866,957, Jan. 5, 1978, abandoned.

[30] Foreign Application Priority Data

Jan. 14, 1977 [JP] Japan .................................. 52-3285

[51] Int. Cl.$^3$ ............................................. C08K 5/34
[52] U.S. Cl. ................................. 524/102; 524/101; 524/103; 524/350
[58] Field of Search ................ 524/101, 102, 103, 350

[56] References Cited

U.S. PATENT DOCUMENTS

| 3,940,363 | 2/1976 | Murayama et al. | 524/102 |
| 3,975,357 | 8/1976 | Murayama et al. | 524/99 |

*Primary Examiner*—John Kight, III
*Assistant Examiner*—R. A. White
*Attorney, Agent, or Firm*—Toren, McGeady and Stanger

[57] ABSTRACT

Piperidine derivatives in which two or three piperidine residues each substituted at the 2- and the 6-position by two methyl groups or by one methyl group and one ethyl group, the piperidine residues being attached by means of substituted alkylene groups, by means of polyoxyalkylene groups (whose oxyalkylene chain is optionally interrupted by one or more phenylene or cyclohexylene groups), by means of substituted isocyanurate groups or by means of glyceryl groups, and acid addition salts thereof are valuable as stabilizers for synthetic polymers.

4 Claims, No Drawings

PIPERIDINE DERIVATIVES AND THEIR USE AS POLYMER STABILIZERS

This is a Division of application Ser. No. 866,957 filed Jan. 5, 1978, now abandoned.

BACKGROUND OF THE INVENTION

This invention relates to certain novel piperidine derivatives and to their use as stabilizers for polymers, particularly synthetic polymers, and provides processes for their preparation. More specifically, it is concerned with compounds having two or three piperidine residues.

Certain classes of piperidine derivatives are known to be useful stabilizers for synthetic polymers. Amongst the known classes of piperidine derivatives are: 4-unsubstituted piperidine derivatives (Japanese Patent Publication No. 46-31733, U.S. Pat. No. 3,975,357 and German Offenlegungsschrift No. 2,621,841); 4-acyloxypiperidine derivatives (U.S. Pat. No. 3,640,928, No. 3,705,166, No. 3,840,494, No. 3,940,363 and No. 3,992,390, British Patent Specifications No. 1,399,239 and No. 1,399,240 and German Offenlegungsschrift No. 2,623,422) 4-ketalpiperidine derivatives (U.S. Patent Specification No. 3,790,525, No. 3,859,293, No. 3,899,464 and No. 3,940,363, British Pat. Specification No. 1,417,835, Japanese Patent Application No. 49-77944, as laid open to public inspection, and German Offenlegungsschrift No. 2,621,855); 4-aminopiperidine derivatives (U.S. Patent Specification No. 3,705,166, No. 3,839,273 and No. 3,904,581, Japanese Patent Application No. 49-60337, as laid open to public inspection, and German Offenlegungsschrift No. 2,621,870); and 1,3,8-triazaspiro[4.5]decane-2,4-dione derivatives (U.S. Patent Specifications No. 3,542,729, No. 3,705,126, No. 3,941,744 and No. 3,975,462, Japanese Patent Application No. 49-72332, as laid open to public inspection and German Offenlegungsschrift No. 2,623,464).

However, these known stabilizers have a number of disadvantages. For example, some of them, in spite of being good light stabilizers, are relatively volatile and are therefore of no practical use in the stabilization of synthetic polymers, since they volatilize at processing temperatures and may also volatilize during prolonged storage of the stabilized articles. Others of these compounds can easily be extracted from synthetic polymers with water or with organic solvents and, again, are of little practical use for the stabilization of synthetic polymers. Some known piperidine derivatives have a single piperidine residue in the molecule and, prior to the present invention, stabilizing compounds containing two or three piperidine residues linked through their 1-positions by a suitable bridging group, e.g. by means of a group derived from 2,2-bis[4-(2-hydroxpropyl)-phenyl]propane, which are structurally quite different from the known piperidine derivatives, have not hitherto been discovered.

BRIEF SUMMARY OF THE INVENTION

It is, therefore, an object of the present invention to provide novel piperidine derivatives useful as stabilizers for polymers, particularly for synthetic polymers, but which do not suffer the disadvantages of the known compounds.

It is a further object of the invention to provide a stabilized composition comprising a polymer, particularly a synthetic polymer, and one of the piperidine derivatives of the invention.

It is a further and more specific object of the invention to provide such a composition in which the stabilizer has superior stabilizing activity against photo- and thermal-deterioration and less volatility and extractability than known piperidine derivatives.

It is a still further object of the invention to provide processes for the preparation of the piperidine derivatives of the invention.

The novel piperidine derivatives of the invention have the general formula (I):

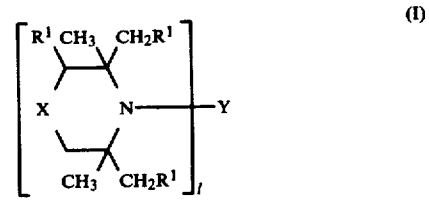

in which:

$R^1$ represents a hydrogen atom or a methyl group;

X represents one of the groups of formulae $-CH_2-$,

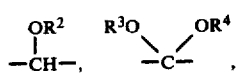

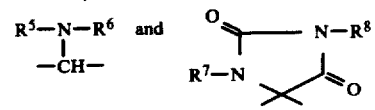

in which:

$R^2$ represents a hydrogen atom, an alkyl group having from 1 to 18 carbon atoms, an allyl group, a benzyl group, an aliphatic, aromatic, araliphatic or alicyclic acyl group having up to 18 carbon atoms (in which the aromatic moiety is unsubstituted or has one or more $C_1-C_4$ alkyl and/or hydroxy substituents), or one of the groups of formulae

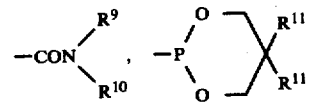

and $-P(OR^{12})_2$;

in which:

$R^9$ represents a hydrogen atom or an alkyl group having from 1 to 4 carbon atoms;

$R^{10}$ represents an alkyl group having from 1 to 18 carbon atoms, a phenyl group which is unsubstituted or has one or more methyl and/or chlorine substituents, a naphthyl group or a cyclohexyl group;

$R^{11}$ represents a hydrogen atom or an alkyl group having from 1 to 4 carbon atoms; and $R^{12}$ represents an alkyl group having from 1 to 4 carbon atoms, a phenyl group or a group of formula

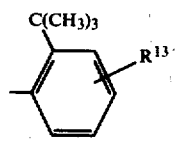

in which $R^{13}$ represents a hydrogen atom or an alkyl group having from 1 to 4 carbon atoms;

$R^3$ and $R^4$ are the same or different and each represents an alkyl group having from 1 to 4 carbon atoms or $R^3$ and $R^4$ together represent a group of formula

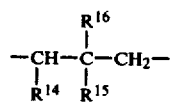

or

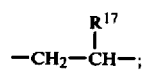

in which:

$R^{14}$ and $R^{15}$ are the same or different and each represents a hydrogen atom or an alkyl group having from 1 to 3 carbon atoms; and $R^{16}$ and $R^{17}$ are the same or different and each represents a hydrogen atom, an alkyl group having from 1 to 3 carbon atoms or a group of formula $-CH_2OR^{18}$ [in which $R^{18}$ represents a hydrogen atom, an alkyl group having from 1 to 4 carbon atoms, an aliphatic, aromatic, araliphatic or alicyclic acyl group having up to 18 carbon atoms (in which the aryl moiety is optionally substituted by one or more $C_1-C_4$ alkyl and/or hydroxy substituents), or a group of formula

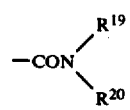

(in which $R^{19}$ has any of the meanings previously defined for $R^9$ and $R^{20}$ has any of the meanings previously defined for $R^{10}$)];

$R^5$ represents an alkyl group having from 1 to 18 carbon atoms, a phenyl group which is unsubstituted or has one or more $C_1-C_4$ alkyl and/or alkoxy substituents, a benzyl group or a cyclohexyl group;

$R^6$ represents an alkyl group having from 1 to 18 carbon atoms, a benzyl group or an aliphatic, aromatic, araliphatic or alicyclic acyl group having up to 18 carbon atoms (in which the aryl moiety is unsubstituted or has one or more $C_1-C_4$ alkyl and/or hydroxy substituents); or $R^5$ and $R^6$ together represent a tetramethylene group, a pentamethylene group or a group of formula $-(CH_2)_2-O-(CH_2)_2-$;

$R^7$ represents a hydrogen atom, an alkyl group having from 1 to 18 carbon atoms, an allyl group, an acetyl group or a benzyl group; and $R^8$ represents an alkyl group having from 1 to 18 carbon atoms, an alkenyl group having 3 or 4 carbon atoms, a benzyl group or one of the groups of formula

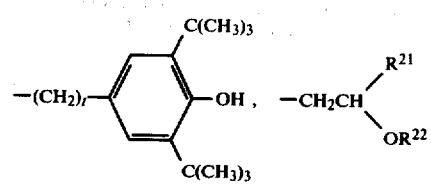

and $-CH_2COOR^{23}$ in which:

t represents 1,2 or 3;

$R^{21}$ represents a hydrogen atom, a methyl group or a phenyl group;

$R^{22}$ represents a hydrogen atom, an alkyl group having from 1 to 8 carbon atoms, an allyl group, a benzyl group or an aliphatic, aromatic, araliphatic or alicyclic acyl group having up to 18 carbon atoms (in which the aryl moiety is unsubstituted or has one or more $C_1-C_4$ alkyl and/or hydroxy substituents); and $R^{23}$ represents an alkyl group having from 1 to 18 carbon atoms, an alkenyl group having 3 or 4 carbon atoms or a phenyl group;

l represents 2 or 3; and when $l=2$:

Y represents one of the groups of formula $-CH_2CH(OZ)CH_2-[OCH_2CH(OZ)CH_2]_2-$, $-CH_2CH(OZ)CH_2-[OCH_2CH(R^{24})]_m-OCH_2CH(OZ)CH_2-$ and $-CH_2CH(OZ)CH_2-[OWO-CH_2CH(OZ)CH_2]_n-$ in which:

m and n each represents an integer of from 1 to 10; $R^{24}$ represents a hydrogen atom or a methyl group; W represents one of the groups of formula

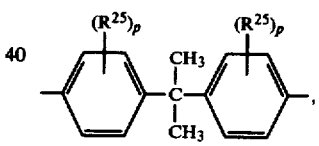

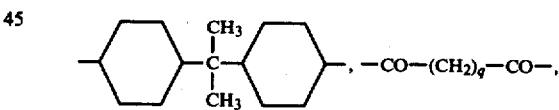

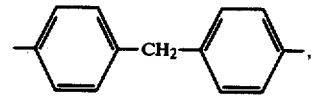

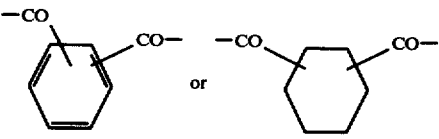

in which:

$R^{25}$ represents a halogen atom:

p represents 0,1 or 2; and q represents an integer of from 1 to 10; and Z has any of the meanings previously defined for $R^2$;

When $l=3$:

Y represents one of the groups of formulae

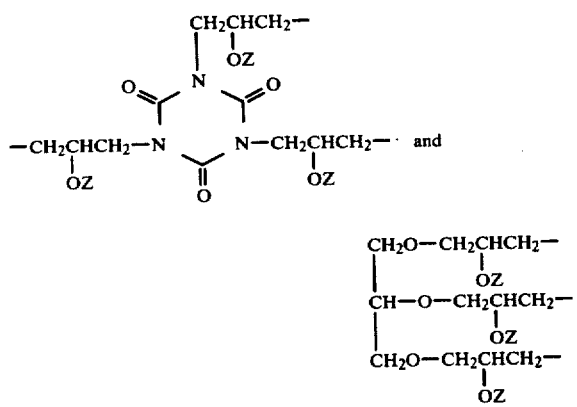

in which Z is as defined above.

DETAILED DESCRIPTION OF INVENTION

In the compounds of formula (I), when $R^2$ and Z represent alkyl groups having from 1 to 18 carbon atoms, they may be, for example, methyl, ethyl, n-propyl, n-butyl, octyl, dodecyl or octadecyl groups, and are preferably alkyl groups having from 1 to 8 carbon atoms, most preferably a methyl group.

When $R^2$ and Z represent aliphatic, aromatic, aralphatic or alicyclic acyl groups having up to 18 carbon atoms, they are preferably groups of formula —$COR^{27}$, in which $R^{27}$ represents: an alkyl group having from 1 to 17 carbon atoms; an alkenyl group having 2 or 3 carbon atoms; a phenyl group, which is optionally substituted by from 1 to 3 $C_1$-$C_4$ alkyl and/or hydroxy substituents, which substituents may be the same or different; a benzyl group; a 4-hydroxy-3,5-di-t-butylphenethyl group; a styryl group; or a cyclohexyl group. Preferred examples of such acyl groups are: acetyl, propionyl, valeryl, octanoyl, 2-ethylhexanoyl, lauroyl, palmitoyl, stearoyl, acryloyl, crotonoyl, methacryloyl, benzoyl, o-toluoyl, m-toluoyl, p-toluoyl, p-t-butylbenzoyl, salicyloyl, 4-hydroxy-3,5-di-t-butylbenzoyl, phenylacetyl, 3-(4-hydroxy-3,5-di-t-butylphenyl)propionyl, cinnamoyl or cyclohexanecarbonyl. We particularly prefer alkanoyl groups having from 2 to 18 carbon atoms, a benzoyl group or a 3-(4-hydroxy-3,5-di-t-butylphenyl)propionyl group, most preferably an acetyl or a benzoyl group.

When $R^2$ and Z represent groups of formula —$CONR^9R^{10}$, $R^9$ may represent a hydrogen atom or an alkyl group having from 1 to 4 carbon atoms (e.g. a methyl, ethyl or n-butyl group), preferably a hydrogen atom, and $R^{10}$ may be an alkyl group having from 1 to 18 carbon atoms (e.g. a methyl, ethyl, n-butyl, octyl or octadecyl group), a phenyl group optionally having one or more methyl and/or chlorine substituents (e.g. phenyl, o-tolyl, m-tolyl, p-tolyl, o-chlorophenyl, m-chlorophenyl or p-chlorophenyl), an α- or β-naphthyl group, or a cyclohexyl group. Of the groups of formula —$CONR^9R^{10}$, we particularly prefer those groups of formula —$CONHR^{10}$, in which $R^{10}$ represents an alkyl group having from 1 to 4 carbon atoms or a phenyl group.

When $R^2$ and Z represent groups of formula

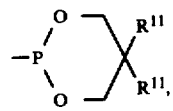

$R^{11}$ may represent a hydrogen atom or an alkyl group having from 1 to 4 carbon atoms, e.g. a methyl, ethyl or n-propyl group, particularly a methyl group.

When $R^2$ and Z represent groups of formula —$P(OR^{12})_2$, $R^{12}$ may represent an alkyl group having from 1 to 4 carbon atoms (e.g. methyl, ethyl or isopropyl), a phenyl group or a group of formula

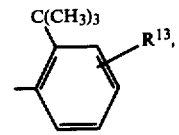

in which $R^{13}$ represents a hydrogen atom or an alkyl group having from 1 to 4 carbon atoms, e.g. methyl, ethyl or t-butyl. Examples of such groups represented by $R^2$ and Z include —$P(OC_2H_5)_2$,

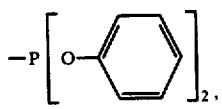

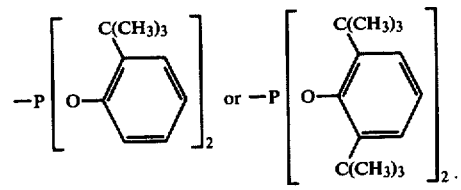

When $R^3$ and $R^4$ represent alkyl groups having from 1 to 4 carbon atoms, they may be, for example, methyl, ethyl or n-butyl groups.

When $R^3$ and $R^4$ together represent one of the groups of formulae

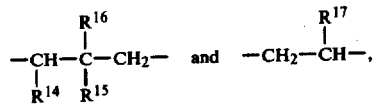

$R^{14}$ and $R^{15}$ may be the same or different and each represents a hydrogen atom or an alkyl group having from 1 to 3 carbon atoms, and $R^{16}$ and $R^{17}$ each represents a hydrogen atom, an alkyl group having from 1 to 3 carbon atoms or a group of formula —$CH_2OR^{18}$. Examples of such groups include: —$(CH_2)_3$—, —$CH(CH_3)$—$CH_2$—$CH_2$—, —$CH_2$—$C(CH_3)_2$—$CH_2$—,

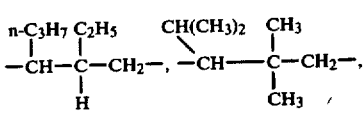

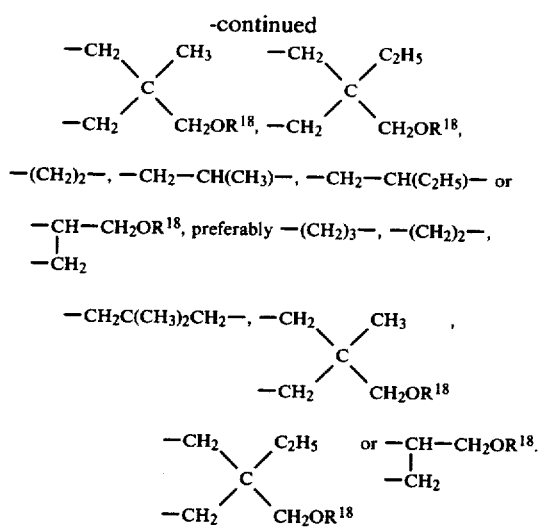

In these formulae, R$^{18}$ represents: a hydrogen atom; an alkyl group having from 1 to 4 carbon atoms, e.g. a methyl, ethyl, n-propyl, n-butyl or isobutyl group; an aliphatic, aromatic, araliphatic or alicyclic acyl group having up to 18 carbon atoms (in which the aromatic moiety is optionally substituted by one or more C$_1$–C$_4$ alkyl and/or hydroxy substituents), preferably any one of the acyl groups previously defined as —COR$^{27}$; or R$^{18}$ may represent a group of formula —CONR$^{19}$R$^{20}$, in which R$^{19}$ is preferably identical to the group represented by R$^9$ and R$^{20}$ is preferably identical to the group represented by R$^{10}$. Of the groups represented by R$^{18}$, we particularly prefer hydrogen atoms, alkanoyl groups having from 2 to 18 carbon atoms or benzoyl groups.

The preferred groups represented jointly by R$^3$ and R$^4$ are the groups of formulae

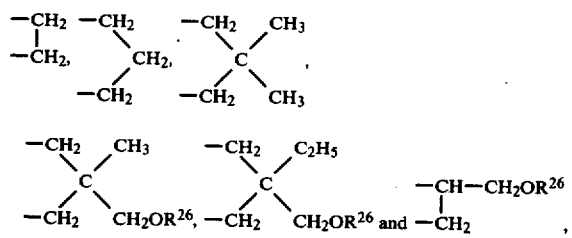

in which R$^{26}$ represents a hydrogen atom, an alkanoyl group having from 2 to 18 carbon atoms or a benzoyl group.

When R$^5$ represents an alkyl group having from 1 to 18 carbon atoms, it may be, for example, a methyl, ethyl, n-butyl, octyl, dodecyl or octadecyl group, and it is preferably a group having from 1 to 8, and more preferably from 1 to 4 carbon atoms.

When R$^5$ represents a phenyl group, it may optionally be substituted by one or more C$_1$–C$_4$ alkyl or C$_1$–C$_4$ alkoxy groups; examples of such groups include phenyl, o-tolyl, m-tolyl, p-tolyl, o-methoxyphenyl, m-methoxyphenyl, p-methoxyphenyl and p-butoxyphenyl.

When R$^6$ represents an alkyl group having from 1 to 18 carbon atoms, it may be any one of the alkyl groups exemplified for R$^5$ and the preferred and most preferred alkyl groups represented by R$^6$ are the same as the preferred and most preferred alkyl groups represented by R$^5$.

When R$^6$ represents an aliphatic, aromatic, araliphatic or alicyclic acyl group having up to 18 carbon atoms, the aryl moiety may optionally be substituted by one or more C$_1$–C$_4$ alkyl and/or hydroxy substituents. Preferred examples of such acyl groups are those given for the group of formula —COR$^{27}$.

When R$^7$ represents an alkyl group having from 1 to 18 carbon atoms, it may be, for example, a methyl, ethyl, n-propyl, n-butyl, octyl, dodecyl or octadecyl group, and it is preferably a group having from 1 to 8 carbon atoms, most preferably a methyl group. When R$^7$ represents a group other than a hydrogen atom, we prefer that Z also should represent a group other than a hydrogen atom.

When R$^8$ represents an alkyl group having from 1 to 18 carbon atoms, it may be any one of the alkyl groups exemplified for R$^7$ and is preferably a group having from 1 to 12, and more preferably from 1 to 8, carbon atoms.

When R$^8$ represents an alkenyl group having 3 or 4 carbon atoms, it may be, for example, an allyl, a 2-butenyl or a 2-methylallyl group.

When R$^8$ represents a group of formula

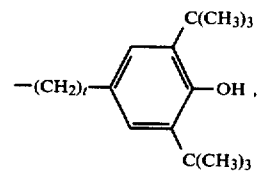

it may be, for example, a 4-hydroxy-3,5-di-t-butylbenzyl group, a 4-hydroxy-3,5-di-t-butylphenethyl group or a 3-(4-hydroxy-3,5-di-t-butylphenyl)propyl group.

When R$^8$ represents a group of formula —CH$_2$CHR$^{21}$(OR$^{22}$), R$^{21}$ represents a hydrogen atom, a methyl group or a phenyl group, preferably a hydrogen atom. R$^{22}$ may represent: a hydrogen atom; an alkyl group having from 1 to 8 carbon atoms, e.g. a methyl, ethyl, n-butyl or octyl group; an allyl group; a benzyl group; or an aliphatic, aromatic, araliphatic or alicyclic acyl group having up to 18 carbon atoms (in which the aryl moiety is optionally substituted by one or more C$_1$–C$_4$ alkyl and/or hydroxy substituents); it is preferably a hydrogen atom or an acyl group. Preferred examples of such acyl groups are identical with those exemplified for the group of formula —COR$^{27}$.

When R$^8$ represents a group of formula —CH$_2$COOR$^{23}$, R$^{23}$ may represent: an alkyl group having from 1 to 18 carbon atoms, e.g. a methyl, ethyl, n-butyl, octyl, dodecyl or octadecyl group, preferably a group having from 1 to 4 carbon atoms; an alkenyl group having 3 or 4 carbon atoms, e.g. an allyl group or a 2-butenyl group; or a phenyl group.

When l is 2 and Y represents a group of formula —CH$_2$CH(OZ)CH$_2$—[OCH$_2$CH(R$^{24}$)]$_m$—OCH$_2$CH(OZ)CH$_2$—, m represents an integer of from 1 to 10, preferably 1, and R$^{24}$ represents a hydrogen atom or a methyl group, preferably a hydrogen atom.

When Y represents a group of formula —CH$_2$CH(OZ)CH$_2$—[OWO—CH$_2$CH(OZ)CH$_2$]$_n$—, n represents an integer of from 1 to 10, preferably from 1 to 3 and most preferably 1.

When W represents a group of formula

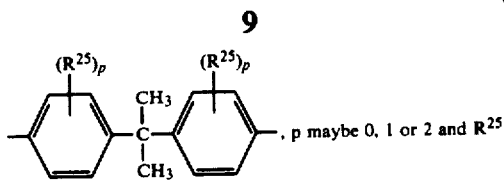, p maybe 0, 1 or 2 and $R^{25}$ p may be 0, 1 or $R^{25}$ represents a halogen atom, e.g. chlorine or bromine. We prefer those compounds in which p is 0, i.e. the benzene rings in the group represented by W are unsubstituted. Examples of such groups are:

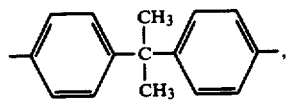

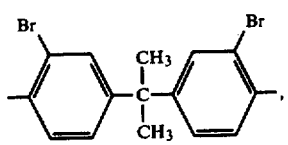

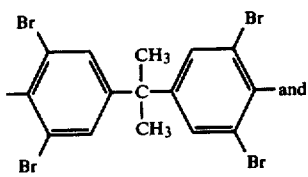

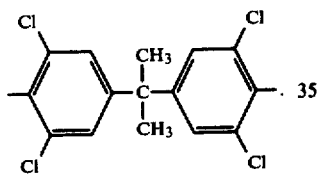

When W represents c group of formula —CO—$(CH_2$- of $)_q$—CO—, q represents an integer of from 1 to 10, preferably from 2 to 8 and most preferably 4. Examples of such groups include malonyl, succinyl, adipoyl, suberoyl, sebacoyl and dodecanedioyl groups.

Other groups which may be represented by W are phthaloyl, isophthaloyl, terephthaloyl, 1,2-cyclohexanedicarbonyl, 1,3-cyclohexanedicarbonyl and 1,4-cyclohexanedicarbonyl, of which we particularly prefer phthaloyl and 1,2-cyclohexanedicarbonyl.

Of the piperidine derivatives of formula (I), we prefer the following classes of compound:
compounds wherein $R^1$ represents a hydrogen atom;
compounds wherein X represents the group —$CH_2$—;
compounds wherein X represents a group of formula

in which $R^2$ represents a hydrogen atom, an alkanoyl group having from 2 to 18 carbon atoms, a benzoyl group, a 3-(4-hydroxy-3,5-di-t-butylphenyl)propionyl group, an N-phenylcarbamoyl group or an alkyl group having from 1 to 8 carbon atoms, particularly those in which $R^2$ represents a hydrogen atom, an alkanoyl group having from 2 to 18 carbon atoms, a 3-(4-hydroxy-3,5-di-t-butylphenyl)propionyl group or a benzoyl group; compounds in which X represents a group of formula

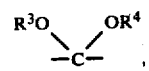

in which $R^3$ and $R^4$ together represent one of the groups of formula

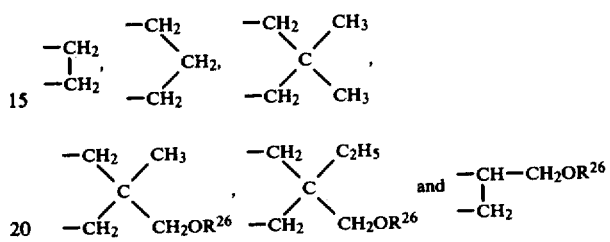

in which $R^{26}$ is as defined above, particularly those in which $R^3$ and $R^4$ together represent a group of formula

compounds in which X represents a group of formula

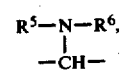

in which $R^5$ represents an alkyl group having from 1 to 8 carbon atoms and $R^6$ represents an alkanoyl group having from 2 to 18 carbon atoms or a benzoyl group, or in which $R^5$ and $R^6$ together represent a group of formula —$(CH_2)_2$—O—$(CH_2)_2$—, particularly those in which $R^5$ represents an alkyl group having from 1 to 4 carbon atoms and $R^6$ represents an acetyl group; compounds in which X represents a group of formula

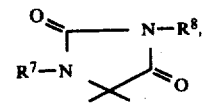

in which $R^7$ represents a hydrogen atom or an acetyl group and $R^8$ represents an alkyl group having from 1 to 12 carbon atoms or a group of formula —$CH_2CH_2OR^{22}$, in which $R^{22}$ represents a hydrogen atom, an alkanoyl group having from 2 to 18 carbon atoms, a benzoyl group or a 3-(4-hydroxy-3,5-di-t-butylphenyl)-propionyl group, particularly those in which $R^7$ represents a hydrogen atom and $R^8$ represents an alkyl group having from 1 to 12 carbon atoms;

compounds in which l is 2 and Y represents one of the groups of formula —$CH_2CH(OZ)CH_2$—[OWO—$CH_2CH(OZ)CH_2]_r$—, —$CH_2CH(OZ)CH_2$—O$CH_2CH_2OCH_2CH(OZ)CH_2$—or —$CH_2CH(OZ)CH_2$—[O$CH_2CH(OZ)CH_2]_2$—or in which l is 3 and Y represents one of the groups of formula

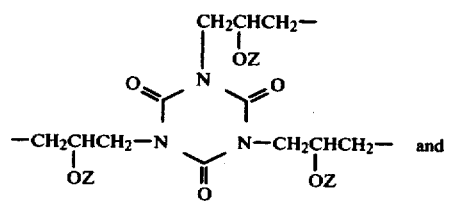

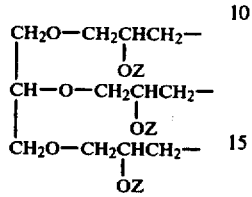

in which r is an integer of from 1 to 3, W represents a group of formula

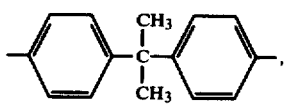

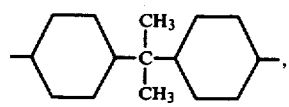

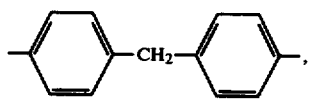

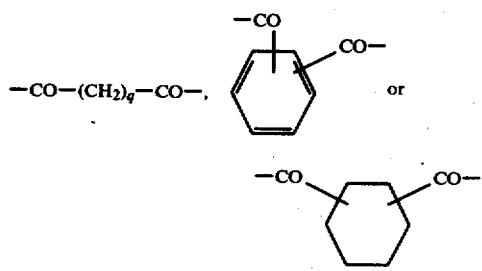

in which q and Z are as defined above, particularly those in which Y represents one of the groups of formulae —CH₂CH(OZ)CH₂—OWO—CH₂CH(OZ)CH₂— and —CH₂CH(OZ)CH₂—OCH₂CH₂O—CH₂CH(OZ)CH₂—, in which Z is as defined above and W represents one of the groups of formulae —CO—(CH₂)_q—CO—, in which q is an integer from 2 to 8; and compounds wherein Z represents a hydrogen atom, an alkyl group having from 1 to 8 carbon atoms, an alkanoyl group having from 2 to 18 carbon atoms, a benzoyl group, a 3-(4-hydroxy-3,5-di-t-butylphenyl)-propionyl group or an N-phenylcarbamoyl group, particularly those in which Z represents a hydrogen atom, an alkanoyl group having from 2 to 18 carbon atoms, a benzoyl group or a 3-(4-hydroxy-3,5-di-t-butylphenyl)-propionyl group.

In the case of the compounds of formula (I) in which $R^1$ represents a methyl group, the compounds can exist in the form of various stereoisomers and the present invention embraces both the individual stereoisomers as well as mixtures of any two or more thereof.

The present invention also provides acid addition salts of the compounds of formula (I). The nature of the acid employed to form such acid addition salts is not critical, provided that, where the acid addition salts is to be used to stabilize a polymer, the acid employed does not adversely effect the stability of the polymer. Examples of suitable acids include: inorganic acids, such as sulphuric acid, hydrochloric acid and phosphoric acid; organic carboxylic acids, such as formic acid, acetic acid, valeric acid, stearic acid, oxalic acid, adipic acid, sebacic acid, maleic acid, benzoic acid, p-t-butylbenzoic acid, 4-hydroxy-3,5-di-t-butylbenzoic acid, salicylic acid or terephthalic acid; sulphonic acids, such as methanesulphonic acid or p-toluenesulphonic acid, and organic phosphonic acids, such as phenylphosphonic acid.

The following is a non-limiting list of individual piperidine derivatives of formula (I). The numbers appended to the compounds in this list will be used to identify them hereinafter in the Examples. In these formulae, the abbreviation t-Bu is used to represent the t-butyl group.

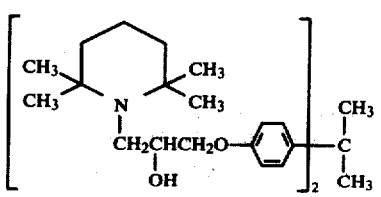

1.

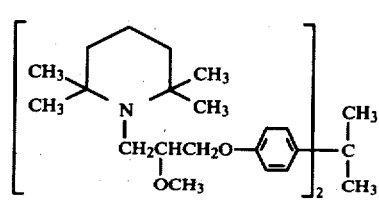

2.

-continued
3.
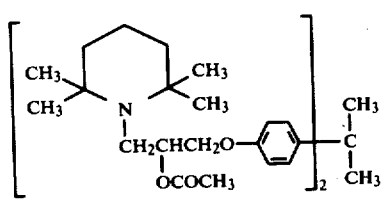
4.
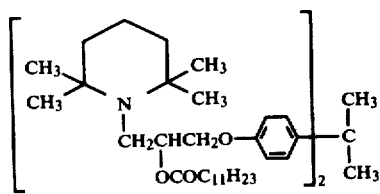
5.
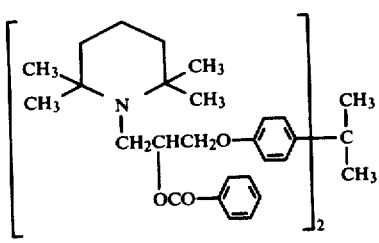
6.
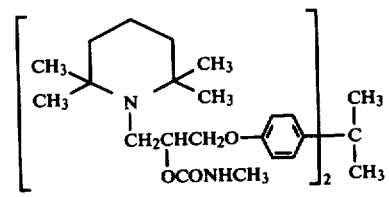
7.
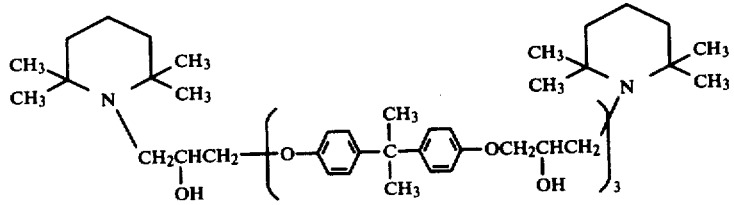
8.
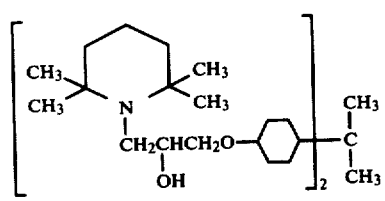
9.
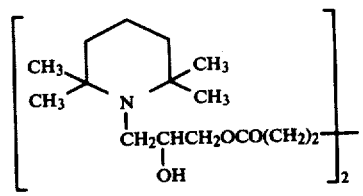
10.
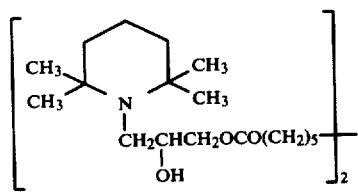
11.
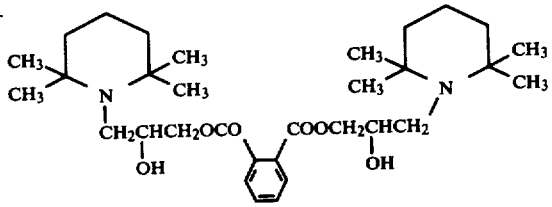
12.
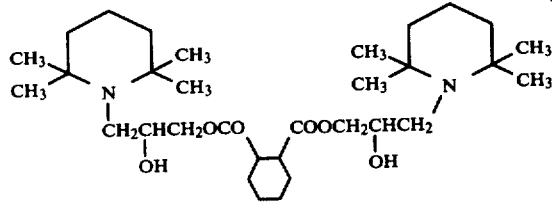
13.
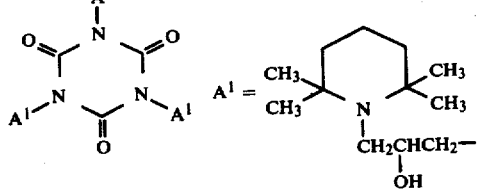
14.
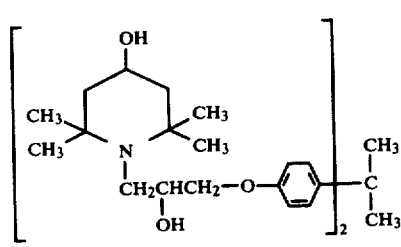
15.
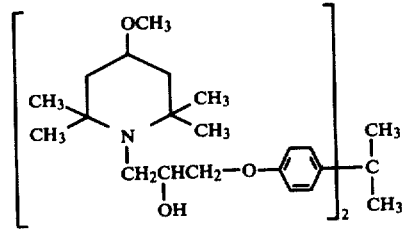

16.
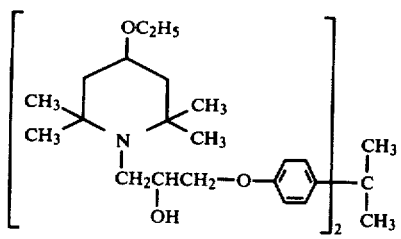
17.
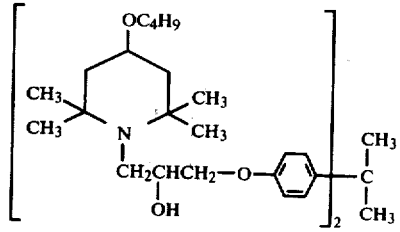
18.
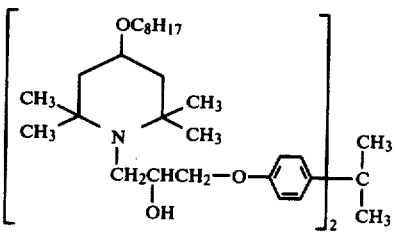
19.
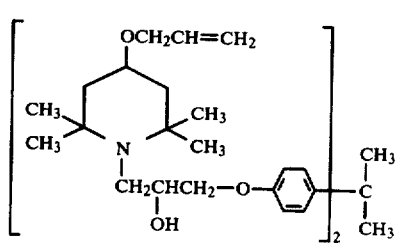
20.
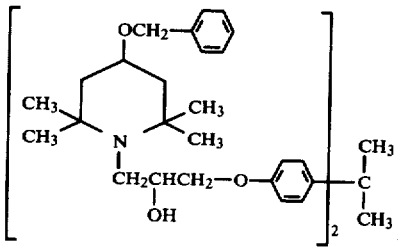
21.
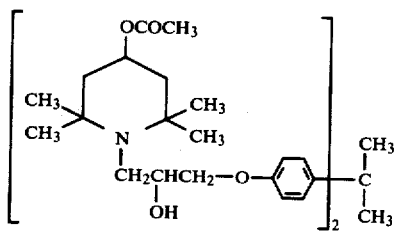
22.
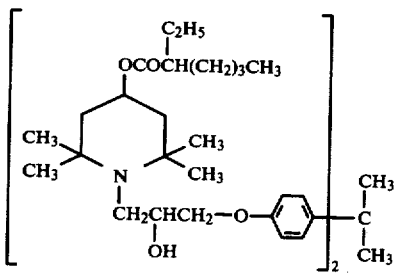
23.
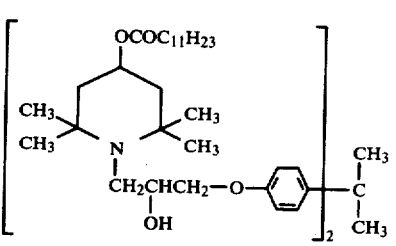
24.
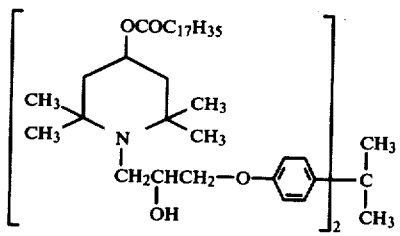
25.
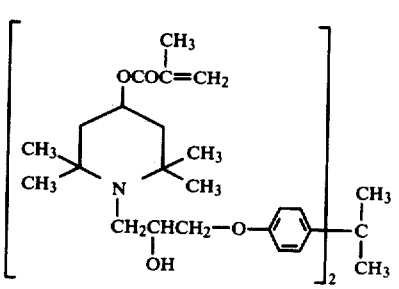
26.
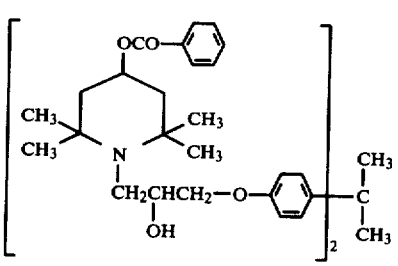
27.
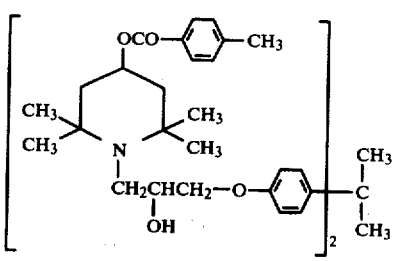

-continued
28. 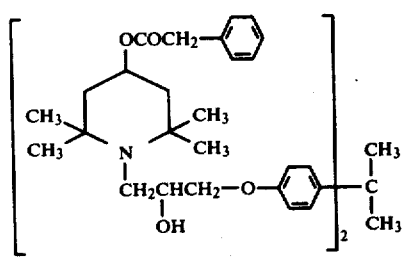
29. 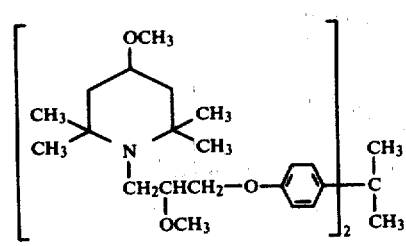
30. 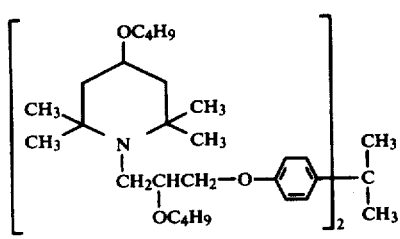
31. 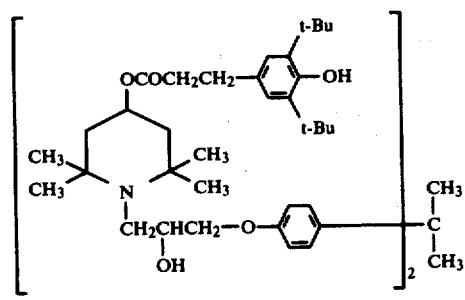
32. 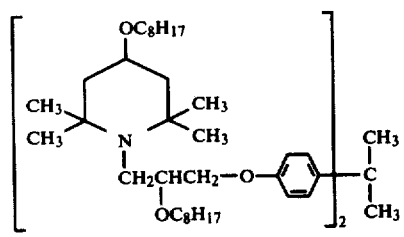
33. 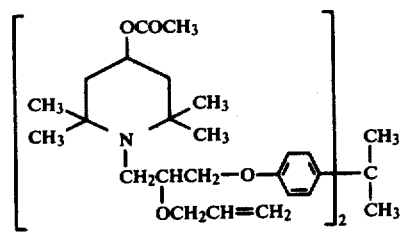
34. 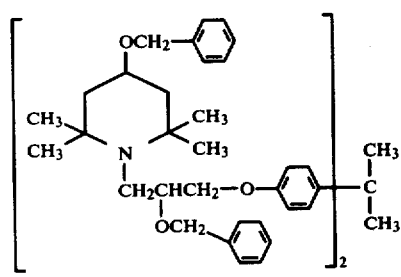
35.
36. 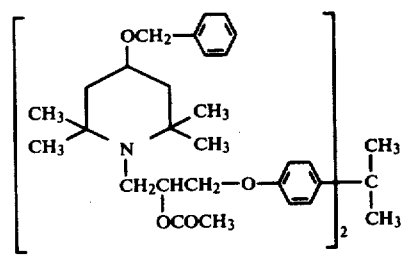
37. 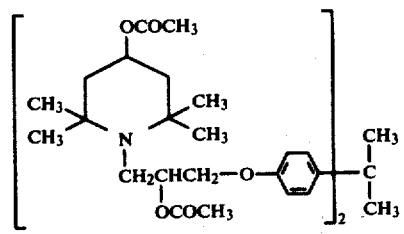

-continued
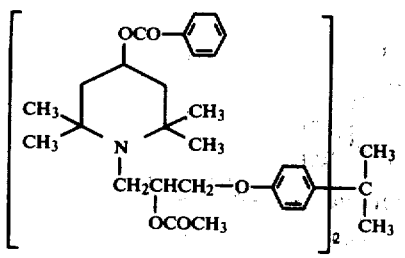 38.
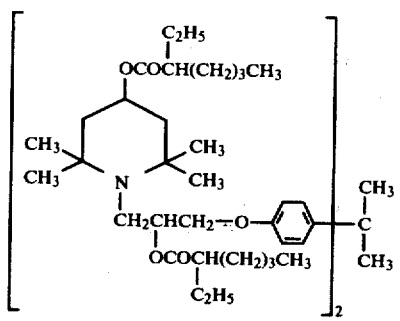 39.
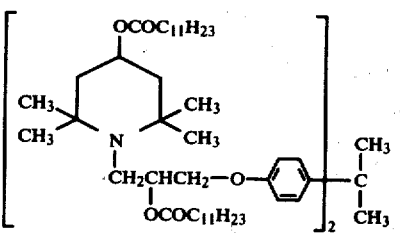 40.
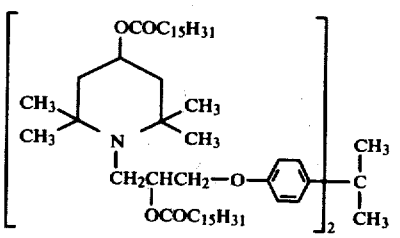 41.
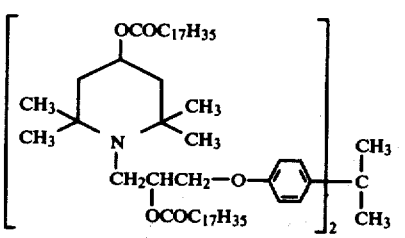 42.
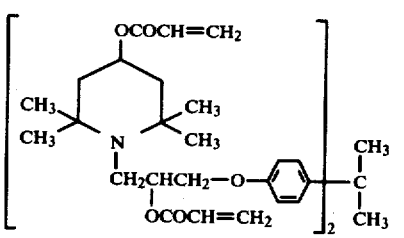 43.
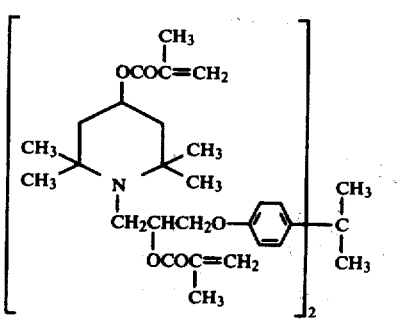 44.
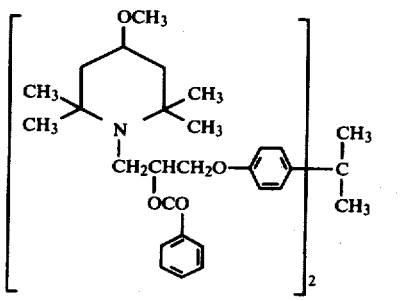 45.
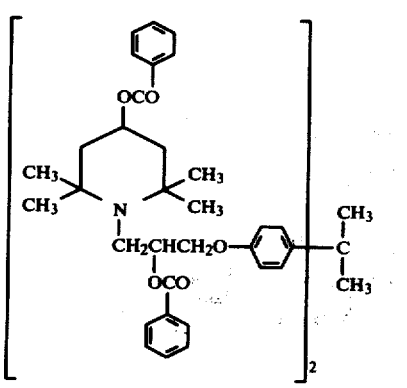 46.
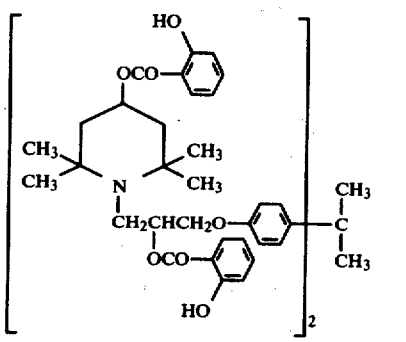 47.

-continued
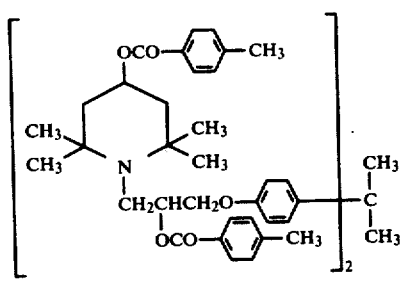 48.
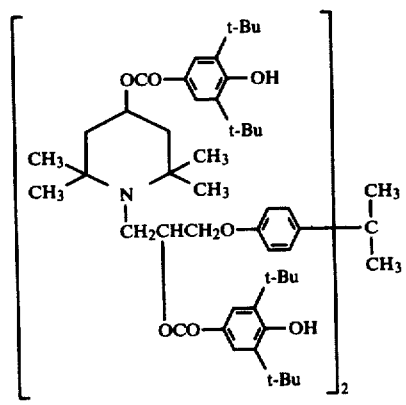 49.
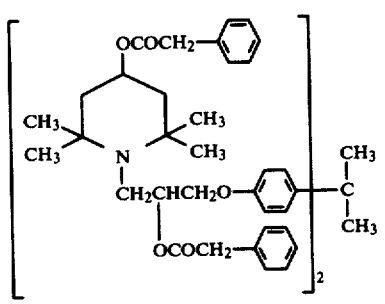 50.
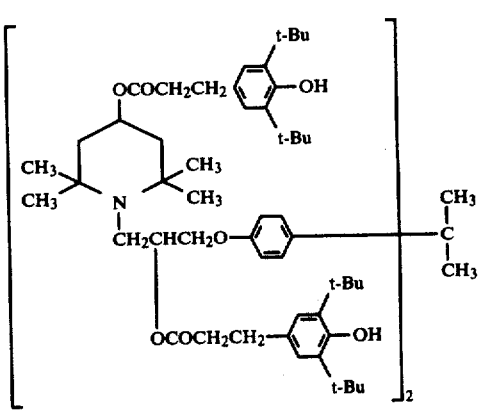 51.
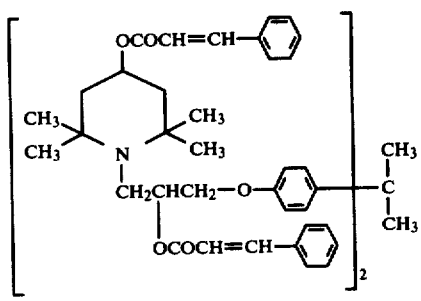 52.
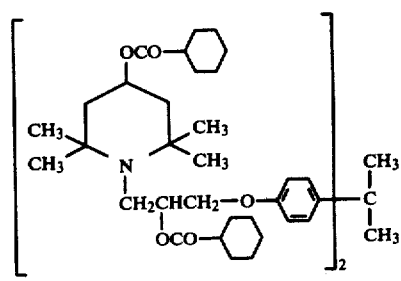 53.
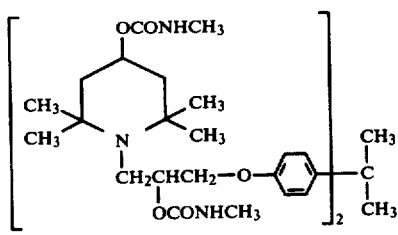 54.
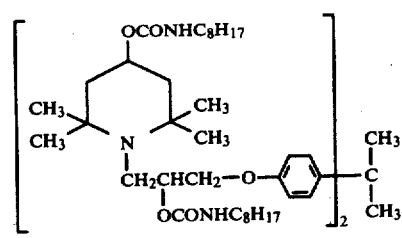 55.
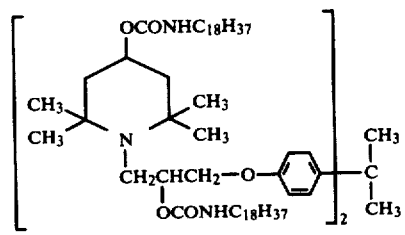 56.
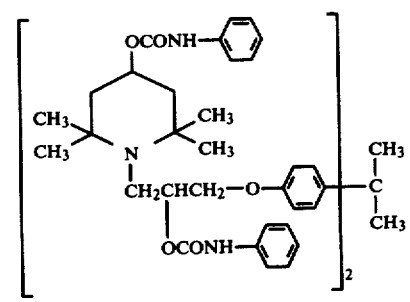 57.

-continued
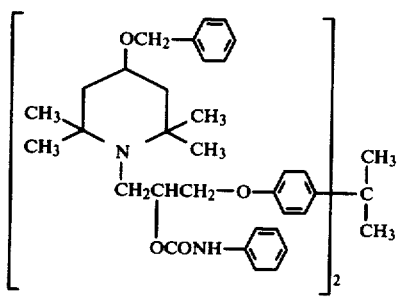 58.
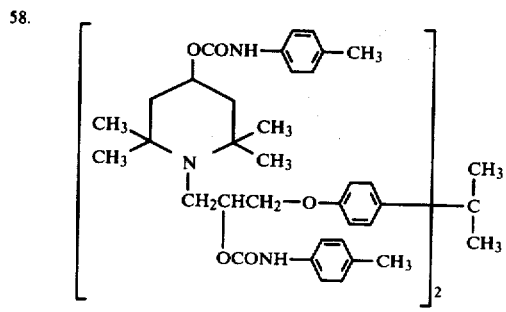 59.
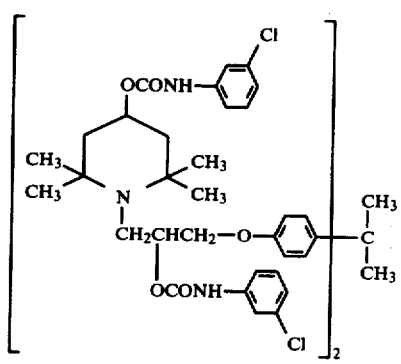 60.
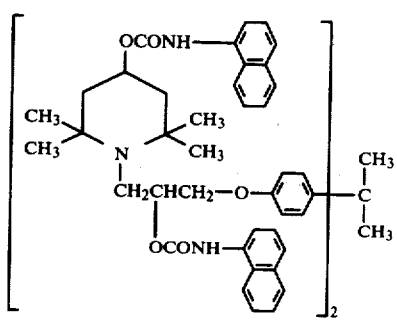 61.
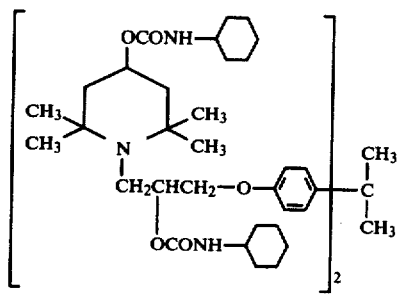 62.
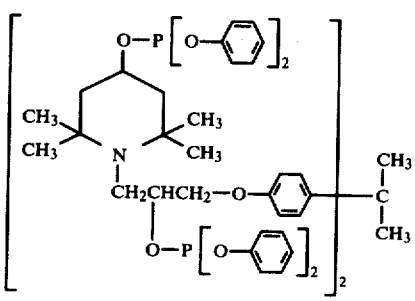 63.
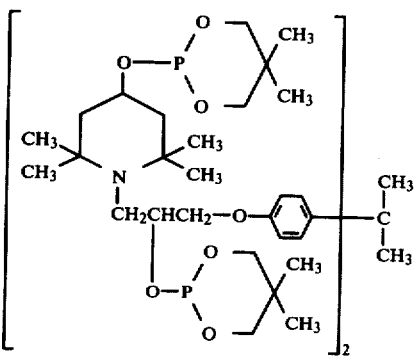 64.

-continued
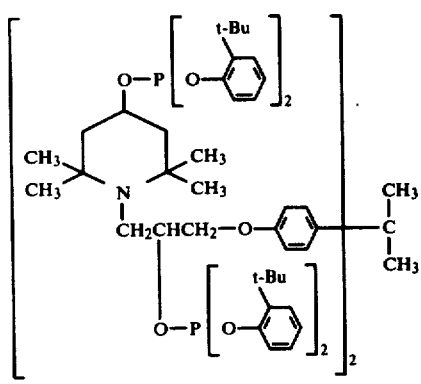 66.
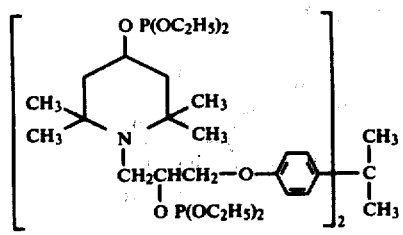 67.
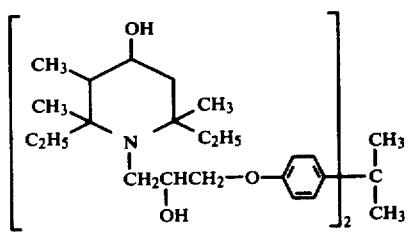 68.
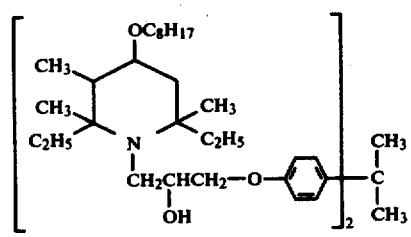 69.
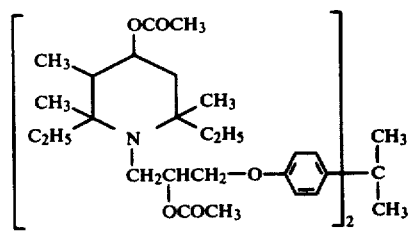 70.
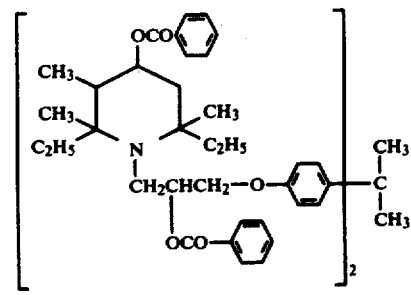 71.
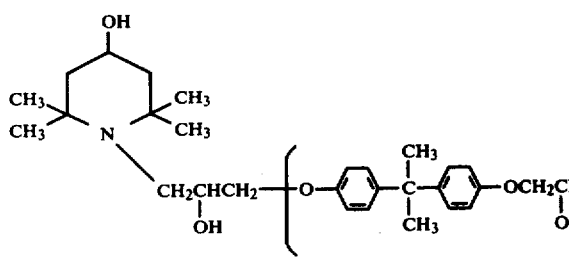 72.
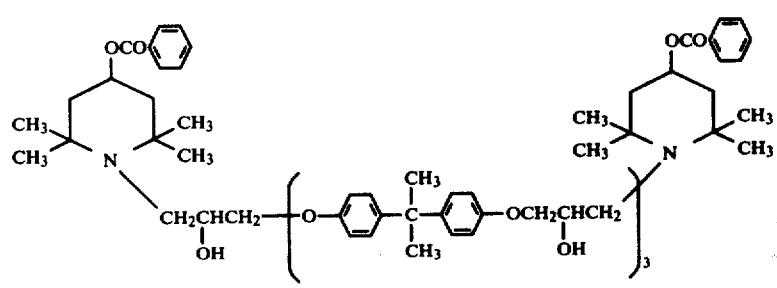 73.

-continued
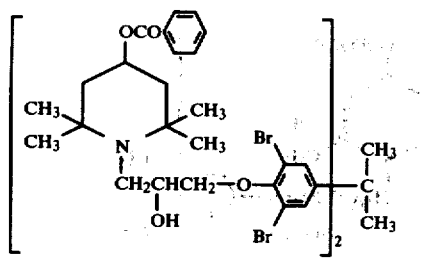 74.
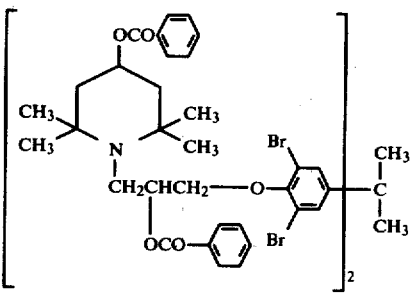 75.
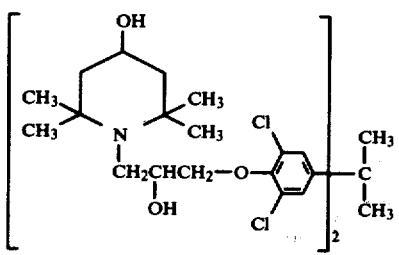 76.
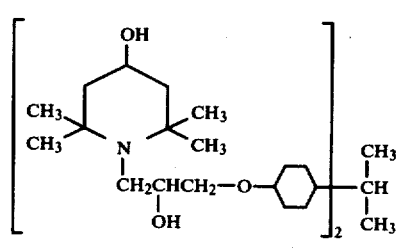 77.
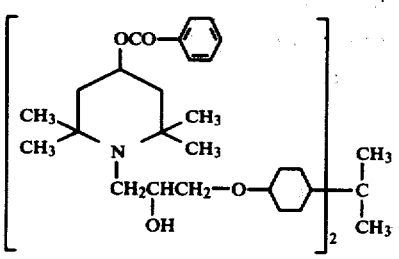 78.
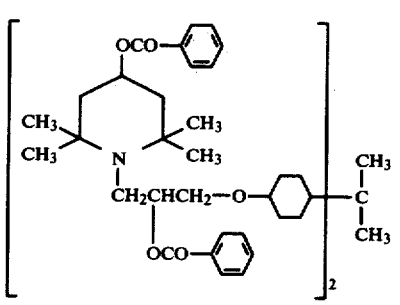 79.
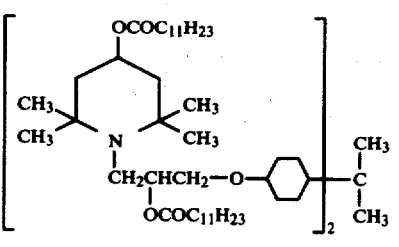 80.
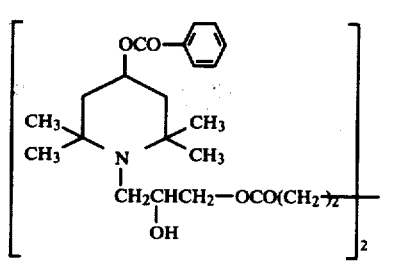 81.
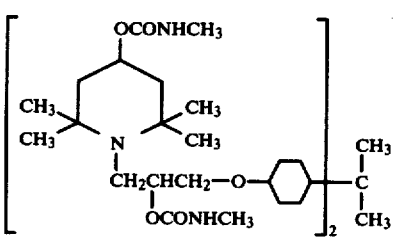 82.
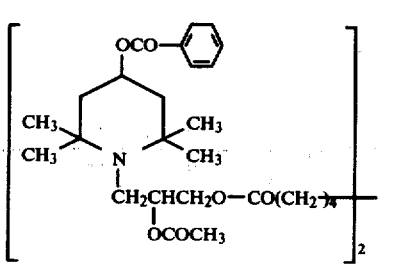 83.
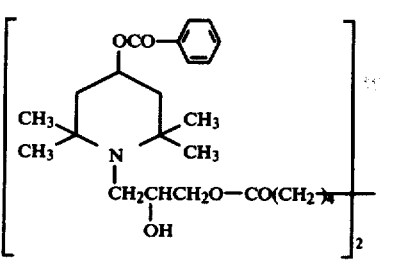 84.
85.

86.
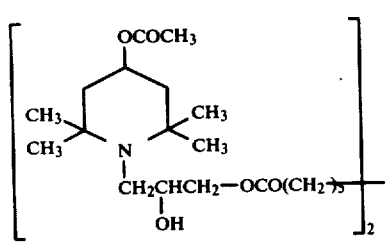
87.
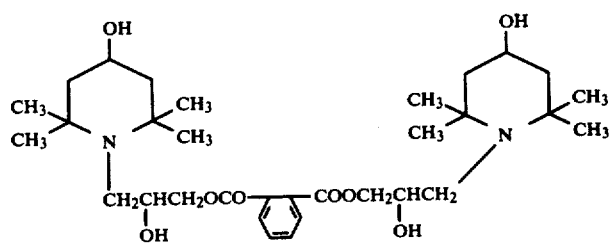
88.
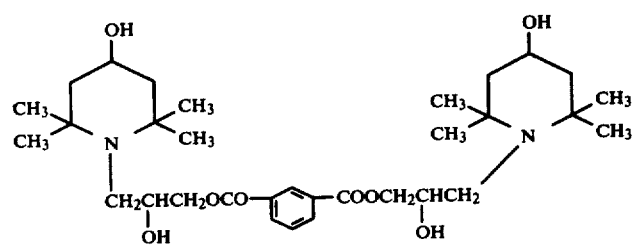
89.
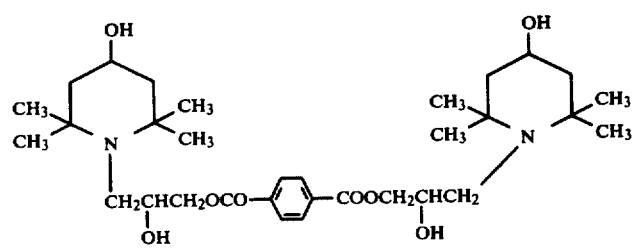
90.
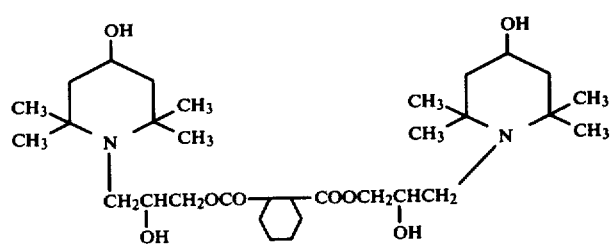
91.
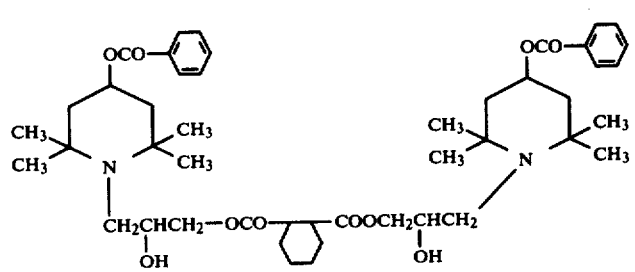

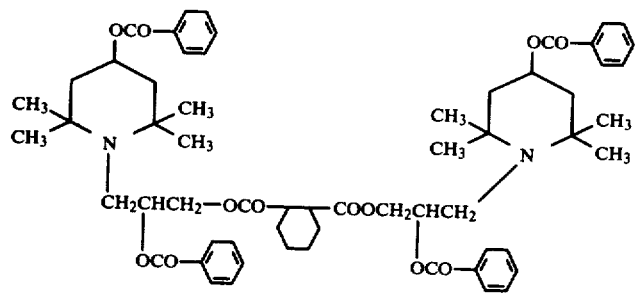
92.
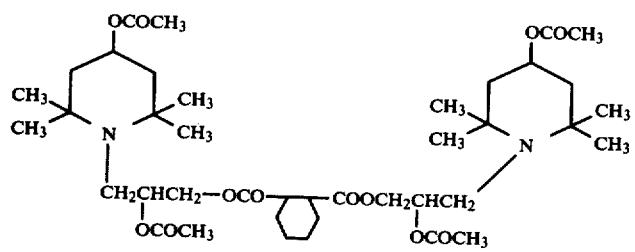
93.
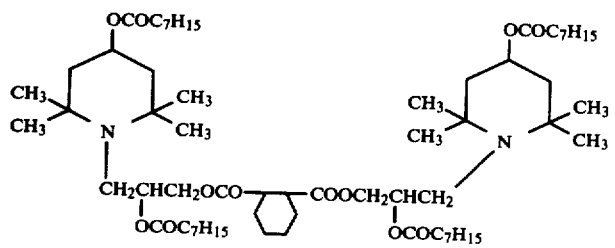
94.
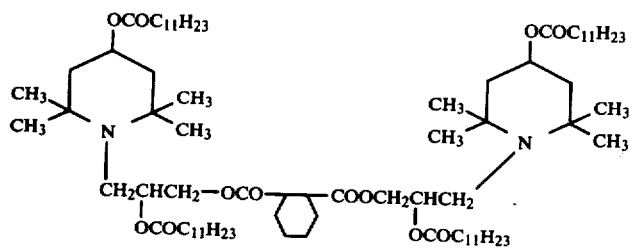
95.
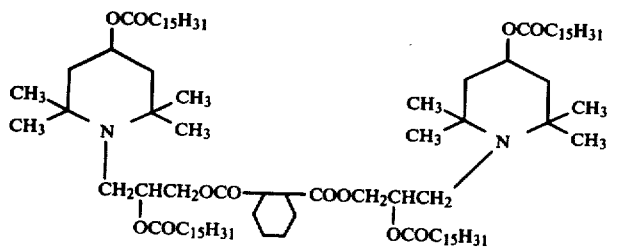
96.
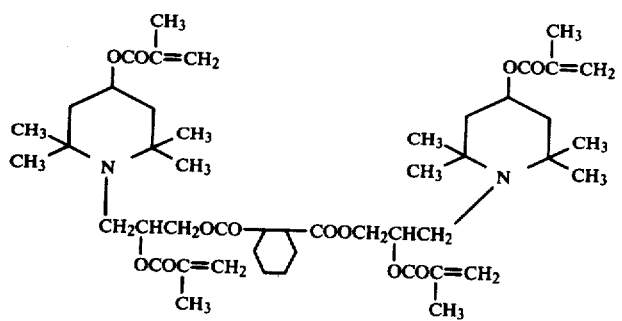
97.

-continued
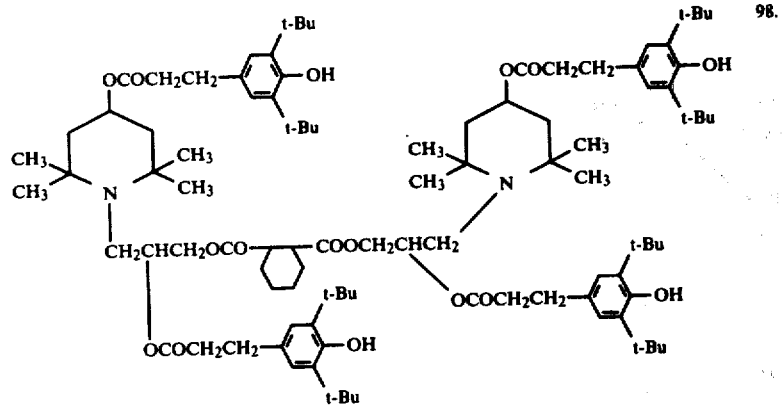 98.
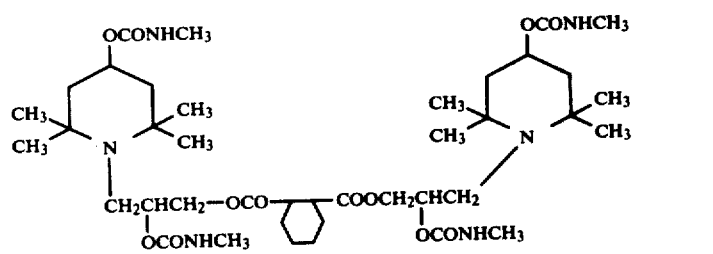 99.
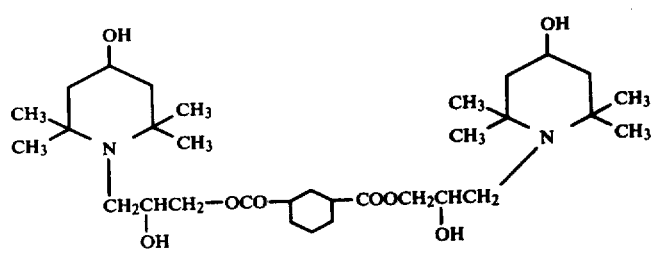 100.
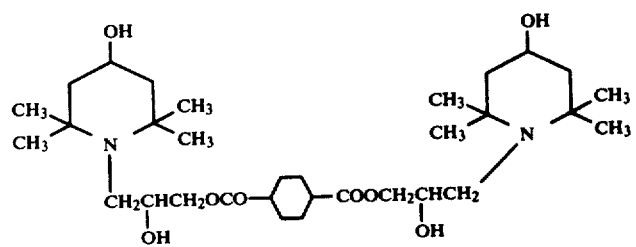 101.
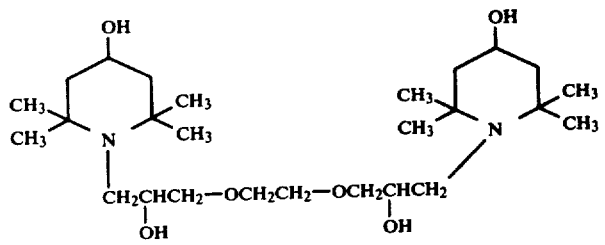 102.
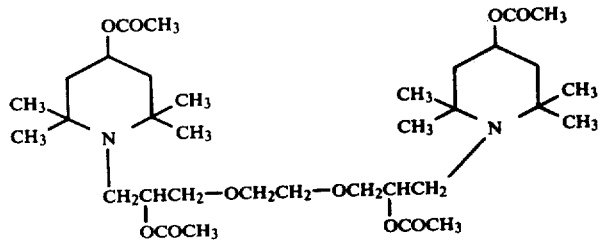 103.

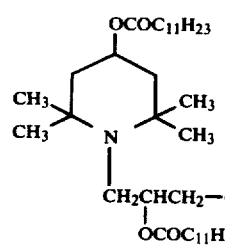 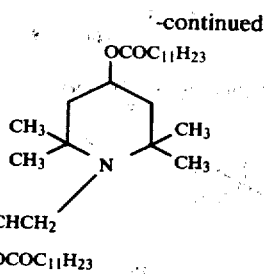 104.
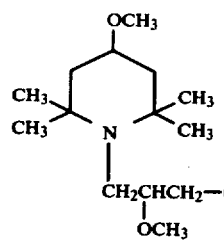 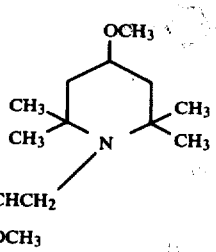 105.
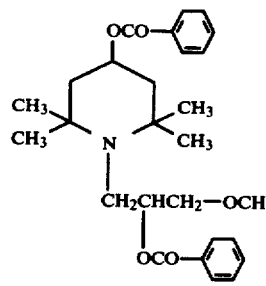 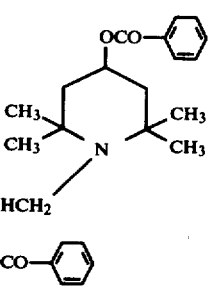 106.
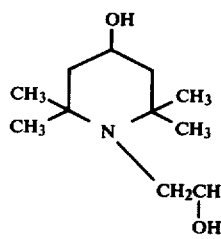 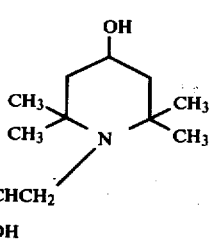 107.
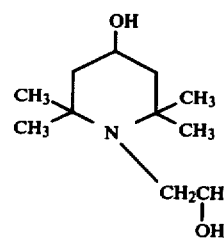 108.
109.  110.
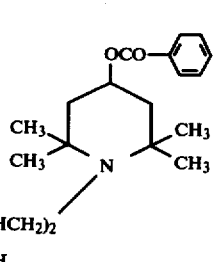

-continued
111.
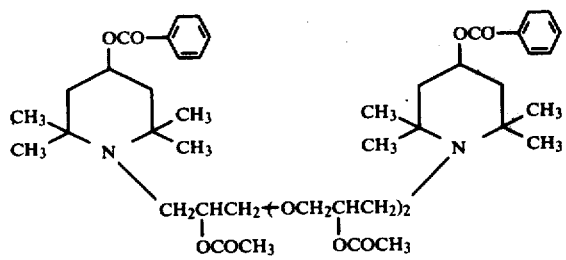
112.
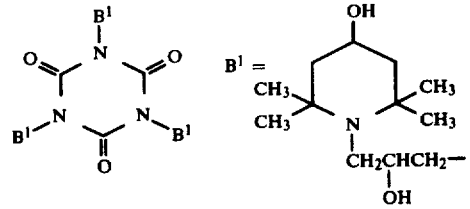
113.
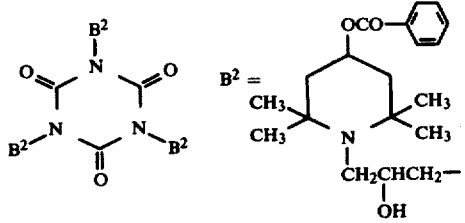
114.
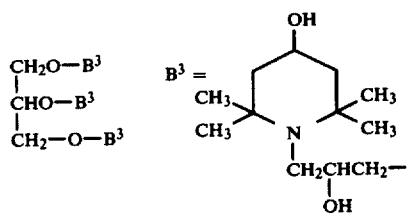
115.
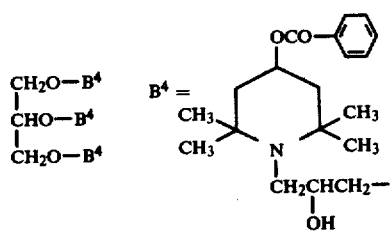
116.
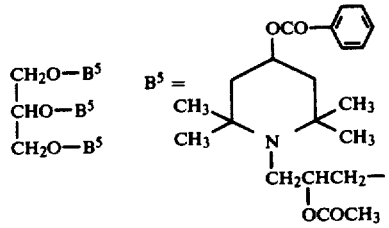
117.
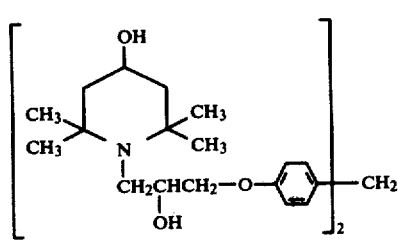
118.
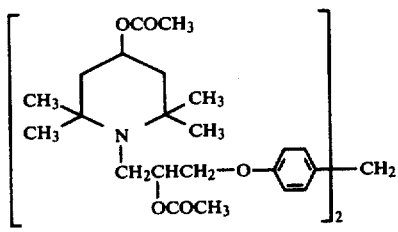
119.
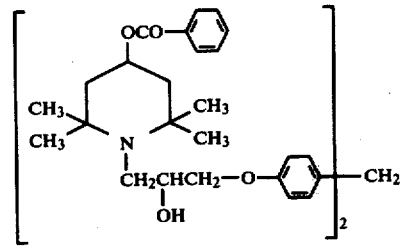
120.
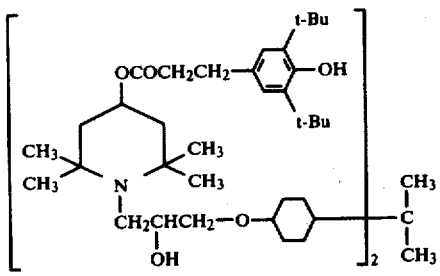
121.
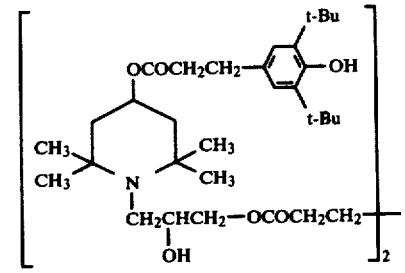

-continued
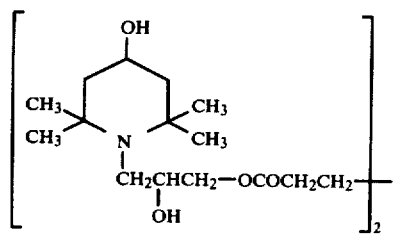 122.
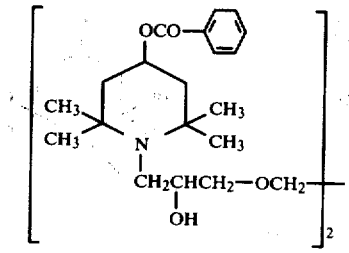 123.
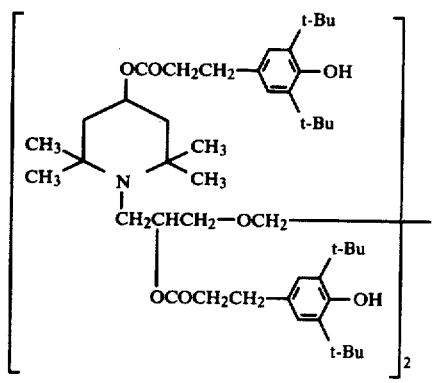 124.
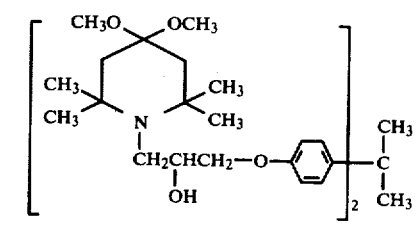 125.
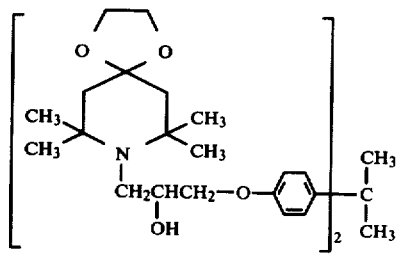 126.
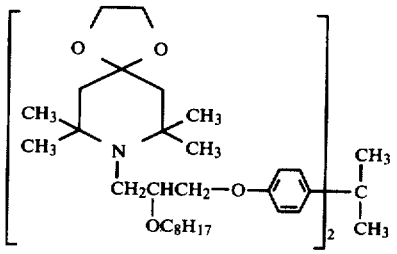 127.
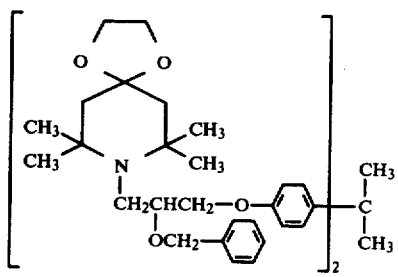 128.
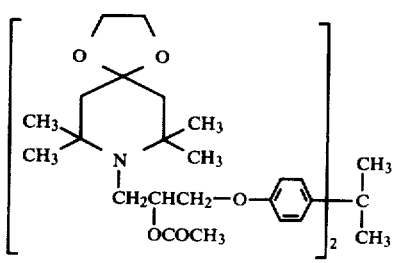 129.
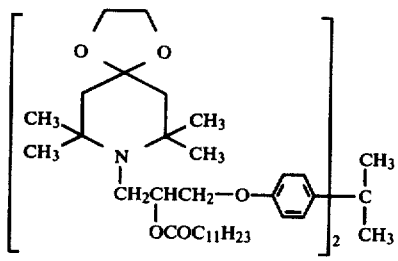 130.
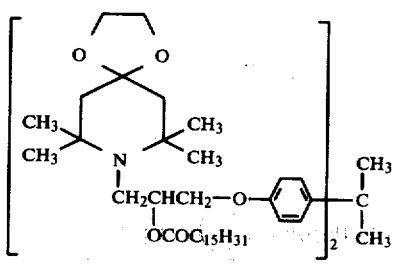 131.

-continued
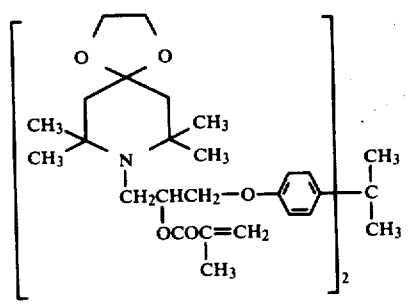
132.
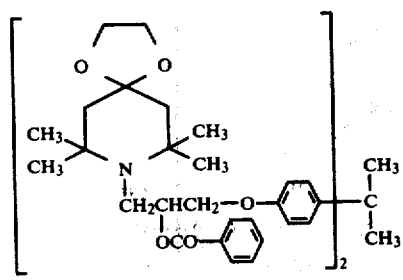
133.
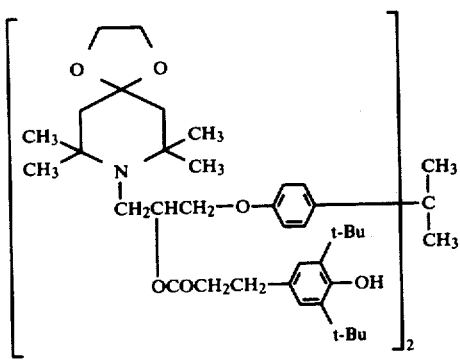
134.
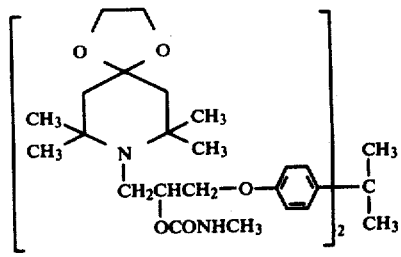
135.
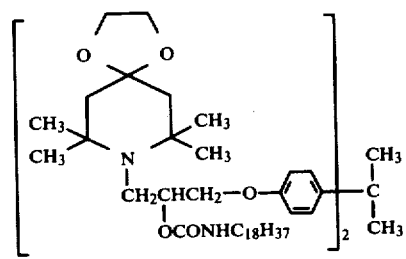
136.
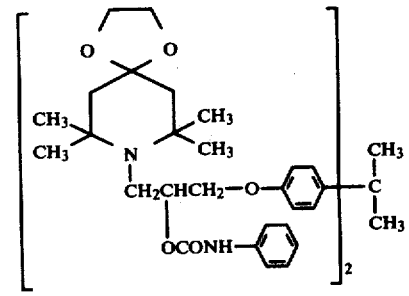
137.
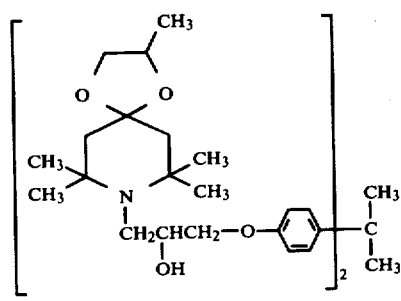
138.
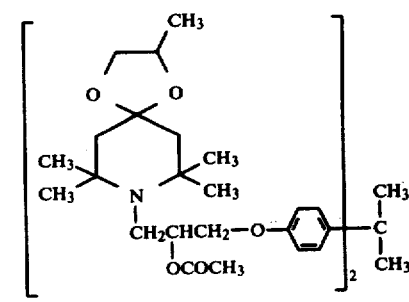
139.
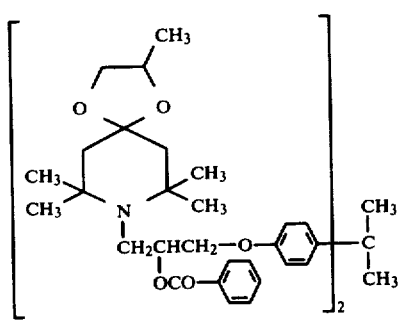
140.
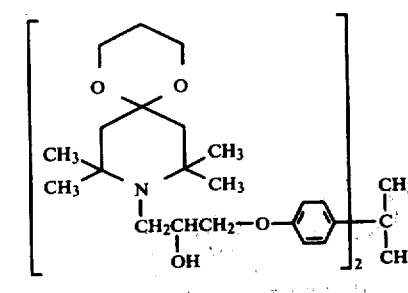
141.

-continued
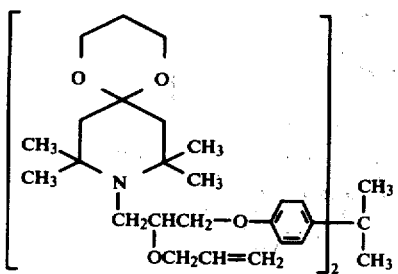 142.
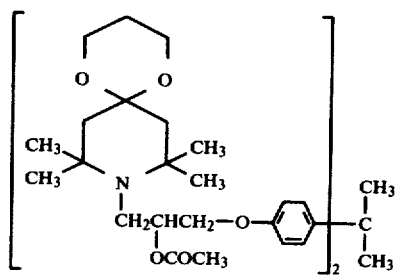 143.
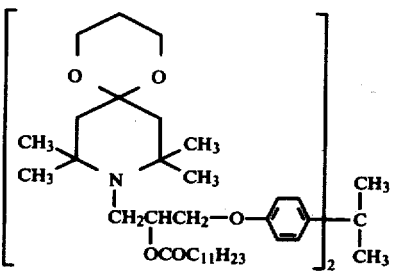 144.
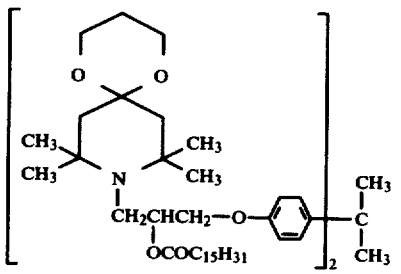 145.
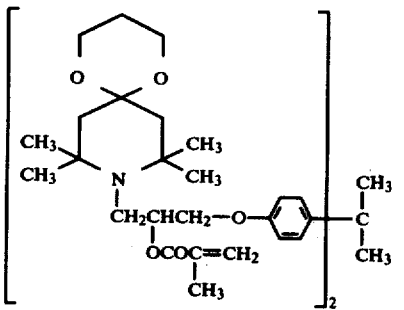 146.
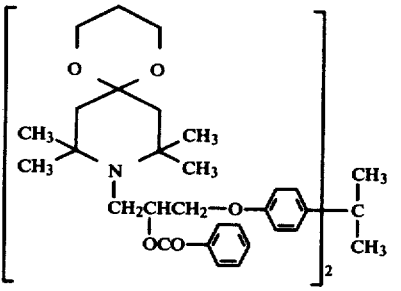 147.
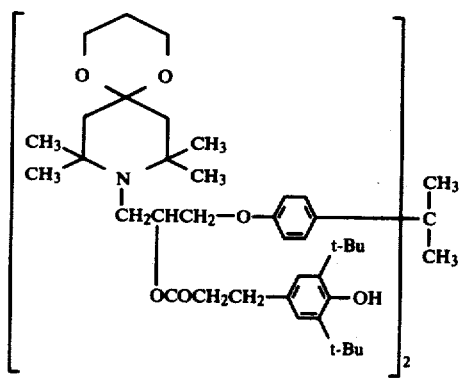 148.
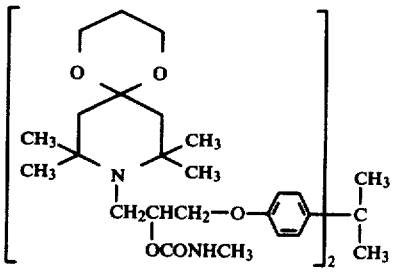 149.
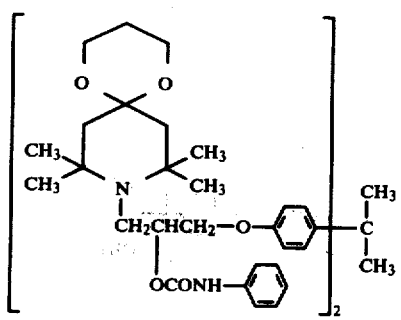 150.

-continued
151. 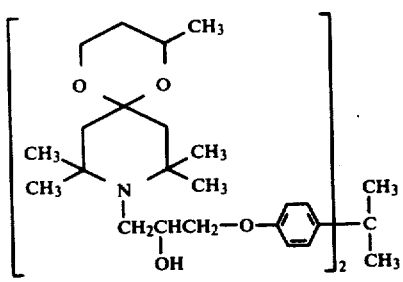
152. 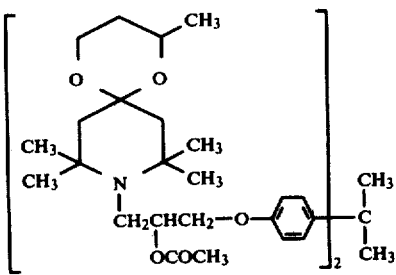
153. 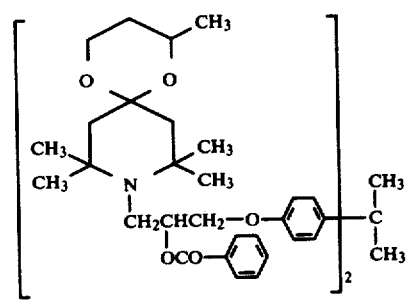
154. 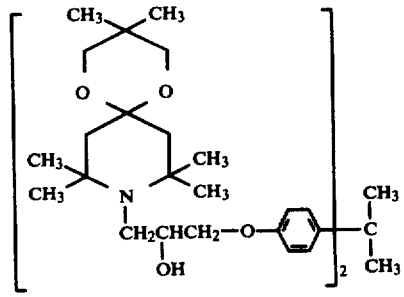
155. 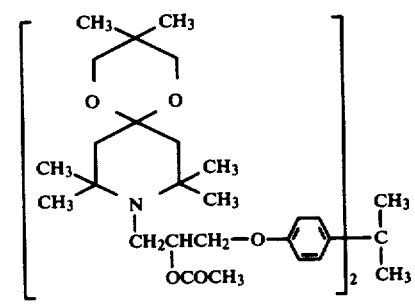
156. 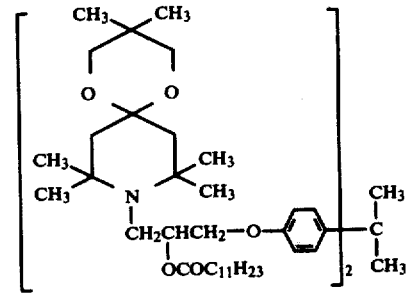
157. 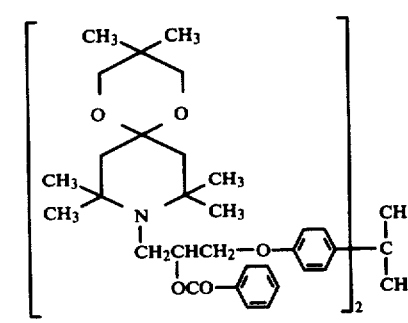
158. 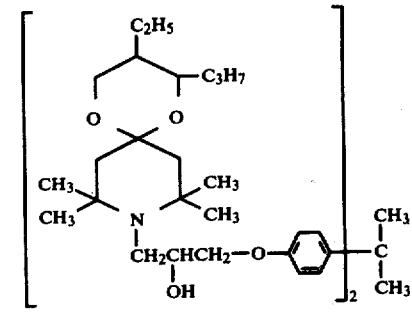
159. 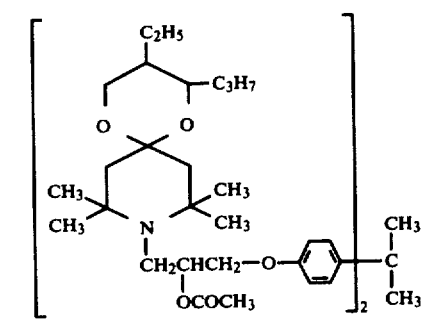
160. 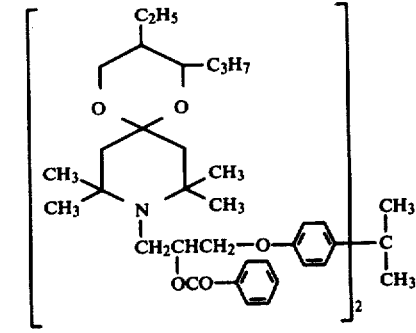

-continued
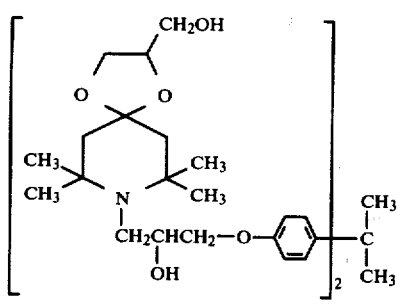 161.
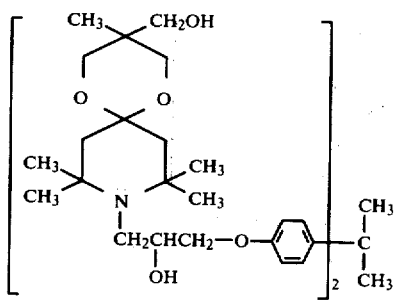 162.
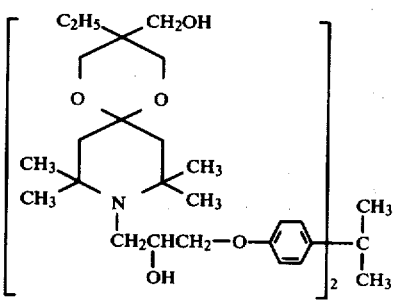 163.
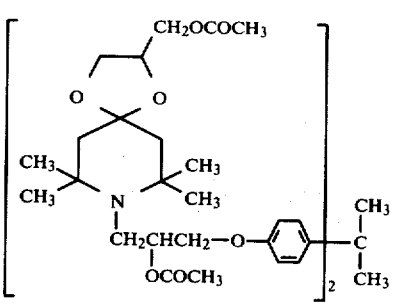 164.
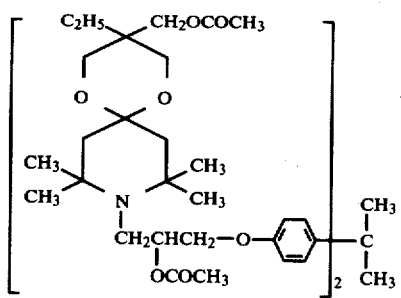 165.
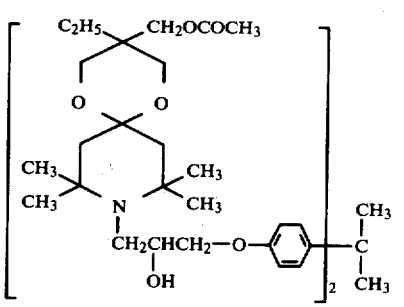 166.
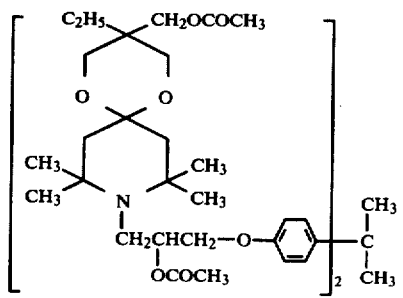 167.
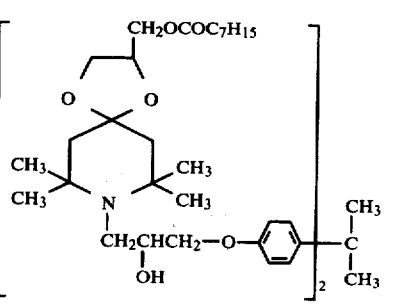 168.
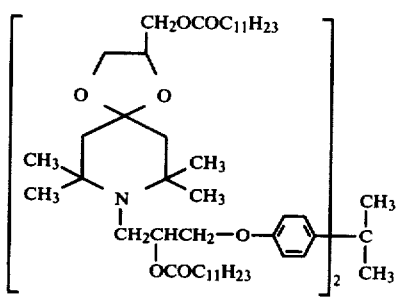 169.
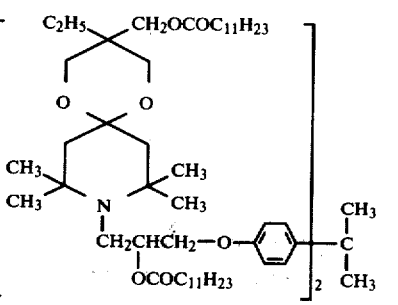 170.

-continued
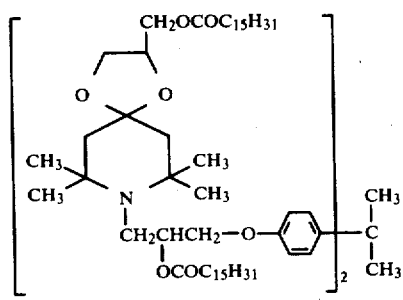 171.
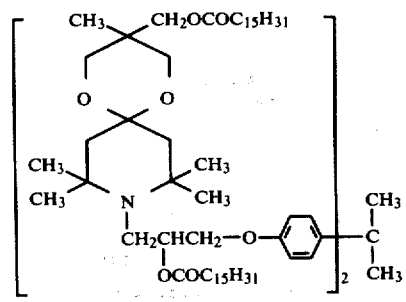 172.
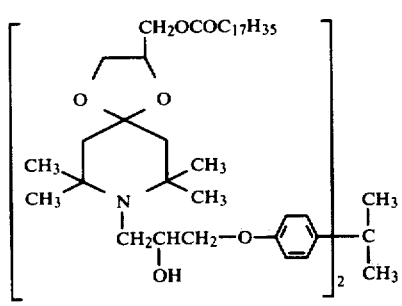 173.
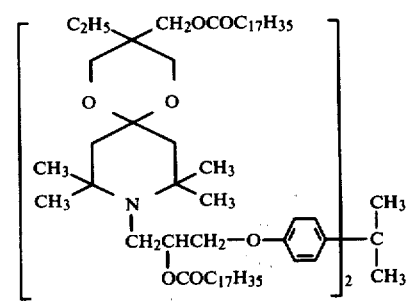 174.
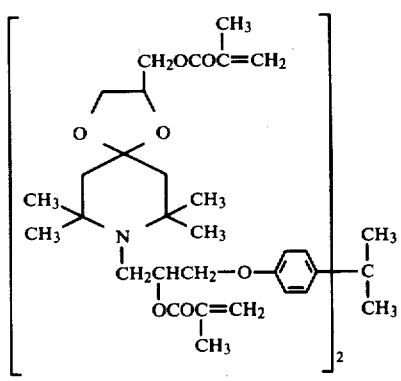 175.
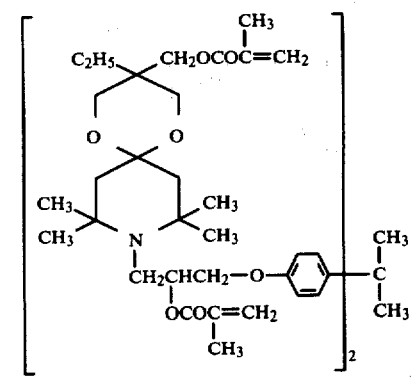 176.
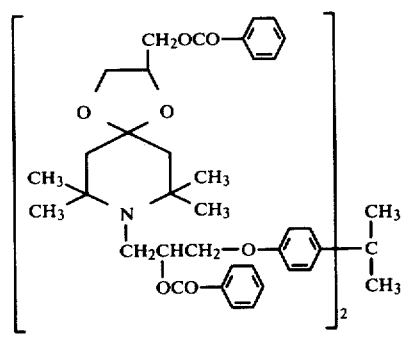 177.
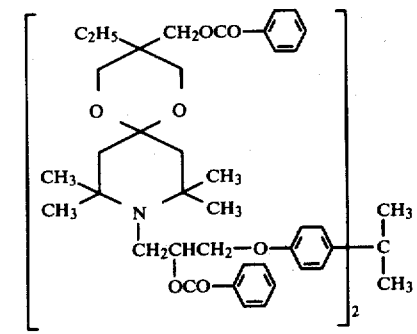 178.

-continued
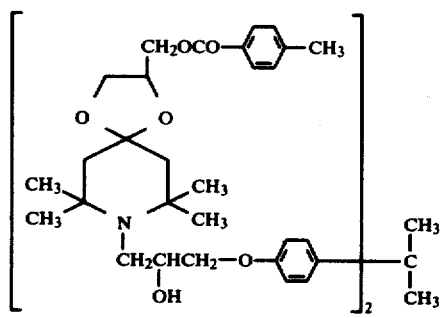 179.
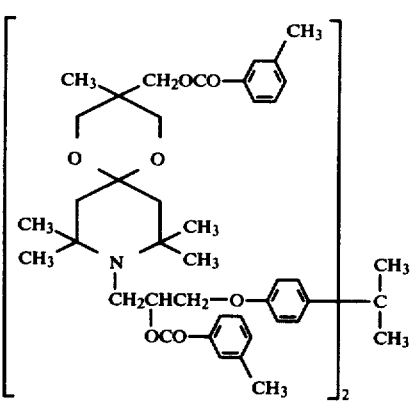 180.
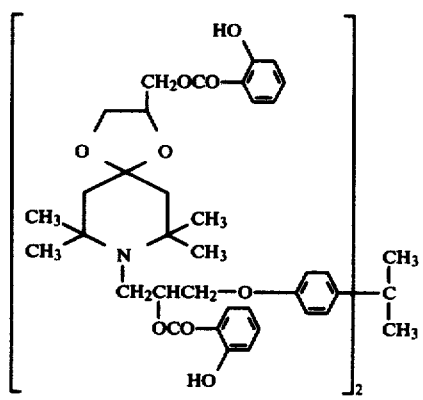 181.
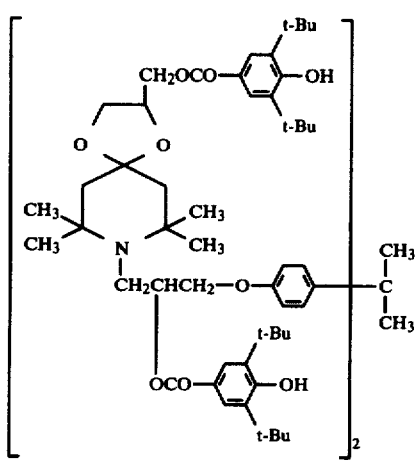 182.
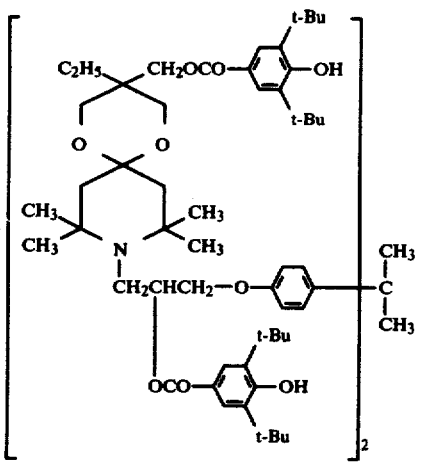 183.
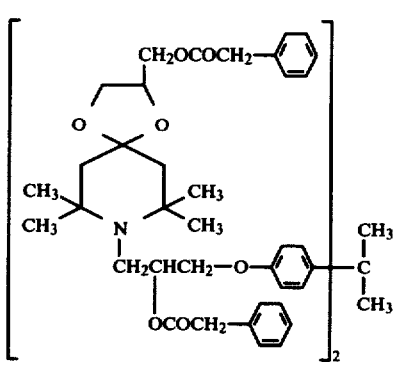 184.

-continued
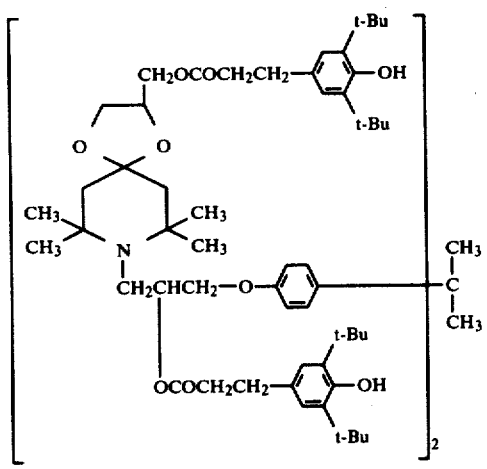 185.
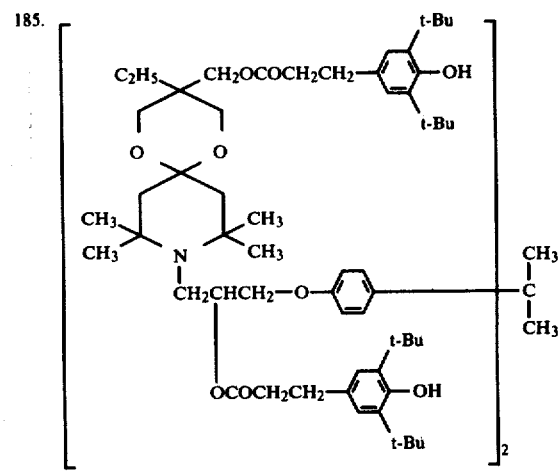 186.
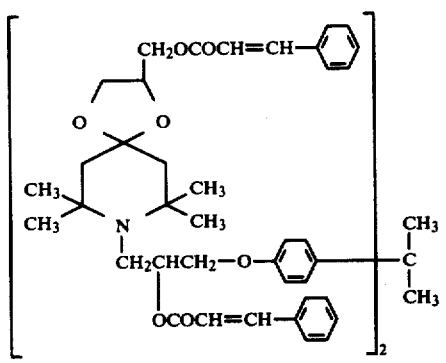 187.
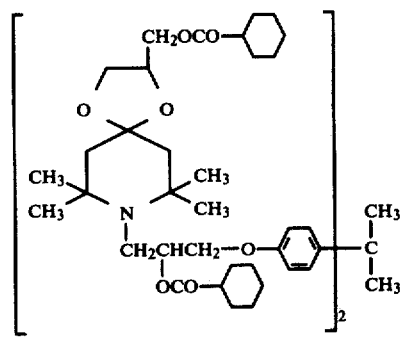 188.
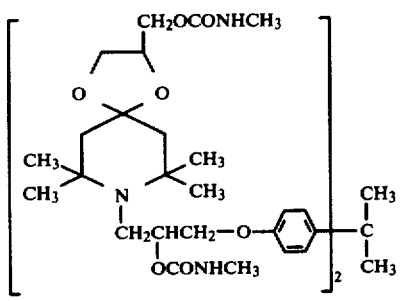 189.
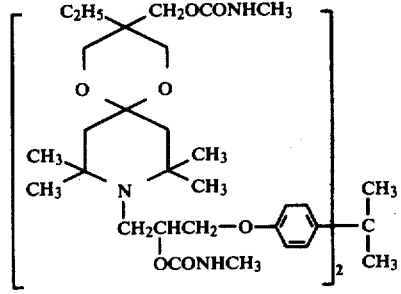 190.
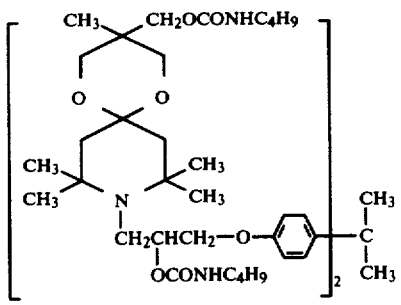 191.
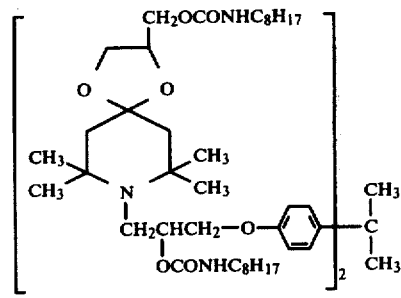 192.

-continued
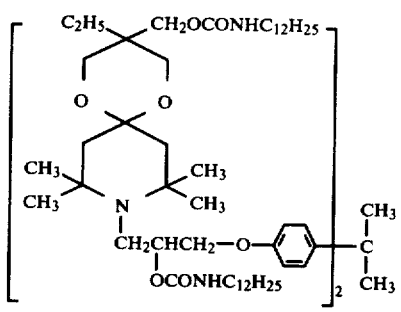 193.
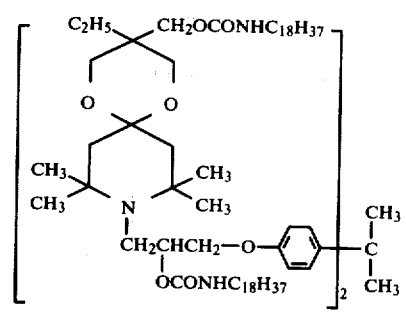 194.
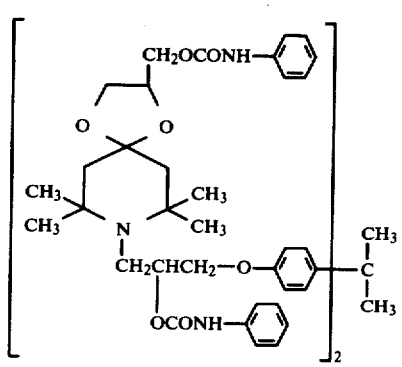 195.
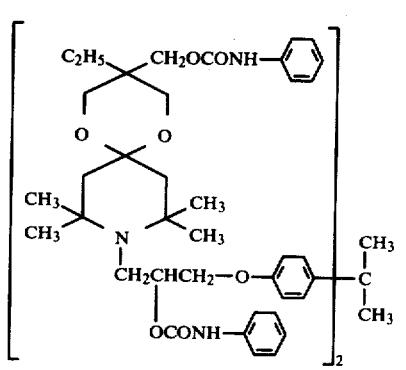 196.
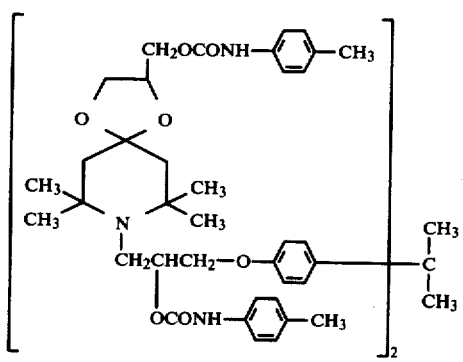 197.
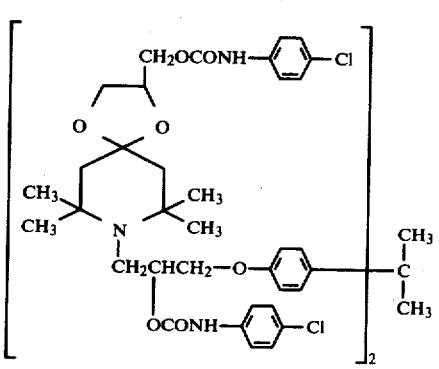 198.
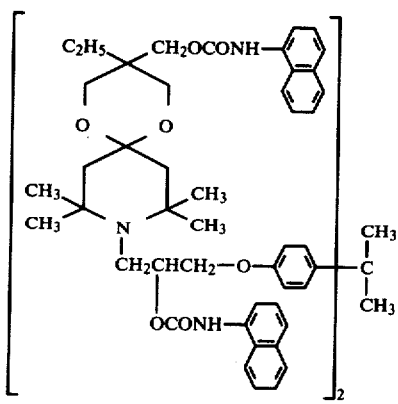 199.
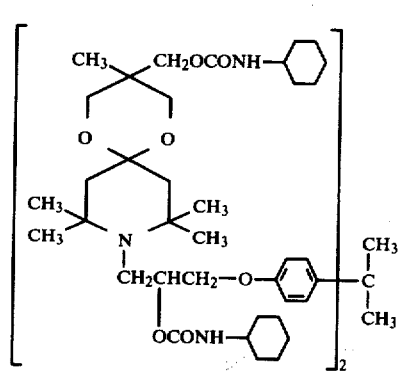 200.

-continued
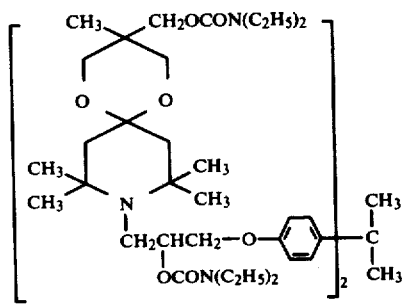 201.
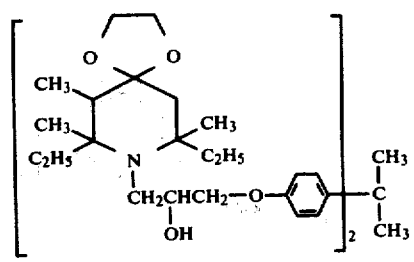 202.
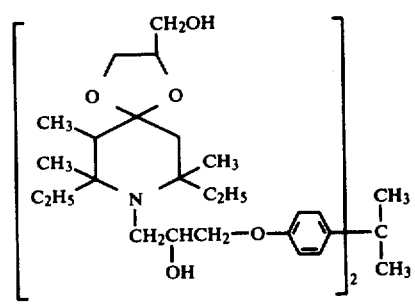 203.
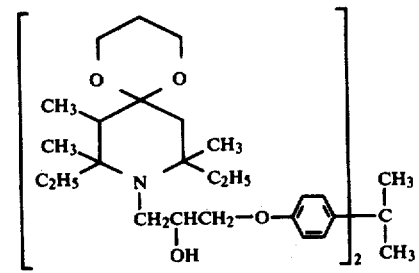 204.
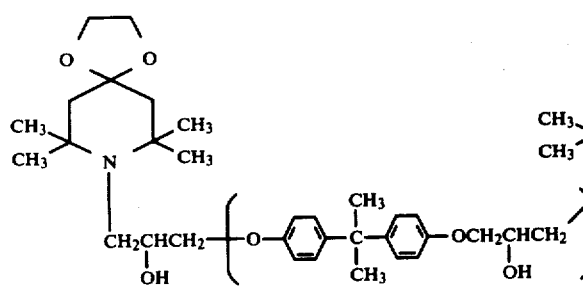 205.
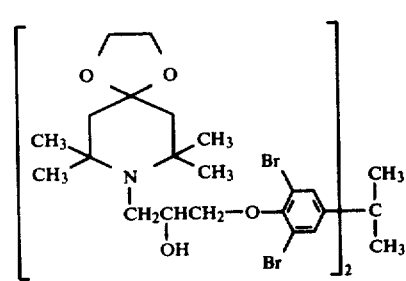 206.
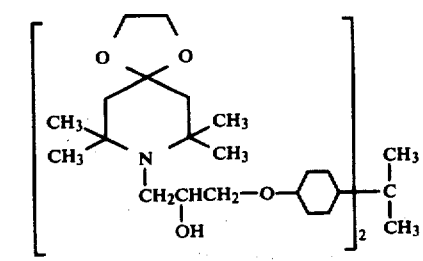 207.
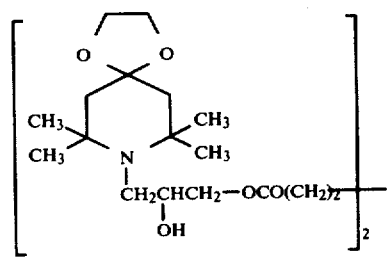 208.
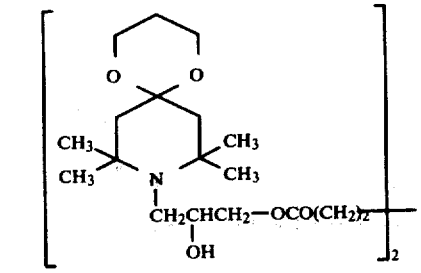 209.

-continued
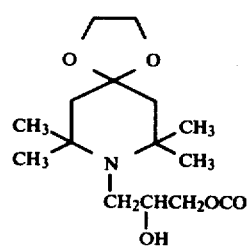 210. 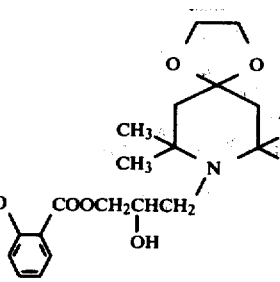 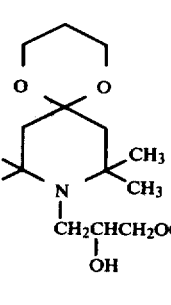 211. 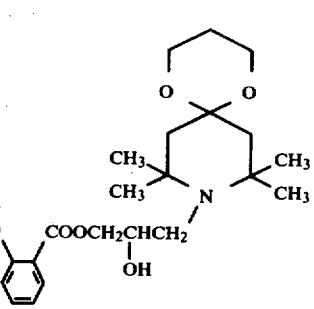
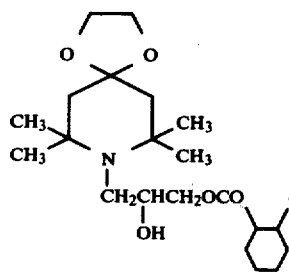 212. 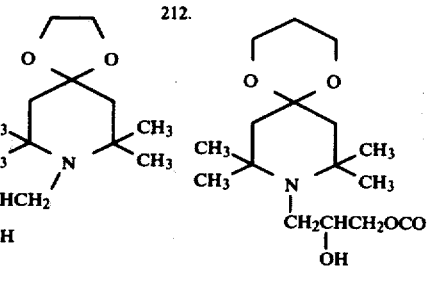 213. 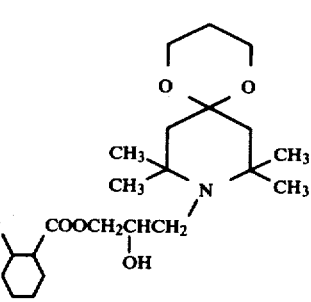
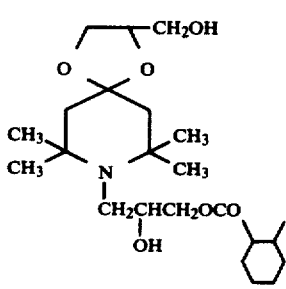 214. 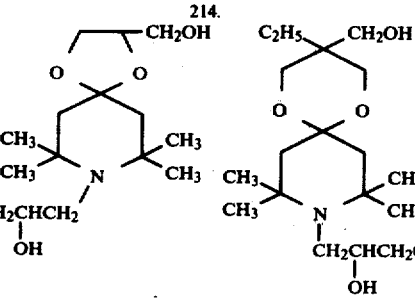 215. 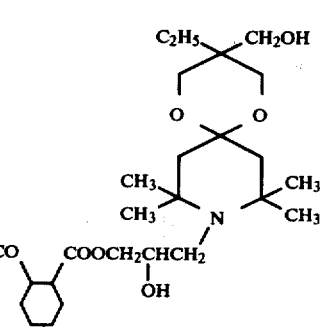
216.
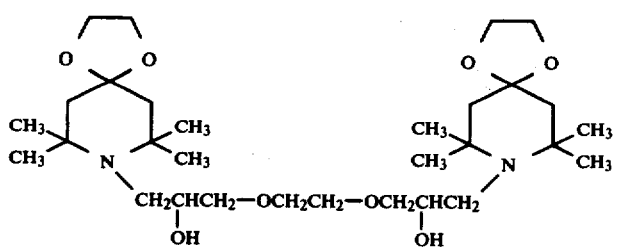
217.
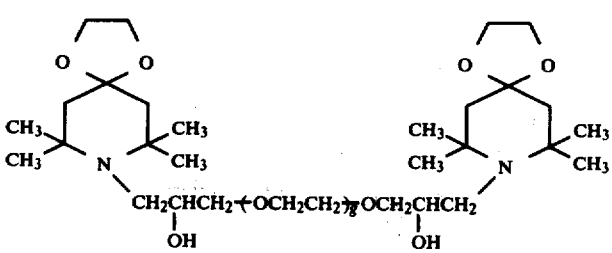

-continued
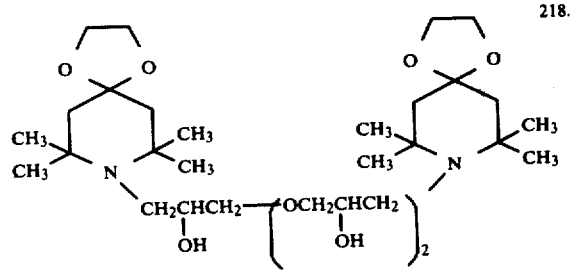 218.
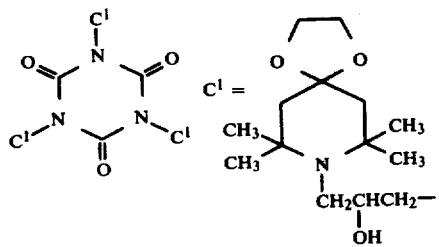 219.
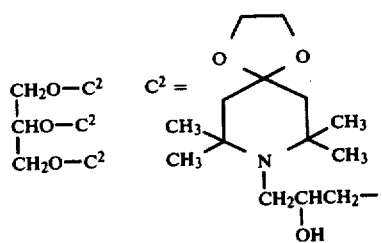 220.
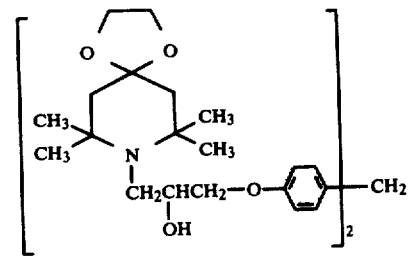 221.
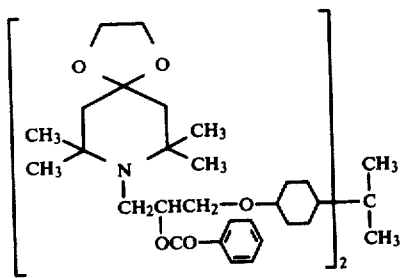 222.
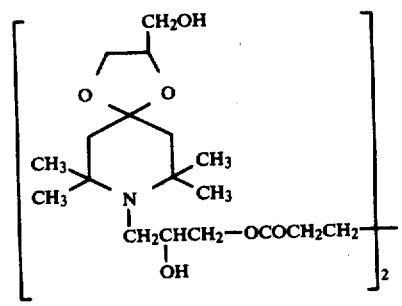 223.
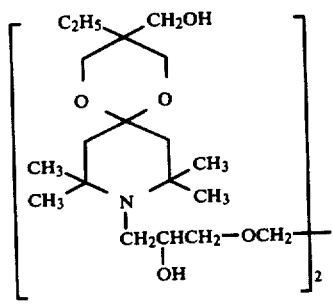 224.
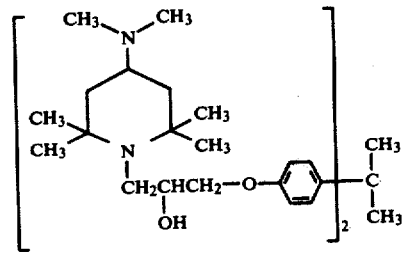 225.
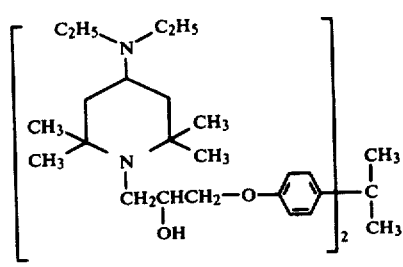 226.
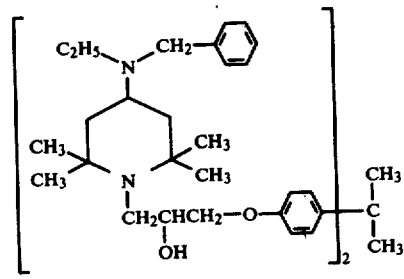 227.

-continued
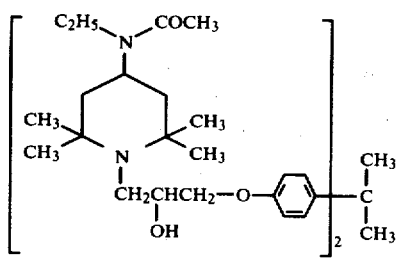 228.
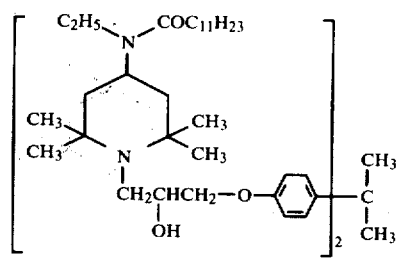 229.
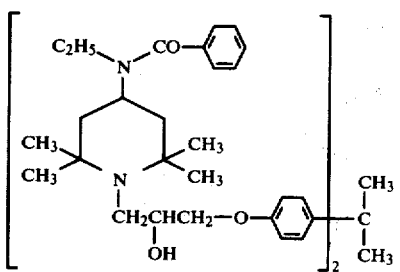 230.
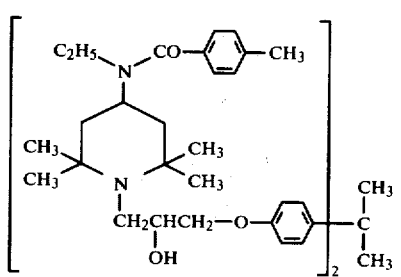 231.
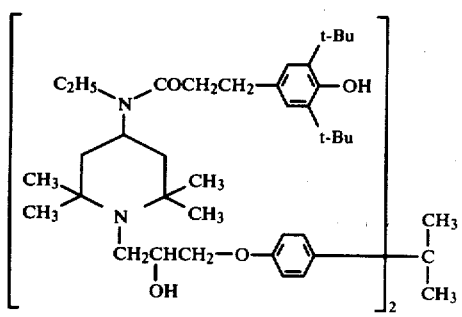 232.
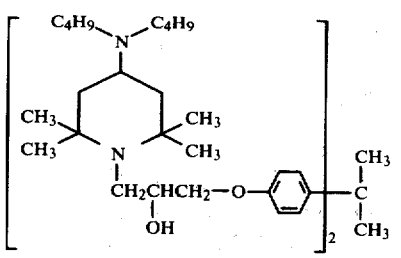 233.
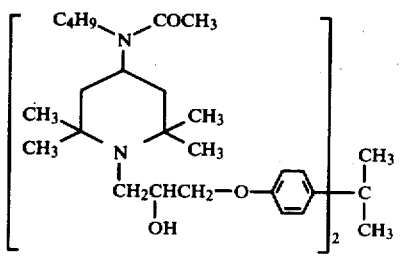 234.
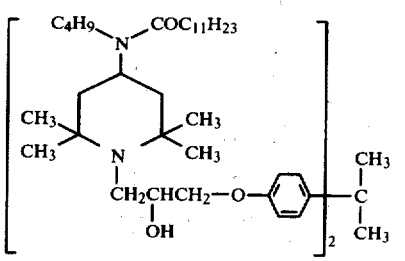 235.
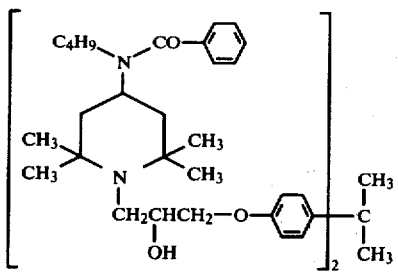 236.
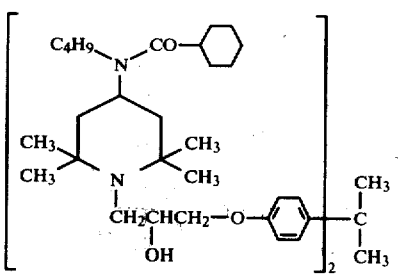 237.

-continued
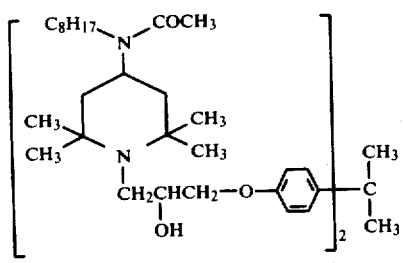 238.
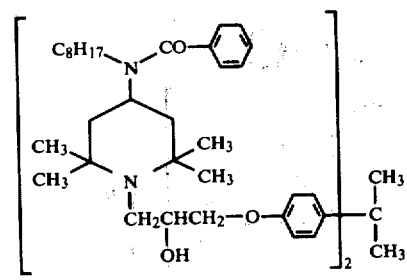 239.
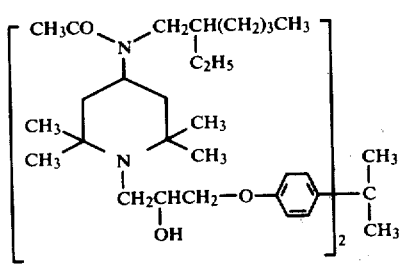 240.
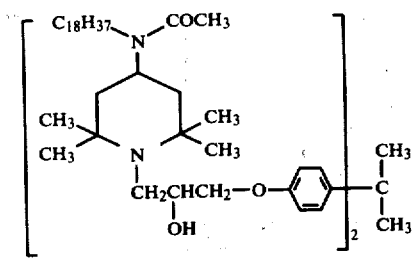 241.
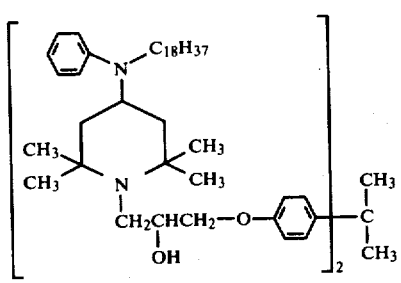 242.
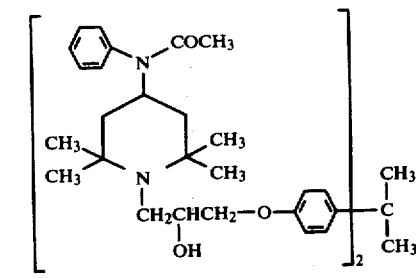 243.
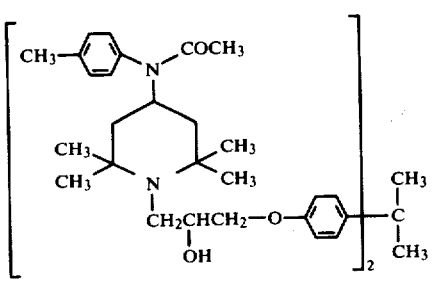 244.
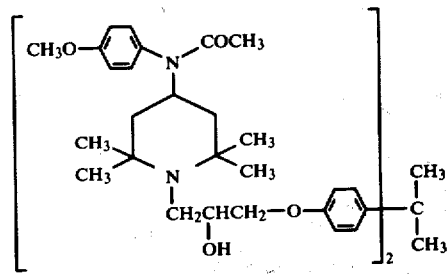 245.
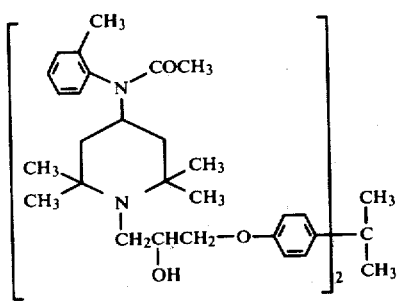 246.
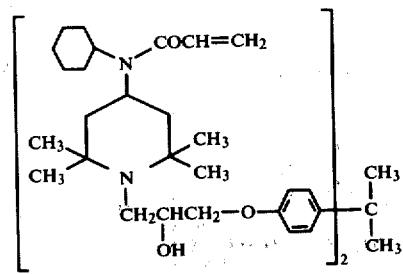 247.

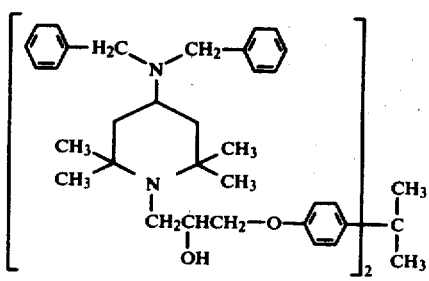 248.
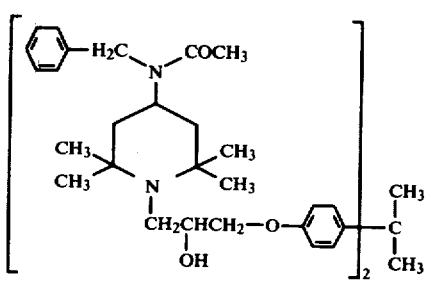 249.
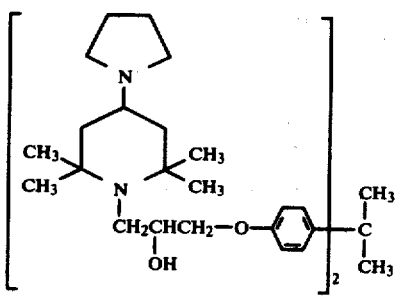 250.
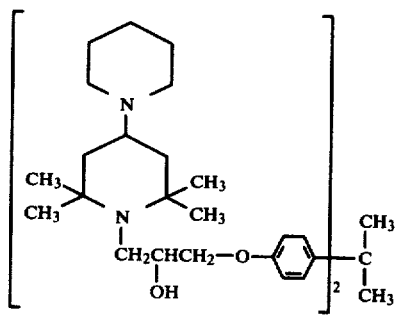 251.
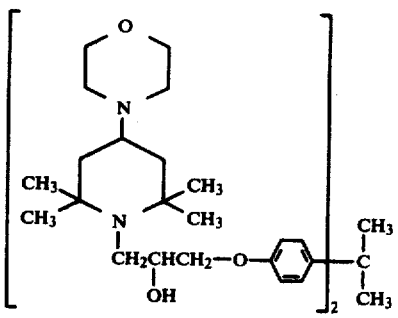 252.
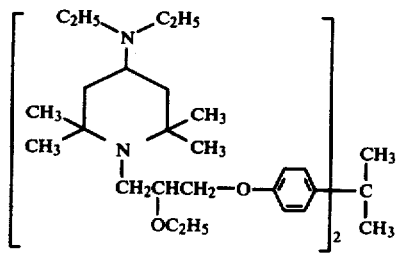 253.
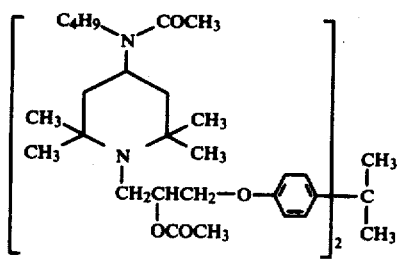 254.
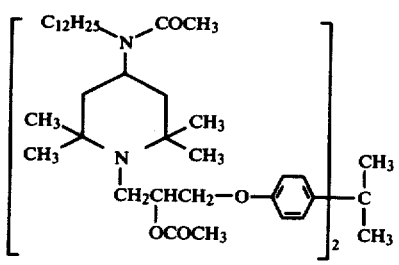 255.
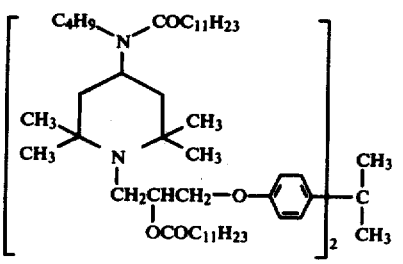 256.
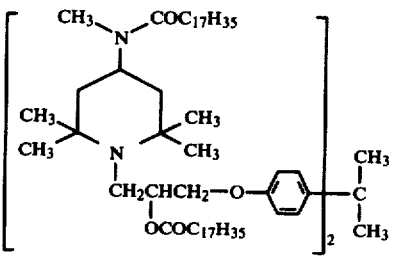 257.

-continued
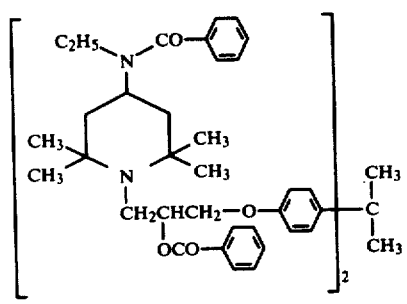 258.
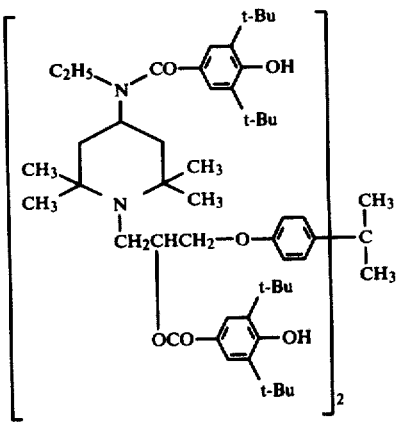 259.
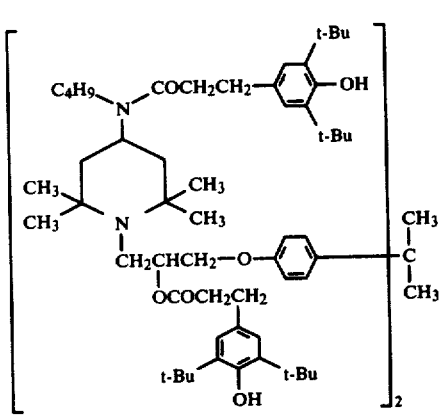 260.
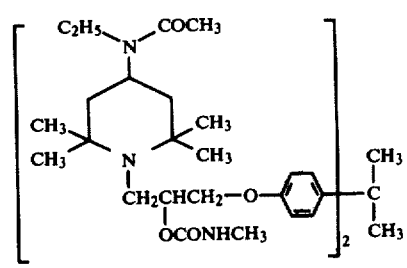 261.
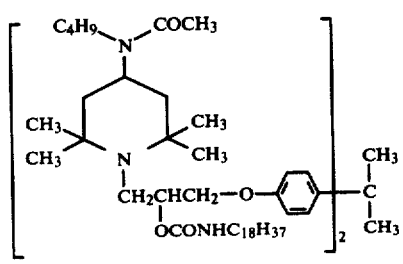 262.
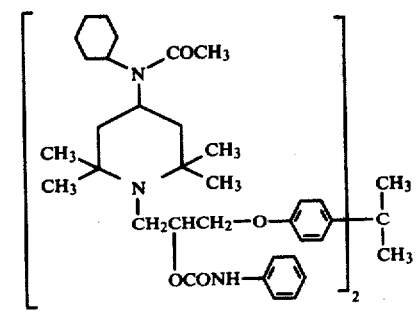 263.
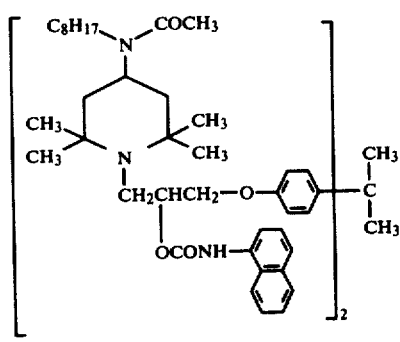 264.
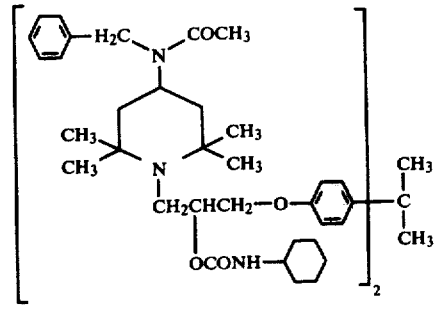 265.

-continued
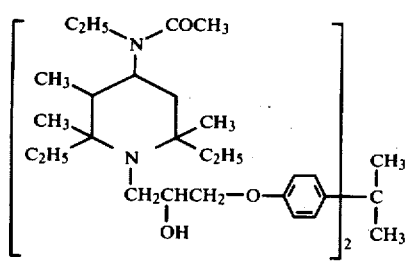 266.
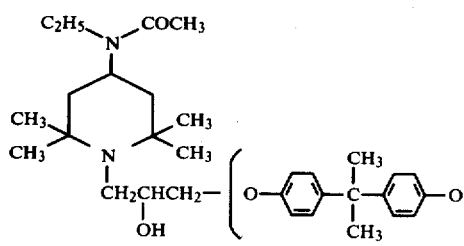 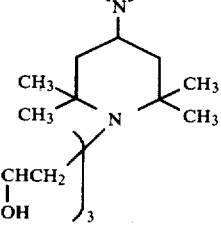 267.
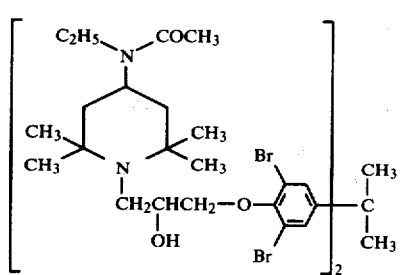 268. 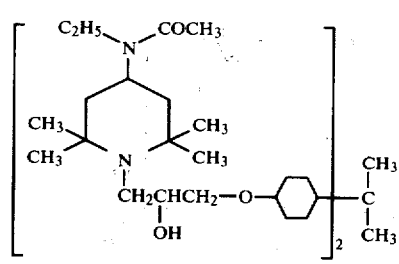 269.
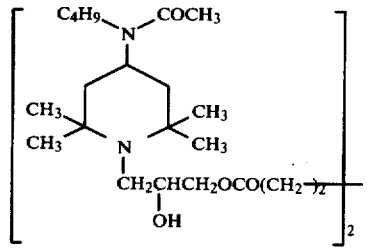 270. 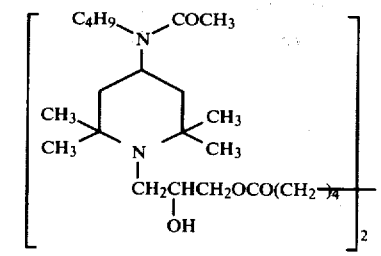 271.
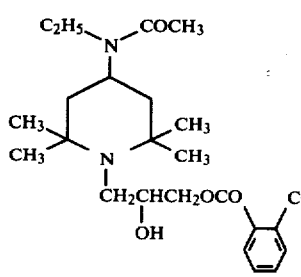 272. 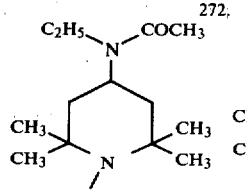 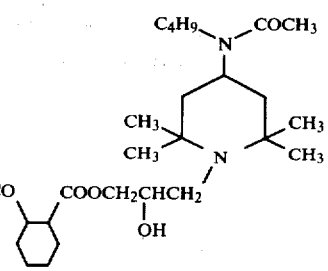 273.
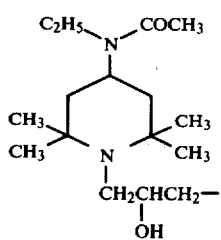 274. 275.

-continued
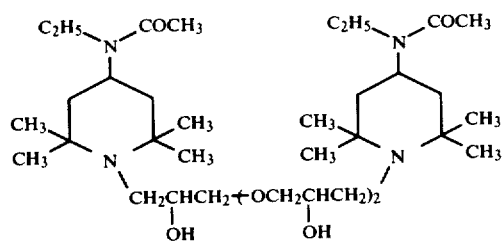
276.
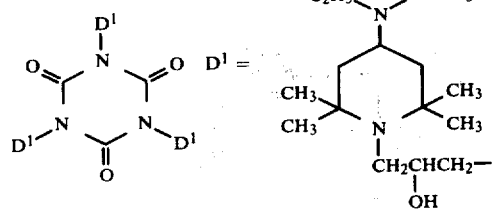
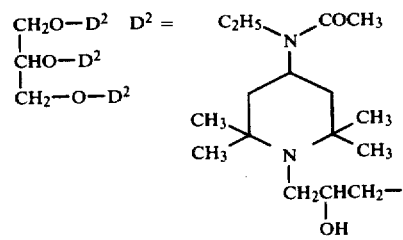
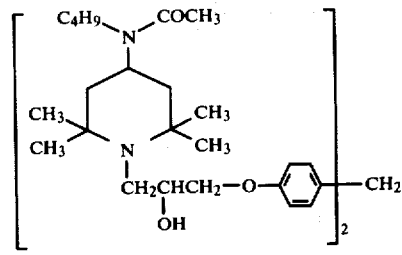
277.
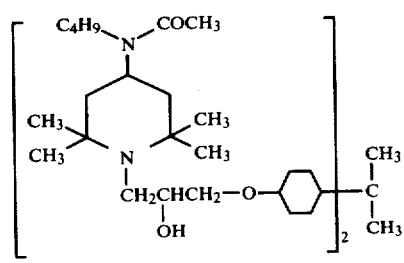
278.
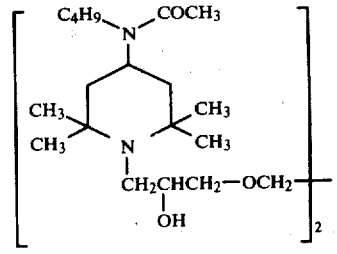
279.
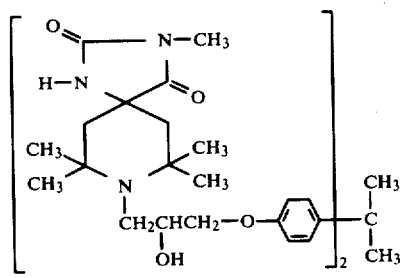
280.
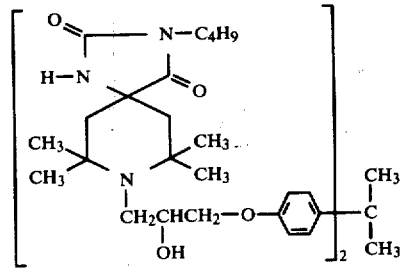
281.
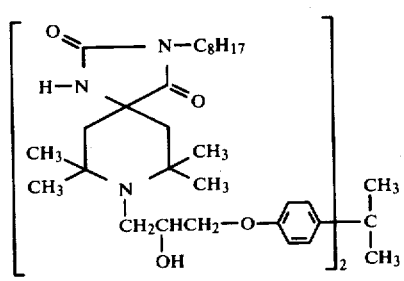
282.
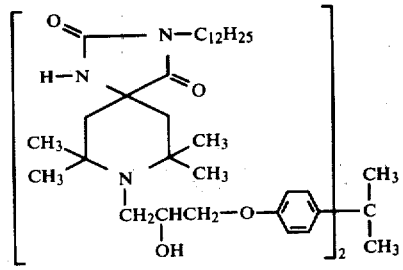
283.
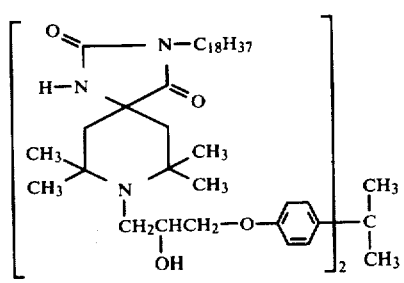
284.
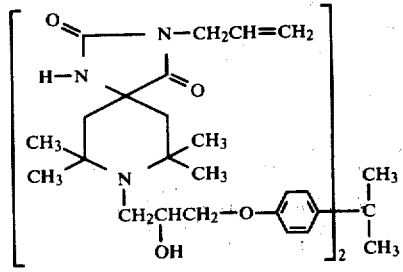
285.
286.
287.

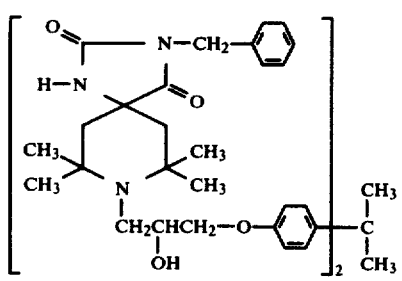 288.
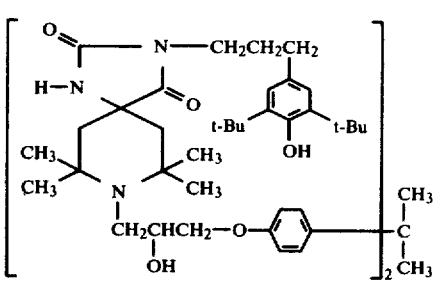 289.
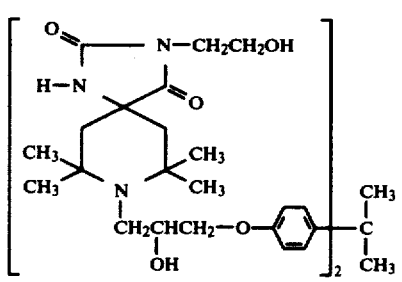 290.
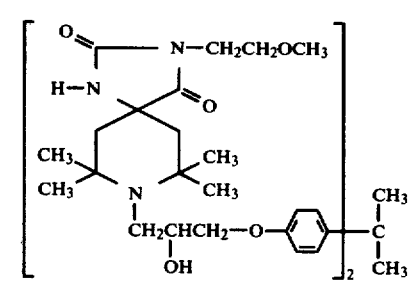 291.
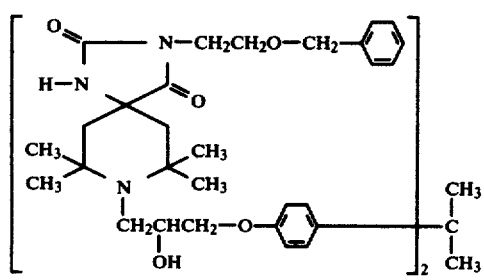 292.
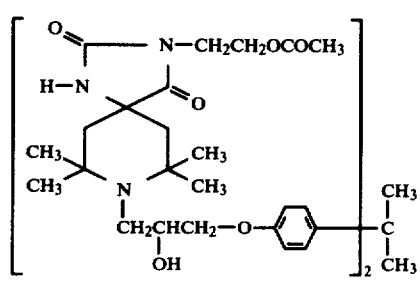 293.
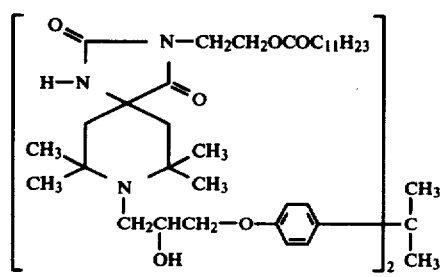 294.
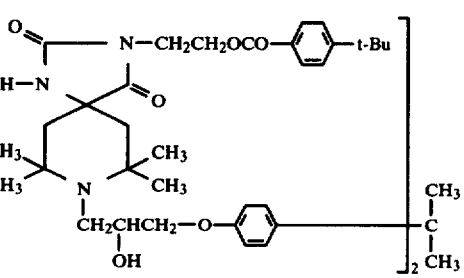 295.
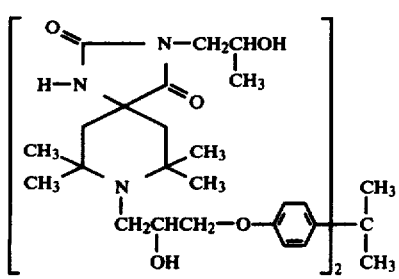 296.
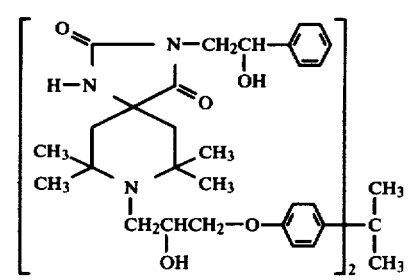 297

-continued
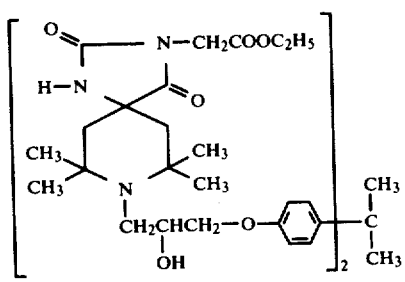 298.
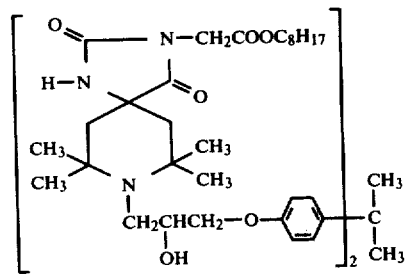 299.
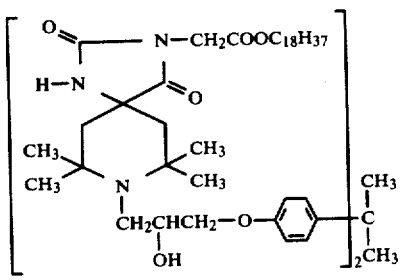 300.
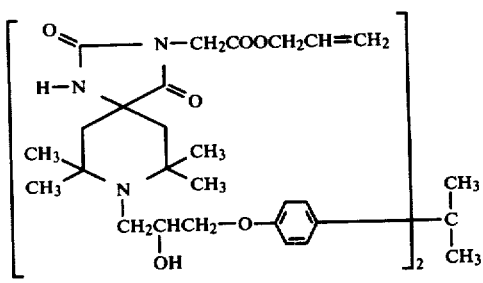 301.
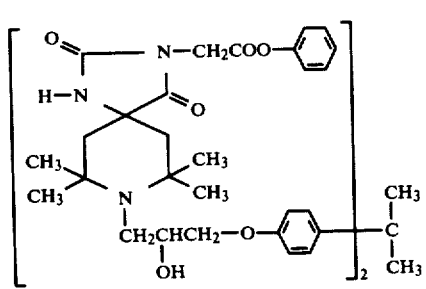 302.
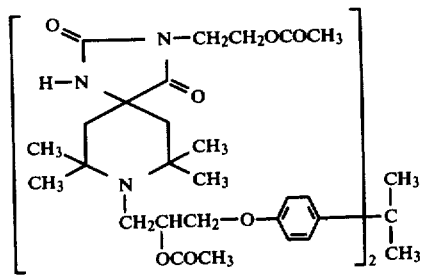 303.
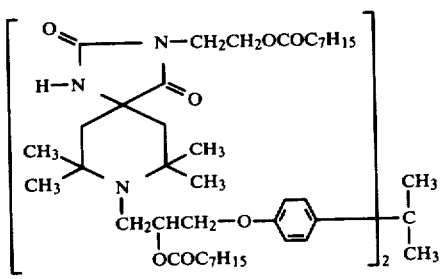 304.
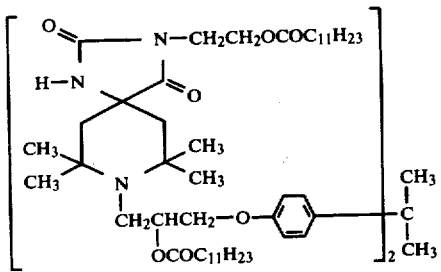 305.
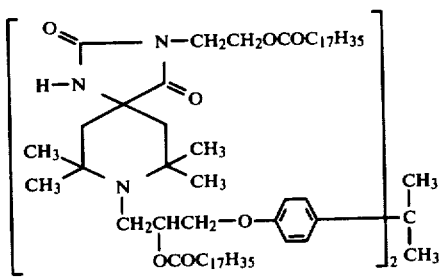 306.
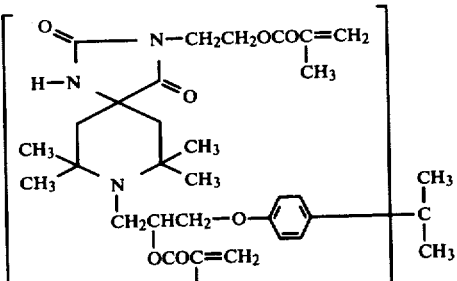 307.

-continued
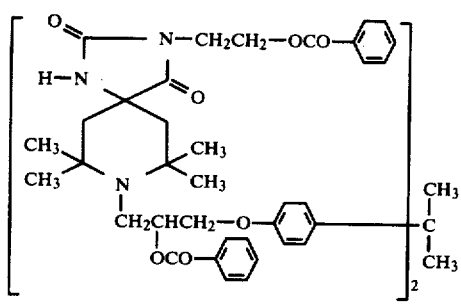 308.
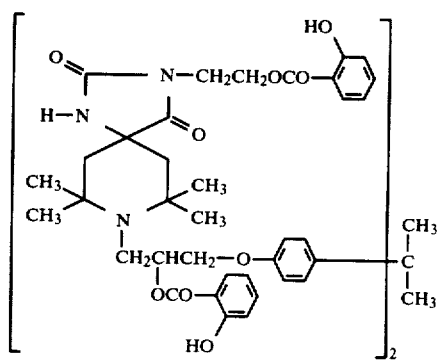 309.
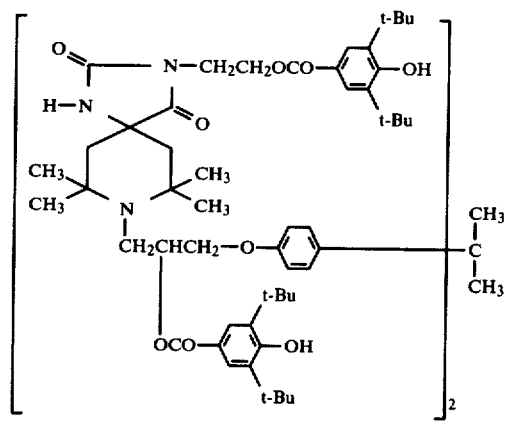 310.
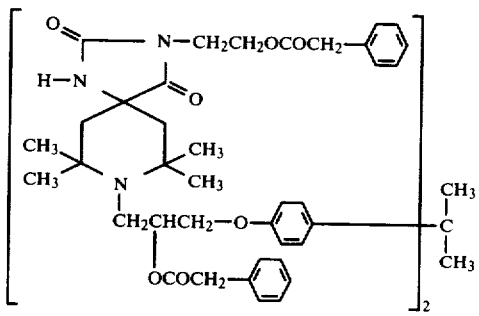 311.
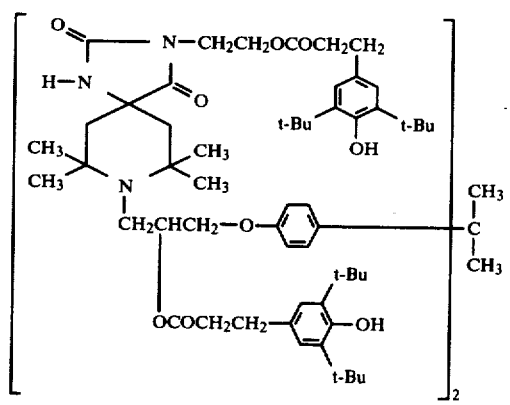 312.
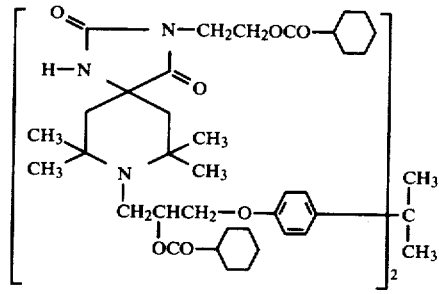 313.
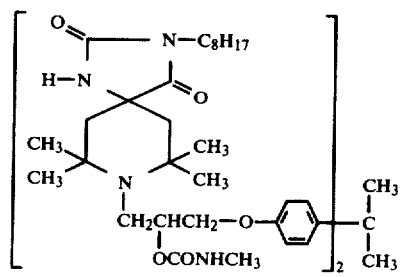 314.
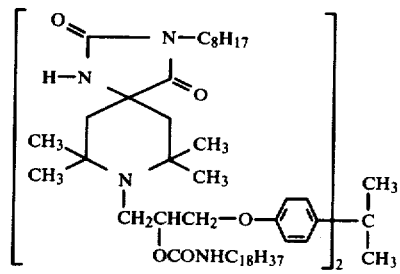 315.

-continued
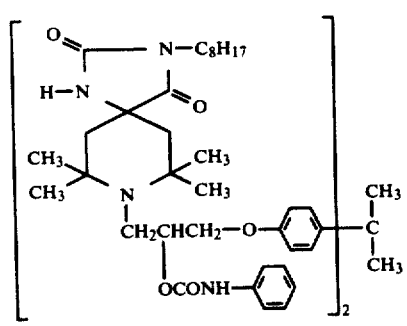 316.
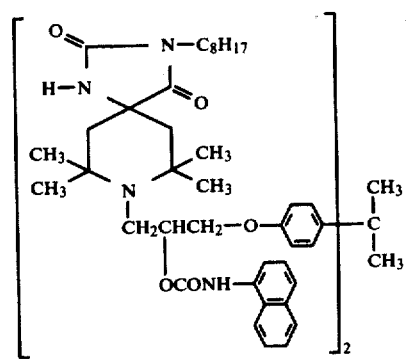 317.
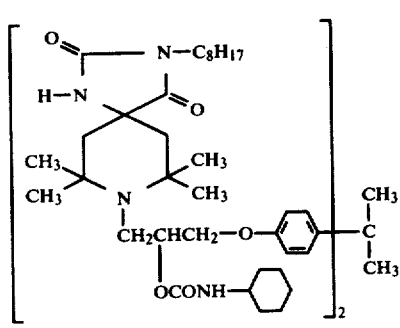 318.
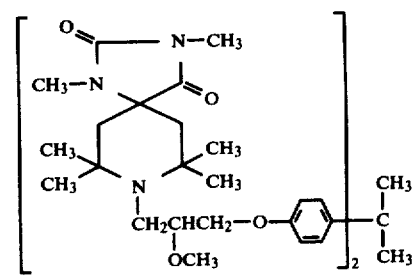 319.
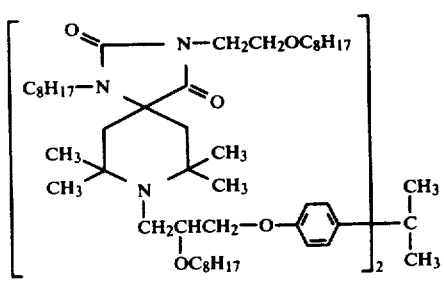 320.
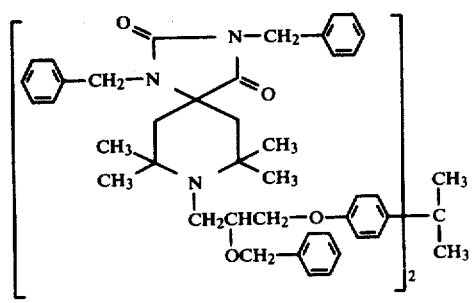 321.
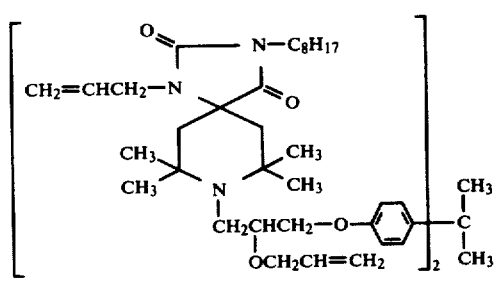 322.
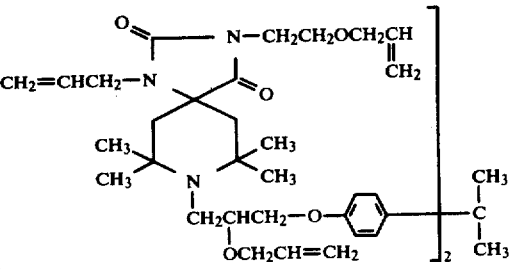 323.
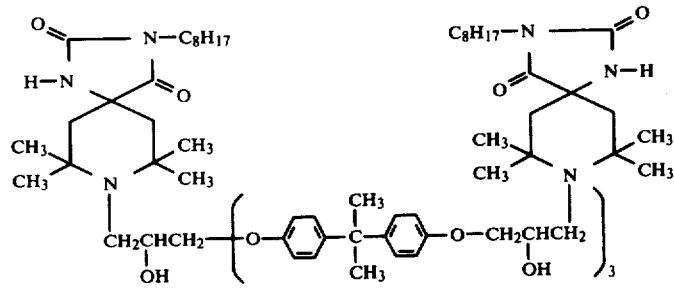 324.

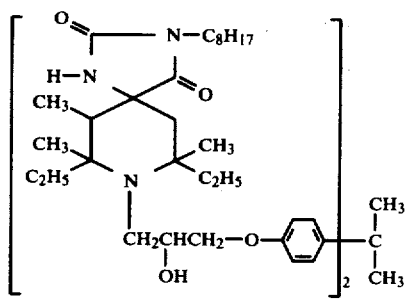 325.
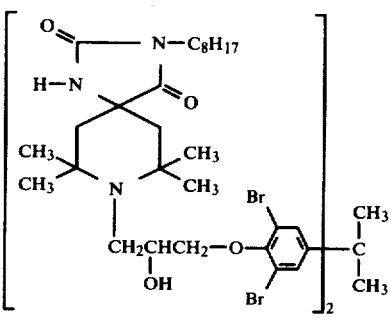 326.
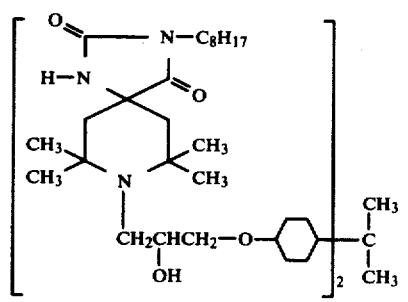 327.
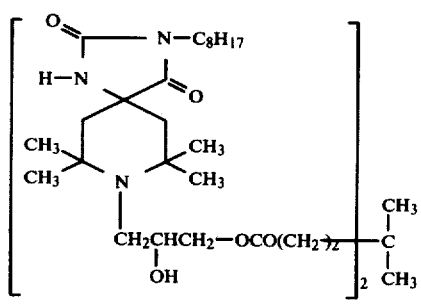 328.
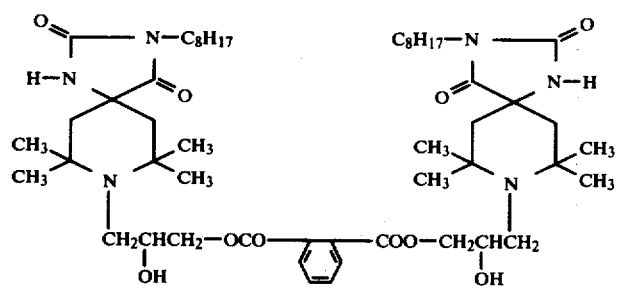 329.
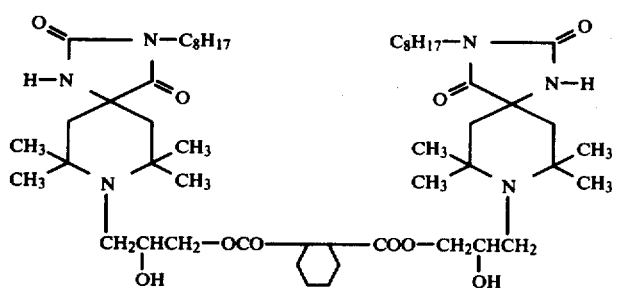 330.
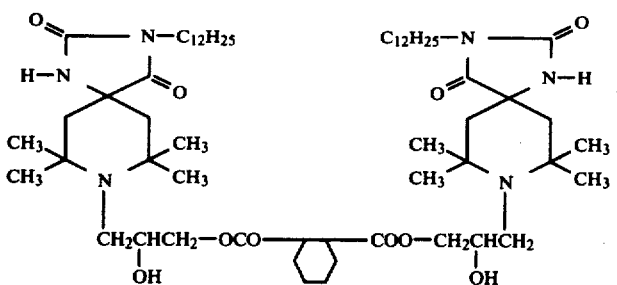 331.

-continued
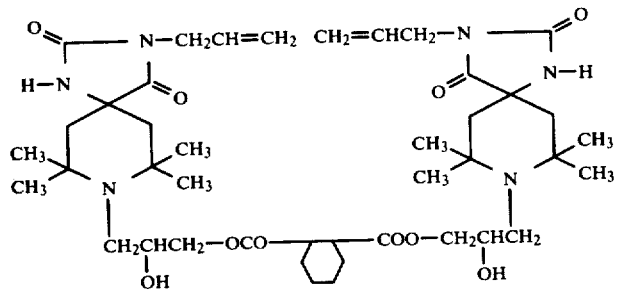 332.
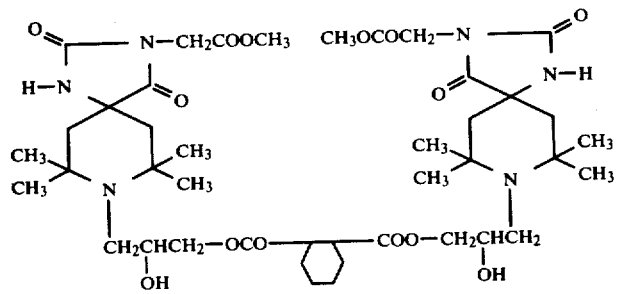 333.
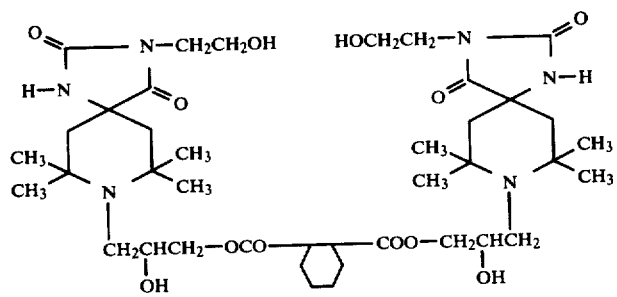 334.
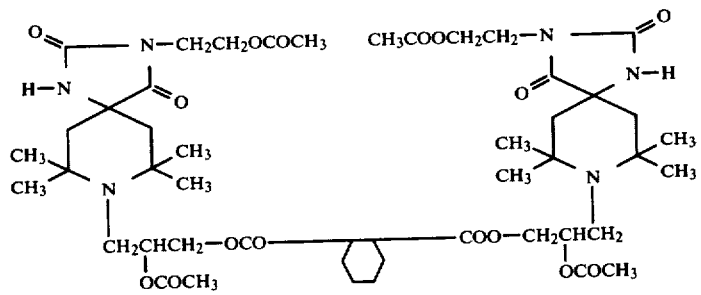 335.
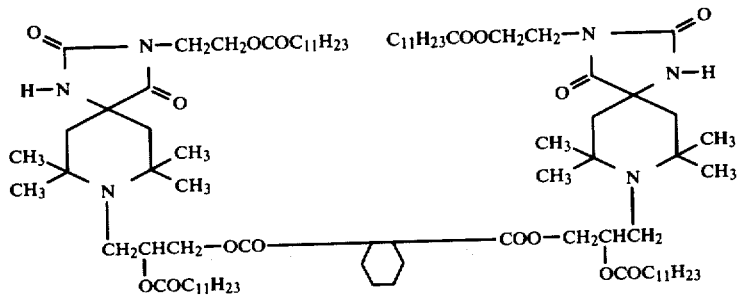 336.

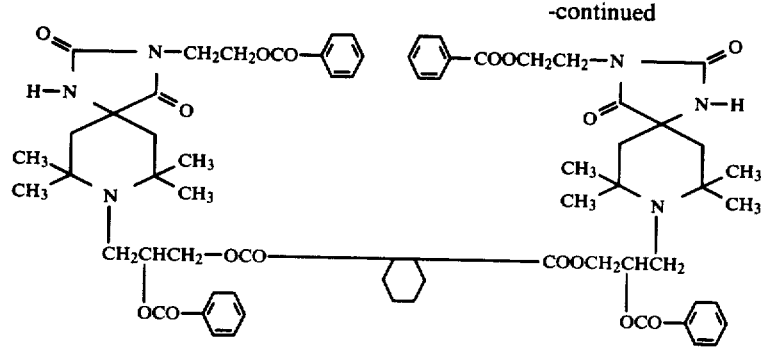
337.
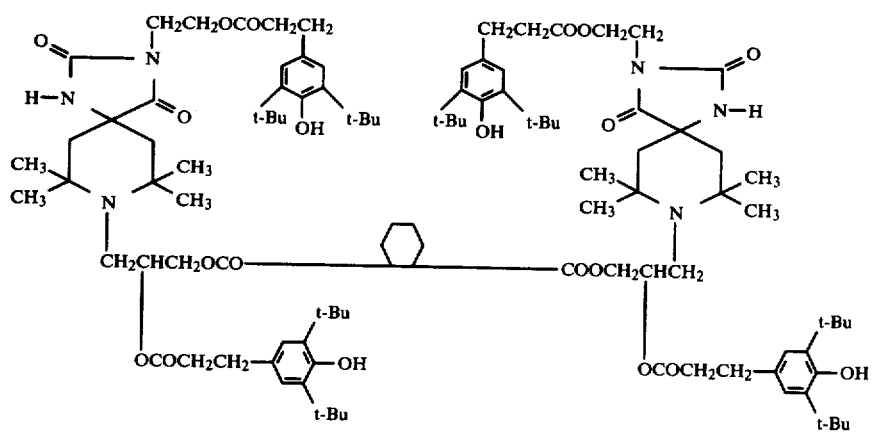
338.
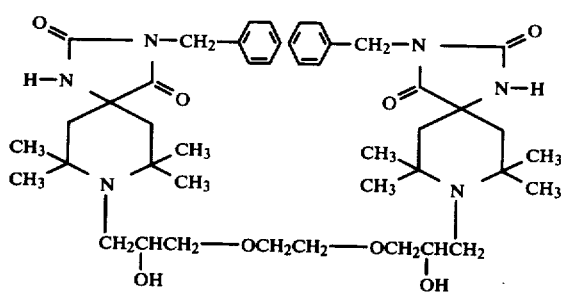
339.
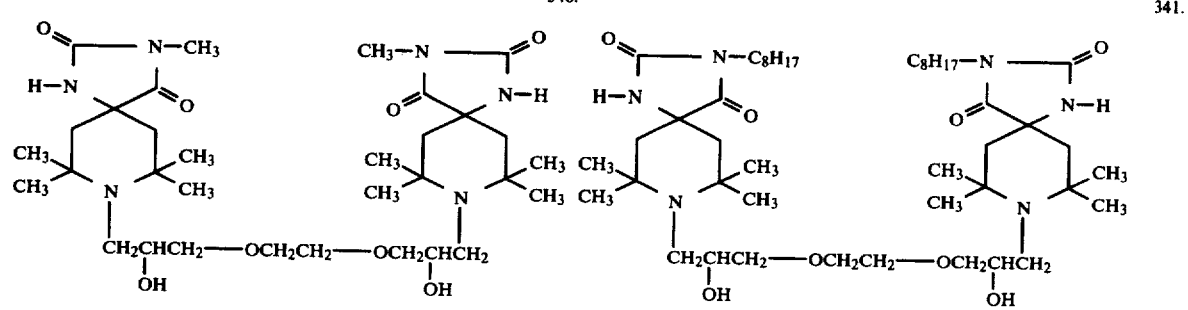
340.    341.
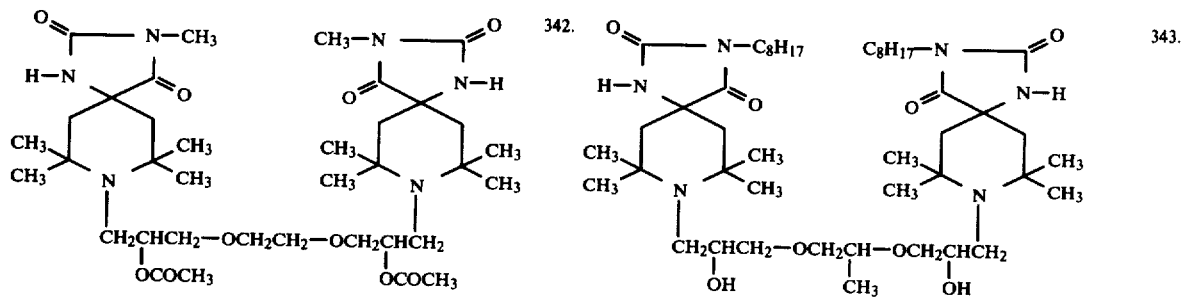
342.    343.

-continued
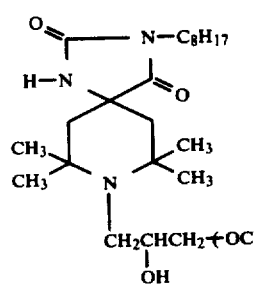 344. 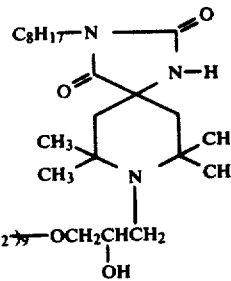 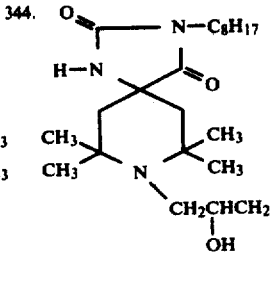 345. 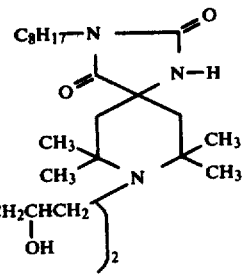
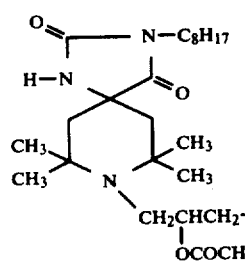 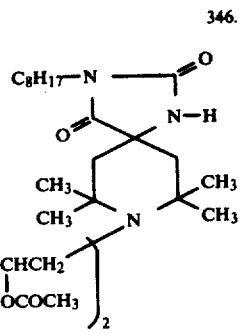 346. 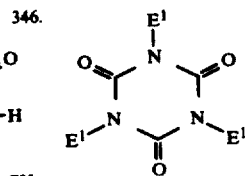 347. 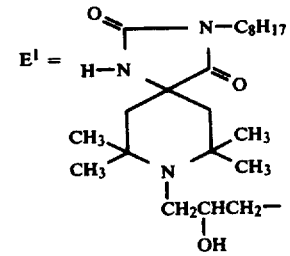
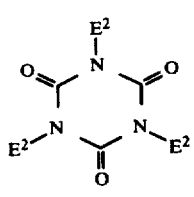 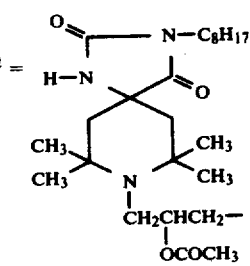 348. 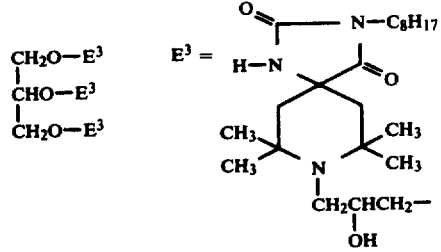 349.
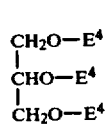 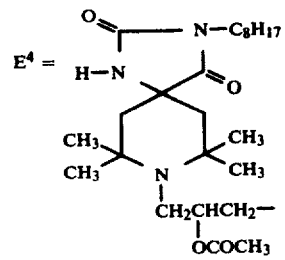 350. 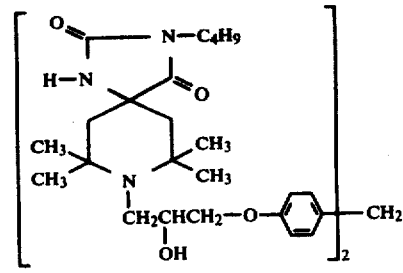 351.
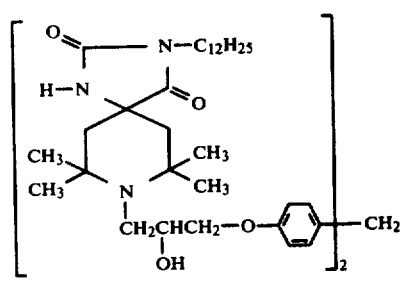 352. 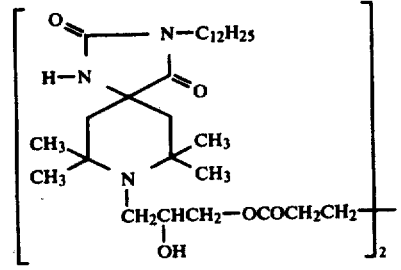 353.

-continued

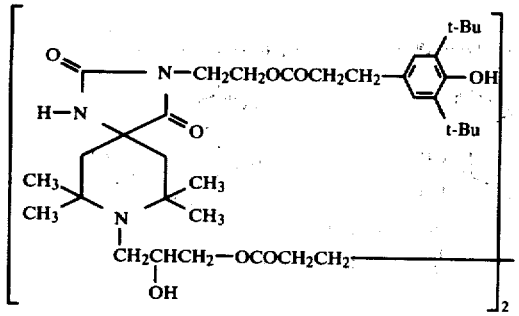
354.

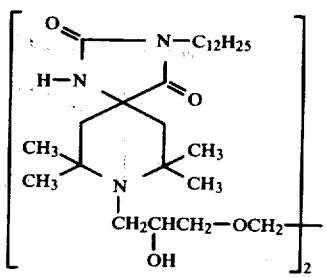
355.

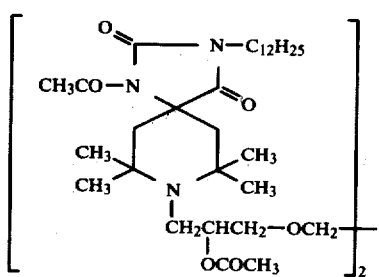
356.

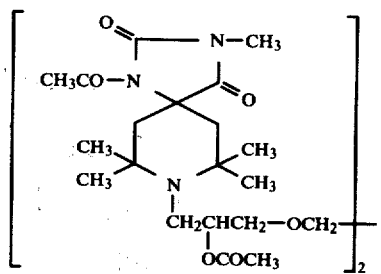
357.

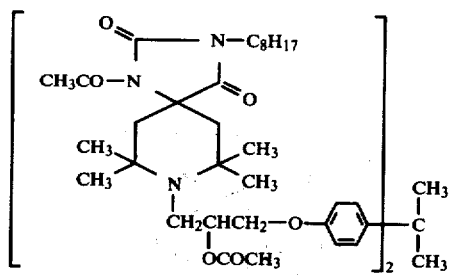
358.

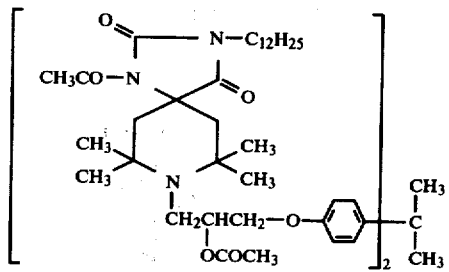
359.

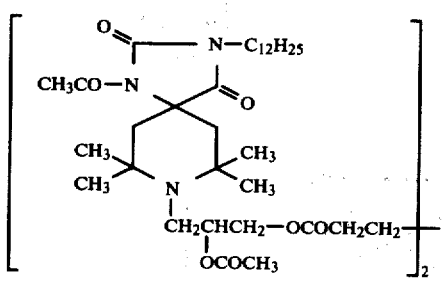
360.

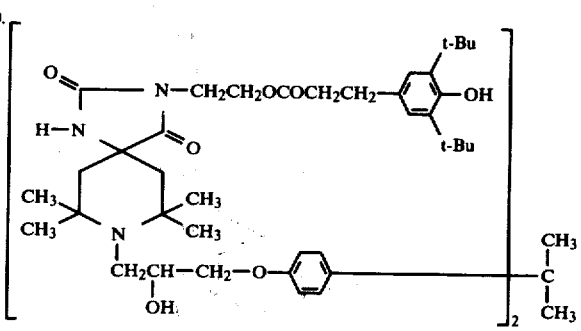
361.

The piperidine derivatives of formula (I) and acid addition salts thereof may be prepared by any one of the following methods, which can be performed under per se known conditions.

METHOD 1

Compounds of formula (I) in which Z in the group represented by Y represents a hydrogen atom may be prepared by reading a compound of formula (VI):

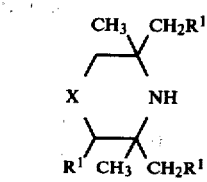
(VI)

with one of the following epoxy compounds:

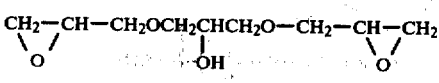

-continued

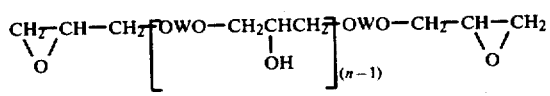

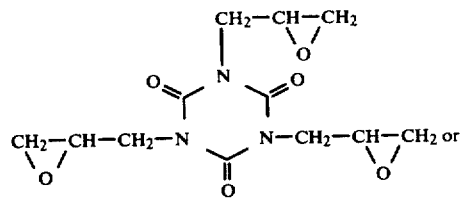

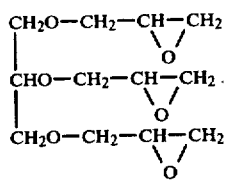

Preparation of the compounds of formula (VI) used as starting materials is described in U.S. Patent Specifications No. 3,840,494, No. 3,992,390, No. 3,790,525, No. 3,899,464, No. 3,839,273, No. 3,639,409, No. 3,705,126 and No. 3,975,462, British Patent Specification No. 1,417,835, Japanese Patent Publication No. 46-31733, Japanese Patent Applications No. 49-60337 and No. 49-72332, as laid open to public inspection, and German Offenlegungsschriften No. 2,621,841, No. 2,623,422, No. 2,621,855, No. 2,621,870 and No. 2,623,464

The reaction is preferably carried out by heating the compound of formula (VI) with the epoxy compound corresponding to the group Y which is desired to introduce, preferably at a temperature of from 50° to 180° C. The compound of formula (VI) is preferably employed in an amount slightly in excess of the stoichiometric amount. The reaction may be carried out in the presence or absence of an inert organic solvent and, where a solvent is employed, its nature is not critical, provided that it has no adverse effect upon the reaction. Examples of suitable solvents include: ethers, such as dioxan and diethylene glycol dimethyl ether; N,N-dialkylamides, such as N,N-dimethylformamide and N,N-dimethylacetamide; aromatic hydrocarbons, such as benzene, toluene and xylene; chlorinated aromatic hydrocarbons, such as chlorobenzene and p-dichlorobenzene; alcohols, such as methanol, ethanol, n-butanol, t-butanol and n-octanol; and aqueous alcohols, particularly aqueous methanol and aqueous ethanol. Of these solvents, alcohols and aqueous alcohols are preferred.

METHOD 2

It is also possible to prepare compounds of formula (I) in which Z of the group Y represents a hydrogen atom and W represents one of the groups of formula

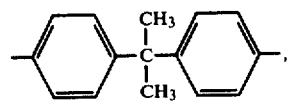

-continued

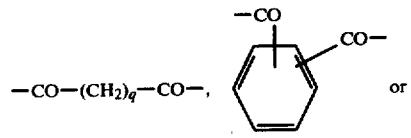

and n is 1 by reacting a compound of formula

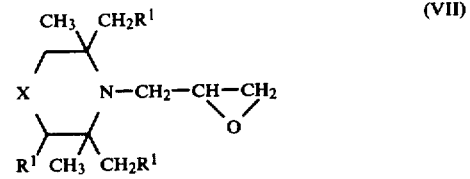

with Bisphenol A or with the corresponding dicarboxylic acid.

The compound of formula (VII) may be prepared by reacting the compound of formula (VI) (described under Method 1) with epichlorohydrin according to the method described in U.S. Patent Specification No. 3,941,774. The reaction is preferably carried out by heating the compound of formula (VII), preferably in a slight stoichiometric excess, with Bisphenol A or with the dicarboxylic acid, preferably at a temperature of from 50° to 180° C. and in the presence or absence of an inert organic solvent. Examples of solvents which can be employed include: ethers, such as dioxan and diethylene glycol diethyl ether; N,N-dialkylamides such as N,N-dimethylformamide and N,N-dimethylacetamide; aromatic hydrocarbons, such as benzene, toluene and xylene; chlorinated aromatic hydrocarbons, such as chlorobenzene and p-dichlorobenzene; and tertiary alcohols, such as t-butanol and t-pentanol.

Compounds in which Z of group Y represents any one of the substituents defined above (other than a hydrogen atom) can be prepared by introducing the required substituent into the corresponding compound wherein Z represents a hydrogen atom (and which can have been prepared by either of the methods described above) using the following methods.

METHOD 3

Compounds of formula (I) in which Z represents an alkyl group, an allyl group or a benzyl group may be prepared by reacting the corresponding compound in which Z represents a hydrogen group with an alkali metal compound, preferably with a strongly basic alkali metal compound (such as sodium hydride, butyllithium, sodium methoxide, sodium ethoxide or potassium t-butoxide) and then with a halogen compound in which the halogen atom is attached to the desired group Z. The reaction is preferably carried out in the presence of an inert organic solvent and at a temperature which may range from ambient to 130° C. Examples of suitable solvents are: aromatic hydrocarbons, such as benzene, toluene and xylene; ethers, such as tetrahydrofuran and dioxan; and N,N-dialkylamides, such as N,N-dimethylformamide and N,N-dimethylacetamide.

METHOD 4

Compounds in which Z represents a lower alkyl group, particularly methyl or ethyl, may be prepared by reacting the corresponding compound of formula (I) in which Z represents a hydrogen atom with a di(lower alkyl)sulphate. The reaction is preferably performed in the presence of an inert organic solvent or, if no organic solvent is employed, using an excess of the di(lower alkyl)sulphate.

Where a solvent is employed, it may be, for example; and aromatic hydrocarbon, such as benzene, toluene or xylene; a lower ketone, such as methyl ethyl ketone; or an ether, such as tetrahydrofuran or dioxan.

The reaction is preferably carried out in the presence of an alkali metal hydroxide or carbonate (such as sodium hydroxide, potassium hydroxide or potassium carbonate) and is preferably effected at a temperature which may range from ambient temperature to 150° C.

Where any one of the following groups:
$R^2$;
$R^{18}$ when $R^3$ and $R^4$ together represent one of the groups

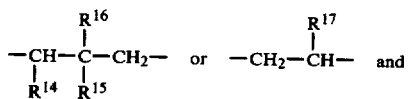

$R^{16}$ or $R^{17}$ represents the group $-CH_2OR^{18}$;
$R^{22}$, when $R^8$ represents the group $-CH_2CHR^{21}(OR^{22})$; and both $R^7$ and $R^{22}$
represents a hydrogen atom in the compound of formula (I) employed as starting material in this method, the alkylation, allylation or benzylation of this method may result in compounds in which $R^2$, $R^{18}$, $R^{22}$ or $R^7$ and $R^{22}$ are identical alkyl, allyl or benzyl groups with the group Z.

METHOD 5

Compounds of formula (I) in which Z represents an acyl group can be prepared by reacting the corresponding compound in which Z represents a hydrogen atom (and which may have been obtained by either of Methods 1 and 2) with a reactive derivative of a carboxylic acid corresponding to the desired acyl group. Examples of such reactive derivatives include acid halides, acid anhydrides, lower alkyl esters and benzothiazolyl thiol esters of the acid.

When an acid halide is employed as the reactive derivative, the reaction is preferably carried out in the presence of an acid-binding agent and in the presence of an inert organic solvent. Where a solvent is employed, its nature is not critical, provided that it has no adverse effect upon the desired reaction. Examples of suitable solvents are: aromatic hydrocarbons, such as benzene, toluene and xylene; halogenated aliphatic hydrocarbons, such as chloroform and trichloroethane; and ethers, such as diethyl ether, tetrahydrofuran and dioxan. Suitable acid-binding agents include: alkali metal hydroxides, such as sodium hydroxide and potassium hydroxide; alkali metal carbonates, such as sodium carbonate and potassium carbonate; and organic bases, such as triethylamine and pyridine. The reaction is preferably carried out at a temperature from 0° C. to 130° C.

When the reactive derivative employed is a lower alkyl ester of the acid, the reaction is preferably carried out in the presence of a strong base and of an inert organic solvent. The nature of the solvent is not critical, provided that it has no adverse effect upon the desired reaction; examples of suitable solvents are: aromatic hydrocarbons, such as benzene, toluene and xylene; and aliphatic hydrocarbons, such as n-heptane, n-octane and isooctane. Suitable strong bases include, for example: strongly basic alkali metal compounds, such as sodium methoxide, sodium ethoxide, potassium hydroxide and lithium amide; and titanic acid compounds, particularly organic esters of titanic acid, such as tetraisopropyl titanate and tetraisobutyl titanate. It is preferred that the reaction should be carried out with heating, preferably at a temperature from 80° C. to 180° C.

Where the reactive derivative is an acid anhydride, the reaction is preferably carried out in the presence of an inert organic solvent or in the absence of a solvent but using an excess of acid anhydride. Where a solvent is employed, it is preferably selected from: aromatic hydrocarbons, such as benzene, toluene and xylene; and ethers, such as dioxan, tetrahydrofuran and diethylene glycol dimethyl ether. The reaction temperature may preferably be any temperature from ambient to 160° C.

In this process, if the starting material is a compound in which any one of the following groups represents a hydrogen atom:
$R^2$
$R^{18}$, when $R^3$ and $R^4$ together represent one of the groups

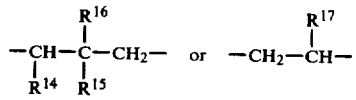

and $R^{16}$ or $R^{17}$ represents $-CH_2OR^{18}$;
$R^{22}$, when $R^8$ represents the group $-CH_2CHR^{21}(OR^{22})$; then the reaction of such a starting material in accordance with this method may produce a compound in which Z and the above groups are identical acyl groups.

METHOD 6

Compounds of formula (I) in which Z represents an N-substituted carbamoyl group of formula $-CONR^9R^{10}$ may be prepared by reacting the corresponding compound in which Z represents a hydrogen atom with a substituted carbamoyl halide, e.g. a compound of formula Cl—$CONR^9R^{10}$. The reaction is preferably carried out in the presence of an acid-binding agent and the presence of an inert organic solvent. Where a solvent is employed, it is preferably an ether (such as tetrahydrofuran or dioxan) or an aromatic hydrocarbon (such as benzene or toluene). The acid-binding agent is preferably an organic base, such as triethylamine, N,N-diethylaniline or pyridine. The reaction is preferably carried out at a temperature from −10° C. to 120° C.

METHOD 7

Compounds in which Z represents a group of formula $-CONHR^{10}$ can be produced by reacting the corresponding compound in which Z is a hydrogen atom with an isocyanate of formula $R^{10}NCO$. The reaction may be carried out in the presence or absence of an inert organic solvent. Where a solvent is employed, its nature is not critical, provided that it has no adverse effect upon the desired reaction. Examples of suitable solvents are aromatic hydrocarbons (such as benzene, toluene and xylene) and ethers (such as tetrahydrofuran and dioxan). The reaction is preferably carried out at a temperature of from 50° C. to 160° C.

Where the starting material is a compound in which either $R^2$ or $R^{18}$ (when $R^3$ and $R^4$ together represent one of the groups

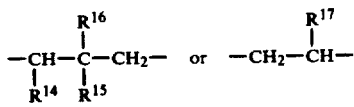

and $R^{16}$ or $R^{17}$ represents the group $—CH_2OR^{18}$) represents a hydrogen atom, the compound produced may be one in which both Z and $R^2$ or $R^{18}$ are identical N-substituted carbamoyl groups; this applies to both Methods 6 and 7.

METHOD 8

Compounds of formula (I) in which Z represents a group of formula

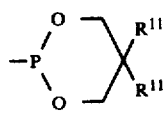

or $—P(OR^{12})_2$ may be prepared by reacting the corresponding compound in which Z represents a hydrogen atom with a phosphorus halide, e.g. a compound of formula

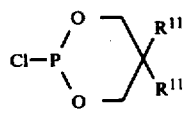

or $Cl—P(OR^{12})_2$. The reaction is preferably carried out in the presence of a base and of an inert organic solvent. Where a solvent is employed, its nature is not critical, provided that it has no adverse effect upon the reaction; examples of suitable solvents include: ethers, such as dioxan, tetrahydrofuran and diethyl ether; aliphatic, alicyclic or aromatic hydrocarbons, such as n-hexane, cyclohexane, benzene and toluene; and N,N-dialkylamides, such as N,N-dimethylformamide and N,N-dimethylacetamide. The base is preferably a tertiary amine, such as triethylamine or N,N-diethylaniline. The reaction is preferably carried out at a temperature of from −10° C. to 80° C.

If the compound employed as starting material is one in which both Z and $R^2$ represent hydrogen atoms, the product may be a compound in which both Z and $R^2$ represent identical groups of formula

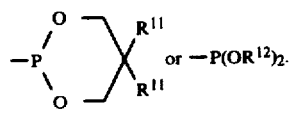

METHOD 9

Compounds of formula (I) in which Z represents any one of the defined substituents other than a hydrogen atom and in which:
X represents the group —CH(OH)—,
$R^3$ and $R^4$ of X together represent one of the groups

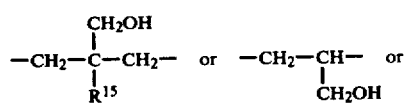

$R^8$ represents the group

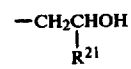

may be prepared by preparing the corresponding compound in which z represents a hydrogen atom (which may be done by either of Methods 1 and 2), protecting the hydroxy group in the above groups X, $R^3$ and $R^4$ or $R^8$ by conventional means (e.g. by tetrahydropyranyl etherification or p-nitrobenzoylation) and then converting the hydrogen atom represented by the group Z to the desired substituent group by any one of Methods 3 to 8. The protecting group may then be removed from the hydroxy group of X, $R^3$ and $R^4$ or $R^8$. If desired, the resulting compound can then be subjected to any of Methods 3 to 8 to convert the hydroxy group of X, $R^3$ and $R^4$ or $R^8$ to the desired group different from the group Z.

METHOD 10

Compounds of formula (I) in which $R^7$ represents an acetyl group and Z represents a hydrogen atom or any other of the groups defined above may be prepared by reacting the corresponding compound in which $R^7$ represents a hydrogen atom with, for example, acetic anhydride. When the starting material is a compound in which Z also represents a hydrogen atom, the product obtained may be a compound in which both $R^7$ and Z represent acetyl groups.

METHOD 11

Acid addition salts of compounds of formula (I) may be prepared by neutralising the compound of formula (I) with a suitable acid, preferably in the presence of an inert organic solvent or a mixture thereof with water.

The piperidine derivatives of formula (I) and acid addition salts thereof are useful for stabilizing polymers, particularly synthetic polymers against the deterioration caused by heat and/or light. They are highly effective stabilizers and are less volatile upon the application of heat than conventional piperidine derivatives used as light stabilizers. Accordingly, the invention further provides a polymeric composition comprising a polymer and, as stabilizer, a piperidine derivative of formula (I) or an acid addition salt thereof. Syntheticpolymers which can be stabilized in this way include:
olefin and diene polymers
including homopolymers of olefins and dienes (e.g. low-density, high-density and cross-linked polyethylenes, polypropylene, polyisobutylene, polymethylbutenes, polymethylpentene-1, polyisoprene and polybutadiene), mixtures of such homopolymers (e.g. mixtures of polypropylene and polyethylene, polypropylene and polybutene-1, or polypropylene and polyisobutylene), and copolymers of olefins and dienes (e.g. ethylene/propylene copolymers, propylene/butene-1 copolymers, propylene/isobutylene copolymers, ethylene/butene-1 copolymers, and terpolymers of ethylene and propylene with dienes such as hexadiene, dicyclopentadiene or ethylidene norbornene);

styrene polymers including polystyrene, copolymers of styrene and of α-methylstyrene (e.g. styrene/butadiene copolymers, styrene/acrylonitrile copolymers, styrene/acrylonitrile/methylmethacrylate copolymers, styrene/acrylonitrile/acrylic ester copolymers, styrene/acrylonitrile copolymers modified with acrylic ester polymers to provide impact strength, and styrene polymers modified with ethylene/propylene/diene elastomers to provide impact strength), and graft copolymers of styrene (e.g. polymers in which styrene is grafted onto polybutadiene, and polymers in which styrene and acrylonitrile are grafted onto polybutadiene as well as mixtures thereof with the aforementioned styrene copolymers—commonly known as acrylonitrile/butadiene/styrene or ABS plastics);

halogenated vinyl and vinylidene polymers including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, and vinylidene chloride/vinyl acetate copolymers;

polymers derived from α,β-unsaturated acids and derivatives thereof, including polyacrylates and polymethacrylates, polyacrylic amides and polyacrylonitrile;

polymers derived from unsaturated alcohols and amines and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate, and polyallyl melamine, and copolymers thereof with other ethylenically unsaturated monomers (e.g. ethylene/vinyl acetate copolymers);

epoxy polymers including homopolymers and copolymers derived from epoxides (e.g. polyethylene oxide), and polymers derived from bis-glycidyl ethers;

polyacetals, polyalkylene oxides and polyphenylene oxides including polyoxymethylene, oxymethylene/ethylene oxide copolymers, polyoxyethylene, polypropylene oxide, polyisobutylene oxide and polyphenylene oxides;

polyurethanes and polyureas;
polycarbonates;
polysulphones;
polyamides and copolyamides derived from diamines and dicarboxylic acids and/or from aminocarboxylic acids or the corresponding lactams, including nylon-6, nylon-6,6, nylon-6,10, nylon-11 and nylon-12;

polyesters derived from dicarboxylic acids and dialcohols and/or from hydroxycarboxylic acids and the corresponding lactones, e.g. polyethylene glycol terephthalate and poly-1,4-dimethylol-cyclohexane terephthalate;

cross-linked polymers derived from aldehydes together with phenols, ureas or melamines, e.g. phenol/formaldehyde, urea/formaldehyde and melamine/formaldehyde resins;

alkyd resins e.g. glycerol/phthalic acid resins and mixtures thereof with melamine/formaldehyde resins;

unsaturated polyester resins derived from copolyesters of saturated and unsaturated dicarboxylic acids with polyhydric alcohols as well as from vinyl compounds as cross-linking agents, and also halogenated flame-resistant modifications thereof The amount of the stabilizers of the invention needed for effective stabilization of synthetic polymers will depend on a variety of factors, such as the type and properties of the polymer concerned, its intended use, and the presence of other stabilizers. It is generally satisfactory to use from 0.01% to 5% by weight of the stabilizers of the invention, based on the weight of the polymer, but most effective range will vary with the type of polymer: viz. 0.01% to 2.0%, preferably 0.02% to 1.0%, by weight for olefin, diene and styrene polymers; 0.01% to 1.0%, preferably 0.02% to 0.5%, by weight for vinyl and vinylidene polymers; and 0.01% to 5.0%, preferably 0.02% to 2.0%, by weight for polyurethanes and polyamides. If desired, two or more of the stabilizers of the invention may be used together.

The stabilizers of the invention may readily be incorporated into synthetic polymers by conventional techniques at any convenient stage prior to the manufacture of shaped articles therefrom. For example, the stabilizer may be mixed with the polymer in dry powder form, or a suspension or emulsion of the stabilizer may be mixed with a solution, suspension or emulsion of the polymer.

The stabilized polymer composition of the invention may optionally contain one or more of various additives conventionally used in polymer technology, such as the additives listed in British Patent Specification No. 1 401 924, at pages 11–13.

The invention is further illustrated by the following non-limiting Examples, in which all parts and percentages are by weight.

EXAMPLE 1

2,2-bis{4-[2-hydroxy-3-(4-hydroxy-2,2,6,6-tetramethylpiperidino)propoxy]phenyl}propane (Compound No. 14)

18.8 g of 4-hydroxy-2,2,6,6-tetramethylpiperidine and 17.0 g of 2,2-bis[4-(2,3-epoxypropoxy)phenyl]propane were added to 200 ml of n-octanol, and the mixture was then heated, with stirring, at 160°–170° C. for 7 hours. When the reaction was complete, the solvent was removed by evaporation under reduced pressure and then the residue obtained was washed successively with water and with petroleum benzine and then recrystallized from ethyl acetate, to give the desired Compound No. 14 in the form of white crystals melting at 191°–193° C.

EXAMPLE 2

2,2-bis{4-[2-hydroxy-3-(4-benzoyloxy-2,2,6,6-tetramethylpiperidino)propoxy]phenyl}propane (Compound No. 26)

34.0 g of 4-benzoyloxy-2,2,6,6-tetramethylpiperidine and 4.4 g of 2,2-bis[4-(2,3-epoxypropoxy)phenyl]propane were added to a mixed solvent consisting of 30 ml of ethylene glycol and 30 ml of benzene; the mixture was then heated at 90° C. for 28 hours. After completion of the reaction, chloroform was added to the mixture and then the mixture was washed with water and dried over anhydrous magnesium sulphate. The solvent was removed from the mixture by evaporation under reduced pressure and then the residue was purified by column chromatography through silica gel eluted with a 4:1 by volume mixture of benzene and diethyl ether. The desired Compound No. 26 was obtained in the form of a white powder having an Rf value of 0.35 on thin-layer chromatography on silica gel in which the upper layer was developed with a mixed solvent consisting of benzene, diethyl ether and 10% w/w aqueous ammonia in a 20:5:12 by volume ratio.

EXAMPLE 3

2,2-bis[4-(2-hydroxy-3-{4-[3-(4-hydroxy-3,5-di-t-butylphenyl)propionyloxy]-2,2,6,6-tetramethylpiperidino}-propoxy)phenyl]propane (Compound No. 31)

8.1 g of 4-[3-(4-hydroxy-3,5-di-t-butylphenyl)propionoyloxy]-2,2,6,6-tetramethylpiperidine and 2.6 g of 2,2-bis[4-(2,3-epoxypropoxy)phenyl]propane were added to 80 ml of n-butanol and then the mixture was refluxed for 40 hours. At the end of this time, benzene was added to the reaction mixture, which was then washed with water and dried over anhydrous magnesium sulphate. The solvent was then removed by evaporation under reduced pressure, after which the residue was purified by column chromatography through silica gel eluted with a 9:1 by volume mixture of benzene and ethyl acetate. The desired Compound No. 31 was obtained in the form of a white powder having an Rf value of 0.60 on thin-layer chromatography on silica gel developed with a 20:2:1 by volume mixture of benzene, ethyl acetate and triethylamine.

EXAMPLE 4

1,1'-[isopropylidenebis(p-phenyleneoxy)bis(3-[p-{p-[2-hydroxy-3-(4-hydroxy-2,2,6,6-tetramethylpiperidino)-propoxy]-α,α-dimethylbenzyl}-phenoxy]-2-propanol) (Compound No. 72)

9.0 g of 4-hydroxy-2,2,6,6-tetramethylpiperidine and 22.7 g of 1,1'-[isopropylidenebis(p-phenyleneoxy)]bis(3-{p-[p-(2,3-epoxypropoxy)-α,α-dimethylbenzyl]phenoxy}-2-propanol)were added to 250 ml of isopentyl alcohol, and then the mixture was allowed to react and treated in the manner described in Example 1 to give the desired Compound No. 72 in the form of a white powder. The Compound had an Rf value of 0.42 on thin-layer chromatography on silica gel developed with a 20:2:3:1 by volume mixture of ethyl acetate, benzene, ethanol and triethylamine.

EXAMPLE 5 bis[2-hydroxy-3-(4-hydroxy-2,2,6,6-tetramethylpiperidino)propyl]1,2-cyclohexanedicarboxylate (Compound No. 90)

A mixture of 11.0 g of 4-hydroxy-2,2,6,6-tetramethylpiperidine and 7.0 g of bis(2,3-epoxypropyl)1,2-cyclohexanedicarboxylate was heated, with stirring, at 170°-180° C. for 5 hours. After completion of the reaction, benzene was added to the reaction mixture and then the benzene solution was washed with water and dried over anhydrous potassium carbonate. The solvent was evaporated under reduced pressure from the benzene solution, leaving a residue, which was then purified by column chromatography through silica gel eluted with a 16:2:1:1 by volume mixture of ethyl acetate, benzene, ethanol and triethylamine, giving the desired Compound No. 90 as a vitreous solid. The Compound had an Rf value of 0.32 on thin-layer chromatography on silica gel developed with a 16:2:3:1 by volume mixture of ethyl acetate, benzene, ethanol and triethylamine.

EXAMPLE 6

2,2-bis{4-[2-hydroxy-3-(4-benzoyloxy-2,2,6,6-tetramethylpiperidino)propoxy]cyclohexyl}propane (Compound No. 78)

A mixture of 30.0 g of 4-benzoyloxy-2,2,6,6-tetramethylpiperidine and 15.0 g of 2,2-bis[4-(2,3-epoxypropoxy)cyclohexyl]propane was reacted folowing the procedure described in Example 5, giving the desired Compound No. 78 in the form of a colourless, viscous liquid. The Compound had an Rf value of 0.70 on thin-layer chromatography on silica gel developed with a 15:5:1 by volume mixture of n-hexane, triethylamine and ethanol.

EXAMPLE 7 bis[2-hydroxy-3-(4-hydroxy-2,2,6,6-tetramethylpiperidino)propyl]phthalate (Compound No. 87)

A mixture of 20.0 g of 4-hydroxy-2,2,6,6-tetramethylpiperidine and 13.9 g of bis(2,3-epoxypropyl)phthalate was reacted following the procedure described in Example 5, to give the desired Compound No. 87 in the form of a white powder. The Compound had an Rf value of 0.24 on thin-layer chromatography on silica gel developed with a 20:4:2:1 by volume mixture of ethyl acetate, benzene, ethanol and triethylamine.

EXAMPLE 8 bis[2-hydroxy-3-(4-benzoyloxy-2,2,6,6-tetramethylpiperidino)2-hydroxypropyl]sebacate (Compound No. 84)

0.45 g of 4-benzoyloxy-1-(2,3-epoxypropyl)-2,2,6,6-tetramethylpiperidine and 0.14 g of sebacic acid were added to a mixed solvent consisting of 1 ml of toluene and 1 ml of t-butanol. The mixture was then heated at 95°-110° C. for 18 hours. At the end of this time, benzene was added to the reaction mixture and then the benzene solution was washed with a 25% w/w aqueous solution of potassium hydrogen carbonate and dried over anhydrous magnesium sulphate. The solvent was removed by evaporation under reduced pressure and then the residue thus obtained was purified by column chromatography through silica gel eluted with a 2:1 by volume mixture of benzene and ethyl acetate. The desired Compound No. 84 was obtained in the form of a colourless oil having an Rf value of 0.74 on thin-layer chromatography on silica gel developed with ethyl acetate.

EXAMPLE 9

2-hydroxy-1,3-bis[2-hydroxy-3-(4-hydroxy-2,2,6,6-tetramethylpiperidino)propoxy]propane (Compound No. 109)

6.2 g of 4-hydroxy-2,2,6,6-tetramethylpiperidine and 2.0 g of glycerol α,γ-bis(2,3-epoxypropyl)ether were added to 20 ml of t-butanol, and then the mixture was reacted as described in Example 1, to give the desired Compound No. 109 in the form of a colourless oil having an Rf value of 0.39 on thin-layer chromatography on silica gel developed with a 4:4:4:1:1 by volume mixture of benzene, ethyl acetate, chloroform, methanol and triethylamine.

EXAMPLE 10

1,3-bis[3-(4-benzoyloxy-2,2,6,6-tetramethylpiperidino)-2-hydroxypropoxy]-2-hydroxypropane (Compound No. 110)

10.4 g of 4-benzoyloxy-2,2,6,6-tetramethylpiperidine and 2.0 g of glycerol α,γ-bis(2,3-epoxypropyl)ether were added to a mixed solvent consisting of 2 ml of benzene, 2 ml of ethylene glycol and 2 ml of t-butanol; the mixture was then refluxed for 28 hours. At the end of this time, benzene was added to the reaction mixture and then the benzene solution was washed in water and dried over anhydrous magnesium sulphate. The solvent was removed by evaporation under reduced pressure and then the residue was purified by column chromatography through silica gel eluted with a 8:8:1 by volume mixture of benzene, ethyl acetate and methanol. The desired Compound No. 110 was obtained in the form of a white vitreous solid, having an Rf value of 0.33 on thin-layer chromatography on silica gel developed with a 10:10:1:1 by volume mixture of benzene, ethyl acetate, ethanol and triethylamine.

EXAMPLE 11

1,2,3-Tris[3-(4-benzoyloxy-2,2,6,6-tetramethylpiperidino)-2-hydroxypropoxy]propane (Compound No. 115)

A mixture of 10.1 g of 4-benzoyloxy-2,2,6,6-tetramethylpiperidine and 2.6 g of glycerol tris(2,3-epoxypropyl)ether was reacted following the procedure described in Example 5 to give the desired Compound No. 115 in the form of a white vitreous solid having an Rf value of 0.87 on thin-layer chromatography on silica gel developed with a 4:1 by volume mixture of ethyl acetate and triethylamine.

EXAMPLE 12

2-acetoxy-1,3-bis[2-acetoxy-3-(4-benzoyloxy-2,2,6,6-tetramethylpiperidino)propoxy]propane (Compound No. 111)

To 2.2 g of 1,3-bis[3-(4-benzoyloxy-2,2,6,6-tetramethylpiperidino)-2-hydroxypropoxy]-2-hydroxypropane (obtained as described in Example 10) were added 2 ml of benzene, 2 ml of triethylamine and 2 ml of acetic anhydride; the mixture was then refluxed for 14 hours. After completion of the reaction, benzene was added to the reaction mixture and then the benzene solution was washed with a 3% w/w aqueous solution of potassium hydrogen carbonate and dried over anhydrous potassium carbonate. The solvent was removed from the benzene solution by evaporation under reduced pressure, and the resulting residue was purified by column chromatography through silica gel eluted with a 4:1 by volume mixture of benzene and ethyl acetate, to give the desired Compound No. 111 in the form of a colourless oil having an Rf value of 0.42 on thin-layer chromatography on silica gel developed with a 4:1 by volume mixture of benzene and ethyl acetate.

EXAMPLE 13

1,2,3-tris[2-acetoxy-3-(4-benzoyloxy-2,2,6,6-tetramethylpiperidino)propoxy]propane (Compound No. 116)

A mixture of 106 mg of 1,2,3-tris[3-(4-benzoyloxy-2,2,6,6-tetramethylpiperidino)-2-hydroxypropoxy]propane (obtained as described in Example 11) and 0.7 ml of acetic anhydride were reacted in 0.5 ml of triethylamine and 3 ml of benzene following the procedure described in Example 12. The desired Compound No. 116 was obtained in the form of a colourless oil having an Rf value of 0.55 on thin-layer chromatography on silica gel developed with a 1:1:1:1 by volume mixture of n-hexane, benzene, chloroform and ethyl acetate.

EXAMPLE 14

2,2-bis{4-[2-acetoxy-3-(4-acetoxy-2,2,6,6-tetramethylpiperidino)propoxy]phenyl}propane (Compound No. 37)

To 1.5 g of 2,2-bis{4-[2-hydroxy-3-(4-hydroxy-2,2,6,6-tetramethylpiperidino)propoxy]phenyl}propane (obtained as described in Example 1) were added 50 ml of acetic anhydride; the mixture was then heated at 100°–110° C. for 7 hours. After completion of the reaction, the reaction mixture was condensed by evaporation under reduced pressure and a 3% w/w aqueous solution of sodium carbonate was added to the resulting residue, which was then extracted with benzene. The extract was washed successively with a 1% w/w aqueous solution of sodium hydrogen carbonate and with water and then dried over anhydrous sodium carbonate. The solvent was removed from the dried solution by evaporation under reduced pressure and the resulting residue was purified by column chromatography through silica gel eluted with a 8:1:1:1 by volume mixture of ethyl acetate, benzene, ethanol and triethylamine. The desired Compound No. 37 was obtained in the form of a white powder having an Rf value of 0.69 on thin-layer chromatography on silica gel developed with a 8:1:1:1 by volume mixture of ethyl acetate, benzene, ethanol and triethylamine.

EXAMPLE 15

2,2-bis{4-[2-lauroyloxy-3-(4-lauroyloxy-2,2,6,6-tetramethylpiperidino)propoxy]phenyl}propane (Compound No. 40)

A mixture of 2.0 g of 2,2-bis{4-[2-hydroxy-3-(4-hydroxy-2,2,6,6-tetramethylpiperidino)propoxy]phenyl}propane (obtained as described in Example 1) and 9.0 g of lauric anhydride was refluxed for 4 days. After completion of the reaction, the reaction mixture was condensed by evaporation under reduced pressure and an aqueous solution of potassium carbonate was added to the residue. The residue was extracted with ethyl acetate and the extract was washed with water and dried over anhydrous magnesium sulphate. The solvent was removed from the dried extract by evaporation under reduced pressure and the resulting residue was purified by column chromatography through silica gel eluted with a 20:20:1 by volume mixture of benzene, n-hexane and ethyl acetate. The desired Compound No. 40 was obtained in the form of a colourless oil having an Rf value of 0.44 on thin-layer chromatography on silica gel developed with a 10:10:1 by volume mixture of n-hexane, benzene and ethyl acetate.

EXAMPLE 16

2,2-bis{4-[2-benzoyloxy-3-(4-benzoyloxy-2,2,6,6-tetramethylpiperidino)propoxy]phenyl}propane (Compound No. 46)

To 4 ml of lutidine were added 2.3 g of 2,2-bis{4-[2-hydroxy-3-[4-hydroxy-2,2,6,6-tetramethylpiperidino)- propoxy]phenyl}propane (obtained as described in Example 1) and 2.7 g of benzoic anhydride; the mixture was then reacted following the procedure described in the Example 15 to give the desired Compound No. 46 in the form of a white powder having an Rf value of 0.42 on thin-layer chromatography on silica gel developed with a 5:5:1 by volume mixture of n-hexane, benzene and diethyl ether.

EXAMPLE 17

2,2-bis{4-[β-{4-hydroxy-3,5-di-t-butylphenyl}propionyloxy)-3-(4-{β-[4-hydroxy-3,5-di-t-butylphenyl]-propionyloxy}-2,2,6,6-tetramethylpiperidino)propoxy]-phenyl}propane (Compound No. 51)

To 200 ml of xylene were added 2.4 g of 2,2-bis(4-[2-hydroxy-3-[4-[β-(4-hydroxy-3,5-di--butylphenyl)propionyloxy]-2,2,6,6-tetramethyl-piperidino}propoxy]phenyl)propane (obtained as described in Example 3), 1,3 g of methyl β-(4-hydroxy-3,5-di-t-butylphenyl)propionate and 0.2 g of lithium amide; the mixture was refluxed for 20 hours, whilst progressively removing formed methanol with xylene. The mixture was heated at such a rate that the xylene could be added at times and in amounts corresponding to the methanol and xylene removed, thereby keeping the volume of the mixture constant. After completion of the reaction, the reaction mixture was filtered through sellaite and the filtrate was washed with water and dried over anhydrous magnesium sulphate. The solvent was removed from the dried solution by evaporation under reduced pressure and the resulting residue was purified by column chromatography through silica gel eluted with a 20:1 by volume mixture of benzene and ethyl acetate. The desired Compound No. 51 was obtained in the form of a white powder having an Rf value of 0.35 on thin-layer chromatography on silica gel developed with a 10:10:1 by volume mixture of n-hexane, benzene and ethyl acetate.

EXAMPLE 18

2,2-bis{4-[2-phenylcarbamoyloxy-3-(2,2,6,6-tetramethyl-4-phenylcarbamoyloxypiperidino)propoxy]phenyl}-propane (Compound No. 57)

To 600 ml of benzene were added 3.3 g of 2,2-bis{4-[2-hydroxy-3-(4-hydroxy-2,2,6,6-tetramethyl-piperidino)-propoxy]phenyl}propane and 24 g of phenyl isocyanate, and the mixture was refluxed for 12 hours. After completion of the reaction, the reaction mixture was condensed by evaporation under reduced pressure and the residue was purified by column chromatography through silica gel eluted with ethyl acetate. The desired Compound No. 57 was obtained as a sticky mass having an Rf value of 0.74 on thin-layer chromatography on silica gel developed with a 8:1:1:1 by volume mixture of ethyl acetate, benzene, ethanol and triethylamine.

EXAMPLE 19

2,2-bis{4-[2-methoxy-3-(4-methoxy-2,2,6,6-tetramethyl-piperidino)propoxy]phenyl}propane (Compound No. 29)

To 200 ml of dioxan were added 16.3 g of 2,2-bis{4-[2-hydroxy-3-(4-hydroxy-2,2,6,6-tetramethyl-piperidino)propoxy]phenyl}propane (obtained as described in Example 1) and 14.0 g of sodium hydroxide. 35.0 g of dimethyl sulphate were then added dropwise to the mixture at 50°-60° C. over 2 hours. After completion of the addition, the mixture was stirred at 50°-60° C. for a further 2 hours, and then at 70°-80° C. for an additional 4 hours. After completion of the reaction, the reaction mixture was condensed by evaporation under reduced pressure and benzene was added to the resulting residue. The benzene solution was washed successively with a 1% w/w aqueous solution of sodium hydroxide and with water and then dried over anhydrous potassium carbonate. The residue obtained by removing the solvent from the benzene solution, by evaporation under reduced pressure, was purified by column chromatography through silica gel eluted with a 16:2:2:1 by volume mixture of ethyl acetate, benzene, ethanol and triethylamine. The desired Compound No. 29 was obtained in the form of a white vitreous mass having an Rf value of 0.63 on thin-layer chromatography on silica gel developed with a 16:2:3:1 by volume mixture of ethyl acetate, benzene, ethanol and triethylamine.

EXAMPLE 20

2,2-bis{4-[2-butoxy-3-(4-butoxy-2,2,6,6-tetramethyl-piperidino)propoxy]phenyl}propane (Compound No. 30)

To 300 ml of t-pentyl alcohol were added potassium t-pentoxide (prepared from 5.0 g of metallic potassium) and 6.6 g of 2,2-bis{4-[2-hydroxy-3-(4-hydroxy-2,2,6,6-tetramethylpiperidino)propoxy]-phenyl}propane (obtained as described in Example 1); the mixture was refluxed for 2 hours. The reaction mixture was cooled to ambient temperature and there were added 10.0 g of n-butyl bromide. The mixture was heated at 50°-60° C. for 15 hours. After completion of the reaction, the reaction mixture was condensed by evaporation under reduced pressure and the residue was extracted with benzene. The extract was washed with water and dried over anhydrous potassium carbonate. The solvent was removed from the dried solution by evaporation under reduced pressure and the resulting residue was purified by column chromatography through silica gel eluted with a 2:5 by volume mixture of ethyl acetate and benzene. The desired Compound No. 30 was obtained in the form of a colourless viscous oil having an Rf value of 0.68 on thin-layer chromatography on silica gel developed with a 8:1:1:1 by volume mixture of ethyl acetate, benzene, ethanol and triethylamine.

EXAMPLE 21

2,2-bis{4-[2-hydroxy-3-(2-hydroxymethyl-7,7,9,9-tetramethyl-1,4-dioxa-8-azaspiro[4.5]dec-8-yl)propoxy]-phenyl}propane (Compound No. 161)

To 80 ml of n-butanol were added 10.0 g of 2-hydroxymethyl-7,7,9,9-tetramethyl-1,4-dioxa-8-azaspiro[4.5]-decane and 6.2 g of 2,2-bis[p-(2,3-epoxypropoxy)-phenyl]propane and the mixture was refluxed for 3 days. After completion of the reaction, the solvent was removed from the reaction mixture by evaporation under reduced pressure and ethyl acetate was added to the residue. The ethyl acetate solution was washed with water and dried over anhydrous magnesium sulphate. The residue obtained by removing the solvent, by evaporation under reduced pressure, from the ethyl acetate solution was purified by column chromatography through silica gel eluted with a 20:1:1 by volume mixture of ethyl acetate, ethanol and triethylamine. The desired Compound No. 161 was obtained in the form of a vitreous solid having an Rf value of 0.45 on thin-layer chromatography on silica gel developed with a 20:1:1 by volume mixture of ethyl acetate, ethanol and triethylamine.

EXAMPLE 22

2,2-bis{4-[2-hydroxy-3-(7,7,9,9-tetramethyl-1,4-dioxa-8-azaspiro[4.5]dec-8-yl)propoxy]phenyl}propane (Compound No. 126)

To 50 ml of t-butanol were added 3.5 g of 2,2-bis[p-(2,3-epoxypropoxy)phenyl]propane and 5.0 g of 7,7,9,9-tetramethyl-1,4-dioxa-8-azaspiro[4.5]decane; the mixture was then reacted following the procedure described in Example 21 to give the desired Compound No. 126 in the form of a white powder having an Rf value of 0.38 on thin-layer chromatography on silica gel developed with a 20:2:1 by volume mixture of benzene, ethyl acetate and triethylamine.

EXAMPLE 23

2,2-bis{4-[2-lauroyloxy-3-(2-lauroyloxymethyl-7,7,9,9-tetramethyl-1,4-dioxa-8-azaspiro[4.5]dec-8-yl)propoxy]phenyl}propane (Compound No. 169)

To 30 ml of xylene were added 2.0 g of 2,2-bis{4-[2-hydroxy-3-(2-hydroxymethyl-7,7,9,9-tetramethyl-1,4-dioxa-8-azaspiro[4.5]dec-8-yl)propoxy]phenyl}propane (obtained as described in Example 21) and 7.4 g of lauric anhydride and the mixture was refluxed for 25 hours. After completion of the reaction, the reaction mixture was condensed by evaporation under reduced pressure and a 10% w/w aqueous solution of potassium carbonate was added to the residue. The residue was extracted with benzene and the extract was washed with water and then dried over anhydrous magnesium sulphate. The residue obtained by evaporating the solvent under reduced pressure from the extract was purified by column chromatography through silica gel eluted with a 20:1 by volume mixture of benzene and ethyl acetate. The desired Compound No. 169 was obtained in the form of a colourless oil having an Rf value of 0.49 on thin-layer chromatography on silica gel developed with a 10:1 by volume mixture of benzene and ethyl acetate.

EXAMPLE 24

2,2-bis{4-[2-acetoxy-3-(2-acetoxymethyl-7,7,9,9-tetramethyl-1,4-dioxa-8-azaspiro[4.5]dec-8-yl)propoxy]phenyl}propane (Compound No. 164)

To 20 ml of acetic anhydride were added 2.0 g of 2,2-bis{4-[2-hydroxy-3-(2-hydroxymethyl-7,7,9,9-tetramethyl-1,4-dioxa-8-azaspiro[4.5]dec-8-yl)propoxy]phenyl}propane (obtained as described in Example 21), and the mixture was heated at 100° C. for 7 hours. After completion of the reaction, water was poured into the reaction mixture, which was then neutralized with potassium carbonate and extracted with benzene. The extract was washed with water and dried over anhydrous magnesium sulphate. The residue obtained by evaporating the solvent under reduced pressure from the extract was purified by column chromatography through silica gel eluted with a 3:2 by volume mixture of benzene and ethyl acetate. The desired Compound No. 164 was obtained in the form of a colourless oil. The compound had an Rf value of 0.44 on thin-layer chromatography on silica gel developed with a 3:2 by volume mixture of benzene and ethyl acetate.

EXAMPLE 25

2,2-bis[4-{3-[4-(N-butylacetamido)-2,2,6,6-tetramethylpiperidino]-2-hydroxypropoxy}phenyl]propane (Compound No. 234)

To 20 ml of t-butanol were added 5.0 g of 4-(N-butylacetamido)-2,2,6,6-tetramethylpiperidine and 2.8 g of 2,2-bis[p-(2,3-epoxypropoxy)phenyl]propane, and the mixture was reacted following the procedure described in Example 1 to give the desired Compound No. 234 in the form of a white vitreous mass. The compound had an Rf value of 0.54 on thin-layer chromatography on silica gel developed with a 20:1 by volume mixture of ethyl acetate and triethylamine.

EXAMPLE 26

2,2-bis{4-[2-hydroxy-3-(2,2,6,6-tetramethyl-4-morpholinopiperidino)propoxy]phenyl}propane (Compound No. 252)

A mixture of 3.0 g of 2,2,6,6-tetramethyl-4-morpholinopiperidine and 2.0 g of 2,2-bis[p-(2,3-epoxypropoxy)phenyl]propane was reacted following the procedure described in Example 5 to give the desired Compound No. 252 in the form of white crystals melting at 136°–139° C.

EXAMPLE 27

2,2-bis{4-[2-hydroxy-3-(2,2,6,6-tetramethylpiperidino)propoxy]phenyl}propane (Compound No. 1)

To 50 ml of t-butanol were added 14.1 g of 2,2,6,6-tetramethylpiperidine and 10.2 g of 2,2-bis[p-(2,3-epoxypropoxy)phenyl]propane, and the mixture was reacted following the procedure described in Example 21 to give the desired Compound No. 1 in the form of white crystals melting at 110°–112° C.

EXAMLE 28 tris[2-hydroxy-3-(2,2,6,6-tetramethylpiperidino)propyl]isocyanurate (Compound No. 13)

A mixture of 14.1 g of 2,2,6,6-tetramethylpiperidine and 4.5 g of tris(2,3-epoxypropyl)isocyanurate was reacted following the procedure described in Example 5 to give the desired Compound No. 13 in the form of white crystals melting at 118°–120° C.

EXAMPLE 29

2,2-bis[4-{2-hydroxy-3-[3-(2-lauroyloxyethyl)-7,7,9,9-tetramethyl-2,4-dioxo-1,3,8-triazaspiro[4.5]dec-8-yl]propoxy}phenyl]propane (Compound No. 294)

To a mixed solvent consisting of 1.0 g of ethylene glycol and 1.0 g of t-butanol were added 3.9 g of 3-(2-lauroyloxyethyl)-7,7,9,9-tetramethyl-1,3,8-triazaspiro[4.5]decane-2,4-dione and 1.2 g of 2,2-bis[p-(2,3-epoxypropoxy)phenyl]propane; the mixture was heated at 110°–120° C. for 60 hours and then at 160° C. for an additional 1 hour. After completion of the reaction, benzene was added to the reaction mixture, and the benzene solution was washed with water and condensed by evaporation under reduced pressure. The residue was washed with n-hexane and the resulting solid mass was purified by column chromatography using silica gel eluted with a 20:20:1 by volume mixture of benzene, ethyl acetate and methanol. The desired Compound No. 294 was obtained in the form of a white powder and had an Rf value of 0.64 on thin-layer chro-

EXAMPLE 30

2,2-bis[4-{2-lauroyloxy-3-[3-(2-lauroyloxyethyl)-7,7,9,9-tetramethyl-2,4-dioxo-1,3,8-triazaspiro[4.5]dec-8-yl]propoxy}phenyl]propane (Compound No. 305)

To 2.0 g of chloroform were added 1.2 g of 2,2-bis[4-{2-hydroxy-3-[3-(2-lauroyloxyethyl)-7,7,9,9-tetramethyl-2,4-dioxo-1,3,8-triazaspiro[4.5]dec-8-yl]propoxy}phenyl]propane (prepared as described in Example 29), 1.5 g of lauric anhydride and 2.0 g of triethylamine; the mixture was heated at 90°–100° C. for 20 hours. After completion of the reaction, chloroform was added to the reaction mixture, and the chloroform solution was washed successively with a 3% w/w aqueous solution of potassium carbonate and with water and then dried over anhydrous magnesium sulphate. The residue obtained by evaporating the solvent under reduced pressure from the chloroform solution was purified by column chromatography through silica gel eluted with a 60:30:37 by volume mixture of n-hexane, benzene and ethyl acetate. The desired Compound No. 305 was obtained in the form of a white powder and had an Rf value of 0.25 on thin-layer chromatography on silica gel developed with a 2:1:1 by volume miture of n-hexane, benzene and ethyl acetate.

EXAMPLE 31 ethylene glycol bis[2-hydroxy-3-(3,7,7,9,9-pentamethyl-2,4-dioxo-1,3,8-triazaspiro[4.5]dec-8-yl)propyl]ether (Compound No. 340)

To 50 ml of n-octanol were added 5.0 g of 3,7,7,9,9-pentamethyl-1,3,8-triazaspiro[4.5]decane-2,4-dione and 1.5 g of ethylene glycol bis(2,3-epoxypropyl) ether; the mixture was then reacted as described in Example 1 to give the desired Compound No. 340 in the form of a white powder. The compound had an Rf value of 0.54 on thin-layer chromatography on silica gel developed with a 20:1:1 by volume mixture of ethyl acetate, ethanol and triethylamine.

EXAMPLE 32

2,2-bis{4-[2-hydroxy-3-(7,7,9,9-tetramethyl-1,4-dioxa-8-azaspiro[4.5]dec-8-yl)propoxy]cyclohexyl}propane (Compound No. 207)

A mixture of 8.8 g of 7,7,9,9-tetramethyl-1,4-dioxa-8-azaspiro[4.5]decane and 7.0 g of 2,2-bis[4-(2,3-epoxypropoxy)cyclohexyl]propane was heated at 120° C. for 30 hours. After completion of the reaction, the reaction mixture was purified by column chromatography through silica gel eluted with ethyl acetate. The desired Compound No. 207 was obtained in the form of a pale yellow oil which after being kept at ambient temperature, turned to a solid melting at 48°–50° C.

EXAMPLE 33 bis[2-hydroxy-3-(7,7,9,9-tetramethyl-1,4-dioxa-8-azaspiro[4.5]dec-8-yl)propyl]adipate (Compound No. 208)

A mixture of 10 g of 8-(2,3-epoxypropyl)-7,7,9,9-tetramethyl-1,4-dioxa-8-azaspiro[4.5]decane and 2.4 g of adipic acid in 60 ml of xylene was refluxed for 16 hours. After completion of the reaction, the residue obtained by evaporating the solvent under reduced pressure from the reaction mixture was purified by column chromatography through silica gel eluted with a 1:1 by volume mixture of ethyl acetate and benzene. The desired Compound No. 208 was obtained in the form of a pale yellow, viscous product. The compound had an Rf value of 0.53 on thin-layer chromatography on silica gel developed with ethyl acetate.

EXAMPLE 34

2,2-bis{4-[2-benzoyloxy-3-(7,7,9,9-tetramethyl-1,4-dioxa-8-azaspiro[4.5]dec-8-yl)propoxy]cyclohexyl}propane (Compound No. 222)

1.5 g of 2,2-bis{4-[2-hydroxy-3-(7,7,9,9-tetramethyl-1,4-dioxa-8-azaspiro[4.5]dec-8-yl)propoxy]cyclohexyl}propane and 1.2 g of 2-benzoylthiobenzthiazole were refluxed in 30 ml of anhydrous benzene for 4.5 hours. After completion of the reaction, the reaction mixture was treated with an aqueous alkali and then extracted with benzene, giving crystals. The crystals were purified by column chromatography through silica gel eluted with a 4:1 by volume mixture of diethyl ether and ethyl acetate. The desired Compound No. 222 was obtained in the form of a white powder melting at 77°–79° C.

EXAMPLE 35

2,2-bis[4-(N-butylacetamido)-2,2,6,6-tetramethylpiperidino]-2-hydroxypropoxy}cyclohexyl]propane (Compound No. 280)

A mixture of 5.1 g of 4-(N-butylacetamido)-2,2,6,6-tetramethylpiperidine and 3.5 g of 2,2-bis[4-(2,3-epoxypropoxy)cyclohexyl]propane was heated at 200°–210° C. for 5 hours under a stream of nitrogen. After completion of the reaction, the reaction mixture was purified by column chromatography through silica gel eluted with a 19:1 by volume mixture of ethyl acetate and triethylamine. The desired Compound No. 280 was obtained in the form of a pale yellow powder, softening at 50°–65° C.

EXAMPLE 36

2,2-bis{4-[3-(3-dodecyl-7,7,9,9-tetramethyl-2,4-dioxo-1,3,8-triazaspiro[4.5]dec-8-yl)-2-hydroxypropoxy]phenyl}propane (Compound No. 285)

A mixture of 8.6 g of 3-dodecyl-7,7,9,9-tetramethyl-1,3,8-triazaspiro[4.5]decane-2,4-dione and 3.4 g of 2,2-bis[4-(2,3-epoxypropoxy)phenyl]propane in 5 ml of n-octanol was heated at 180° C. for 7 hours. After completion of the reaction, diethyl ether was added to the reaction mixture and the resulting crystals were separated and purified by column chromatography through silica gel eluted with a 1:1 by volume mixture of benzene and ethyl acetate. The desired Compound No. 285 was obtained in the form of white crystals melting at 159°–161° C.

EXAMPLE 37

2,2-bis{4-[2-hydroxy-3-(7,7,9,9-tetramethyl-3-octyl-2,4-dioxo-1,3,8-triazaspiro[4.5]dec-8-yl)propoxy]cyclohexyl}propane (Compound No. 327)

A mixture of 10 g of 7,7,9,9-tetramethyl-3-octyl-1,3,8-triazaspiro[4.5]decane-2,4-dione and 3.5 g of 2,2-bis[4-(2,3-epoxypropoxy)cyclohexyl]propane was heated at 130°–150° C. for 10 hours. After completion of the reaction, the reaction mixture was purified by column chromatography through silica gel eluted with 1:1 by volume mixture of ethyl acetate and benzene and then by recrystallization from ethyl acetate, giving the desired Compound No. 327 in the form of white crystals melting at 166°–170° C.

EXAMPLE 38

2,2-bis{4-[2-acetoxy-3-(1-acetyl-3-dodecyl-7,7,9,9-tetramethyl-2,4-dioxo-1,3,8-triazaspiro[4.5]dec-8-yl)propoxy]phenyl}propane (Compound No. 259)

A mixture of 1.1 g of 2,2-bis{4-[2-hydroxy-3-(3-dodecyl-7,7,9,9-tetramethyl-2,4-dioxo-1,3,8-triazaspiro[4.5]dec-8-yl)propoxy]phenyl}propane and 10 g of acetic anhydride was refluxed for 48 hours. After completion of the reaction, the reaction mixture was dissolved in ethyl acetate and treated with an aqueous alkali. The solution was then dried and condensed by evaporation under reduced pressure, affording a viscous product which was purified by column chromatography through silica gel eluted with a 1:1 by volume mixture of ethyl acetate and n-hexane, giving the desired Compound No. 259 in the form of a white powder melting at 52°–55° C.

EXAMPLE 39 bis{4-[3-(3-butyl-7,7,9,9-tetramethyl-2,4-dioxo-1,3,8-triazaspiro[4.5]dec-8-yl)-2-hydroxypropoxy]-phenyl}methane (Compound No. 351)

A mixture of 4.0 g of 3-butyl-8-(2,3-epoxypropyl)-7,7,9,9-tetramethyl-1,3,8-triazaspiro[4.5]decane-2,4-dione and 1.0 g of bis(p-hydroxyphenyl)methane in 5 ml of isopentyl alcohol with a catalytic amount of sodium hydride was refluxed for 10 hours. After completion of the reaction, the residue obtained by evaporating the solvent under reduced pressure from the reaction mixture was purified by column chromatography through silica gel eluted with a 1:1 by volume mixture of benzene and ethyl acetate, giving the desired Compound No. 351 in the form of white crystals melting at 202°–204° C.

EXAMPLE 40 ethylene glycol bis[3-(3-dodecyl-7,7,9,9-tetramethyl-2,4-dioxo-1,3,8-triazaspiro[4.5]dec-8-yl)-2-hydroxypropyl]ether (Compound No. 355)

A mixture of 8.6 g of 3-dodecyl-7,7,9,9-tetramethyl-1,3,8-triazaspiro[4.5]decane-2,4-dione and 1.7 g of ethylene glycol bis(2,3-epoxypropyl)ether in 3 ml of octanol was heated to 180° C. for 30 hours. After completion of the reaction, the reaction mixture was dissolved in ethyl acetate and subjected to column chromatography through alumina eluted successively first with diethyl ether, second with a 10:1 by volume mixture of ethyl acetate and triethylamine, and lastly with methanol. The eluate eluted with the last solvent was separated and the solvent was removed therefrom by evaporation under reduced pressure, giving the desired Compound No. 355 in the form of white crystals melting at 74°–76° C.

EXAMPLE 41

1,2,3-tris[2-hydroxy-3-(7,7,9,9-tetramethyl-3-octyl-2,4-dioxo-1,3,8-triazaspiro[4.5]dec-8-yl)propoxy]propane (Compound No. 349)

A mixture of 11.0 g of 7,7,9,9-tetramethyl-3-octyl-1,3,8-triazaspiro[4.5]decane-2,4-dione and 2.6 g of glycerol tris(2,3-epoxypropyl)ether in 10 ml of octanol was heated at 180° C. for 30 hours. After completion of the reaction, the reaction mixture was purified by column chromatography through silica gel eluted with ethyl acetate, giving the desired Compound No. 349 in the form of a colourless oil. The compound had an Rf value of 0.54 on thin-layer chromatography on silica gel when developed with a 10:1 by volume mixture of ethyl acetate and triethylamine.

EXAMPLE 42 bis[2-hydroxy-3-(7,7,9,9-tetramethyl-3-octyl-2,4-dioxo-1,3,8-triazaspiro[4.5]dec-8-yl)propyl]adipate (Compound No. 328)

A mixture of 4.3 g of 8-(2,3-epoxypropyl)-7,7,9,9-tetramethyl-3-octyl-1,3,8-triazaspiro[4.5]decane-2,4-dione and 0.74 g of adipic acid in 20 ml of xylene was refluxed for 16 hours. After completion of the reaction, the xylene was distilled from the reaction mixture in vacuo and the residue was purified by column chromatography through silica gel eluted with ethyl acetate, giving the desired Compound No. 328 in the form of a pale yellow oil. The compound had an Rf value of 0.46 on thin-layer chromatography when developed with ethyl acetate.

EXAMPLE 43

2,2-bis{2-hydroxy-3-[3-(2-{3-(4-hydroxy-3,5-di-t-butylphenyl)propionyloxy}ethyl)-7,7,9,9-tetramethyl-2,4-dioxo-1,3,8-triazaspiro[4.5]dec-8-yl]propyl}adipate (Compound No. 354)

A mixture of 2.0 g of 8-(2,3-epoxypropyl)-3-[2-{3-(4-hydroxy-3,5-di-t-butylphenyl)propionyloxy}ethyl]-7,7,9,9-tetramethyl-1,3,8-triazaspiro[4.5]decane-2,4-dione and 0.2 g of adipic acid in 5 ml of xylene was refluxed for 18 hours. After completion of the reaction, the solvent was removed by evaporation under reduced pressure and the residue was purified by column chromatography through silica gel eluted with a 1:1 by volume mixture of benzene and ethyl acetate, giving the desired Compound No. 354 in the form of a white powder softening at 90°–95° C.

EXAMPLE 44

2,2-bis{4-[2-hydroxy-3-(3-[2-{3-(4-hydroxy-3,5-di-t-butylphenyl)propionyloxy}ethyl]-7,7,9,9-tetramethyl-2,4-dioxo-1,3,8-triazaspiro[4.5]dec-8-yl)propoxy]-phenyl}propane (Compound No. 361)

A mixture of 3-[2-{3-(4-hydroxy-3,5-di-t-butylphenyl)propionyloxy}ethyl]-7,7,9,9-tetramethyl-1,3,8-triazaspiro[4.5]decane-2,4-dione and 1.3 g of 2,2-bis[p-(2,3-epoxypropoxy)phenyl]propane was heated at 160°–170° C. for 5 hours, with stirring. After completion of the reaction, the reaction mixture was purified by column chromatography through silica gel eluted with a 1:1 by volume mixture of benzene and ethyl acetate, giving the desired Compound No. 361 in the form of a white powder softening at 117°–120° C.

EXAMPLE 45 ethylene glycol bis[2-hydroxy-3-(4-hydroxy-2,2,6,6-tetramethylpiperidino)propyl]ether (Compound No. 102)

A mixture of 18.0 g of 4-hydroxy-2,2,6,6-tetramethylpiperidine and 8.7 g of ethylene glycol bis(2,3-epoxypropyl)ether was heated, with stirring, at 170°–180° C. for 6 hours. The reaction mixture was then dissolved in benzene and purified by column chromatography through silica gel eluted with a 20:4:2:1 by volume mixture of ethyl acetate, benzene, ethanol and triethylamine. The desired Compound No. 102 was obtained in the form of a pale yellow, very viscous product having an Rf value of 0.30 on thin-layer chromatography on silica gel developed with a 20:4:2:1 by volume mixture of ethyl acetate, benzene, ethanol and triethylamine.

EXAMPLE 46 bis[2-hydroxy-3-(4-hydroxy-2,2,6,6-tetramethyl-piperidino)propyl]adipate (Compound No. 122)

A mixture of 18.0 g of 4-hydroxy-2,2,6,6-tetramethyl-piperidine and 11.3 g of bis(2,3-epoxypropyl) adipate was reacted and treated following substantially the same procedure as described in Example 45. The desired Compound No. 122 was obtained in the form of a pale yellow, very viscous product having an Rf value of 0.33 on thin-layer chromatography on silica gel developed with a 20:4:2:1 by volume mixture of ethyl acetate, benzene, ethanol and triethylamine.

EXAMPLE 47

Stabilization of polypropylene

Mixtures were made from 100 parts of polypropylene powder (MFI about 18), 0.2 part of stearyl 3-(4-hydroxy-3,5-di-t-butylphenyl)propionate (an antioxidant) and 0.25 part of each in turn of the stabilizers shown in following Table 1. The resulting mixtures were blended and homogenized by means of a Brabender Plastograph at 200° C. for 10 minutes. Each mixture was pressed in a laboratory press to form a sheet 2–3 mm thick. The sheet was compression-moulded at 260° C. for 6 minutes to form a 0.5 mm thick sheet, from which a film of thickness 0.1 mm was obtained by repeating the same procedures. Control sheets were also made, one of the controls containing no stabilizer and the other containing Tinuvin 327, a Trade Mark for 2-(2-hydroxy-3,5-di-t-butylphenyl)-5-chlorobenzo-1,2,3-triazole, sold by Ciba-Geigy AG.

Each film was then cut into 50×120 mm test specimens, which were exposed to light in a Sunshine Carbon Arc Lamp Weather Meter at a black panel temperature of 63°±3° C. and examined periodically to determine the retention of elongation at break. The test results are reported in Table 1 as a ratio of the time to 50% retention of elongation with stabilizers to the time to 50% retention of elongation without stabilizers.

TABLE 1

| Stabilizer Compound No. | Ratio | Stabilizer Compound No. | Ratio |
|---|---|---|---|
| 1 | 4.7 | 115 | 4.3 |
| 13 | 5.2 | 116 | 4.5 |
| 14 | 3.9 | 125 | 4.7 |
| 26 | 4.9 | 161 | 4.8 |
| 29 | 4.7 | 164 | 5.0 |
| 30 | 4.4 | 169 | 4.9 |
| 31 | 5.5 | 207 | 5.0 |
| 37 | 5.8 | 208 | 4.8 |
| 40 | 5.3 | 222 | 5.3 |
| 46 | 5.2 | 234 | 4.4 |
| 51 | 5.3 | 252 | 3.8 |
| 57 | 4.5 | 280 | 6.6 |
| 72 | 3.2 | 285 | 6.3 |
| 78 | 4.7 | 294 | 4.3 |
| 84 | 4.6 | 305 | 4.6 |
| 87 | 4.9 | 327 | 5.7 |
| 90 | 4.3 | 340 | 4.5 |
| 109 | 3.9 | | |

TABLE 1-continued

| Stabilizer Compound No. | Ratio | Stabilizer Compound No. | Ratio |
|---|---|---|---|
| 110 | 4.2 | Tinuvin 327 | 2.0 |
| 111 | 4.5 | None | 1.0 |

EXAMPLE 48

Stabilization of Polyurethane

Mixtures were made from 100 parts of an aromatic polyester-type polyurethane ("Estane 5707", trade name of Goodrich Co.) and 0.5 part of each in turn of the stabilizers of the invention indicated in Table 2; the mixtures were then dissolved in 400 parts of dimethylformamide. The resulting solutions were used to cast films about 500μ thick on a plane glass plate. After air-drying, each film was further dried at 60° C. for 10 minutes and at 140° C. for 6 minutes, giving a film about 100μ thick. The films thus formed were exposed to ultraviolet radiation in a Sunshine Carbon Arc Lamp Weather Meter for 200 hours and the degree of yellowing was measured. The procedure was repeated with control sheets either containing no stabilizer or containing the known stabilizer Tinuvin P.

The results are shown in Table 2.

TABLE 2

| Stabilizer | Yellowness index before irradiation | Yellowness index after irradiation |
|---|---|---|
| 31 | 2.0 | 19.6 |
| 37 | 1.9 | 23.4 |
| 46 | 1.9 | 21.1 |
| 84 | 1.8 | 20.5 |
| 90 | 1.8 | 19.7 |
| 110 | 1.9 | 21.3 |
| 208 | 2.1 | 23.6 |
| 234 | 2.2 | 20.5 |
| 327 | 1.9 | 19.4 |
| Tinuvin P | 1.9 | 36.8 |
| None | 2.1 | 48.9 |

EXAMPLE 49

Stabilization of ABS Resin

Mixtures were made from 100 parts of acrylonitrile/butadiene/styrene (ABS) resin ("Kane-Ace B-12", trade name of Kanegafuchi Chemical Industries Co. Ltd.) and 0.5 part of each in turn of the stabilizers of the invention indicated in Table 3. The resulting mixtures were blended and homogenized on a two-roll mill at 165° C. for 4 minutes, giving sheets about 0.5 mm thick. Control sheets either containing no stabilizer or containing the known stabilizer Tinuvin P were also made. The sheets were compression-moulded at 190° C. for 1 minute to a thickness of 0.5 mm, after which dumbell test specimens were prepared from them and subjected to ultraviolet irradiation in a Sunshine Carbon Arc Lamp Weather Meter for 50 hours. After irradiation, the retention of ultimate elongation and of ultimate tensile strength were measured by standard methods. The results are shown in Table 3.

TABLE 3

| Stabilizer | Retention of elongation (%) | Retention of tensile strength (%) |
|---|---|---|
| 14 | 62 | 76 |
| 46 | 59 | 72 |
| 90 | 61 | 74 |

TABLE 3-continued

| Stabilizer | Retention of elongation (%) | Retention of tensile strength (%) |
|---|---|---|
| 126 | 57 | 74 |
| 234 | 61 | 75 |
| 327 | 58 | 73 |
| Tinuvin P | 43 | 67 |
| None | 17 | 69 |

We claim:

1. A stabilized polymer composition comprising a polymer which does not react with hydroxy groups having incorporated therein, in an amount to stabilize it against thermal- and/or photo-deterioration, a piperidine derivative of formula (I):

$$\left[ \begin{array}{c} R^1\ CH_3\quad CH_2R^1 \\ X\quad N\text{------}Y \\ CH_3\quad CH_2R^1 \end{array} \right]_l \quad (I)$$

wherein:

$R^1$ represents a hydrogen atom or a methyl group;

X represents one of the groups of formula —$CH_2$—, $$\underset{-CH-}{\overset{OR^2}{|}},\ \underset{-C-}{\overset{R^3O}{\diagdown}\overset{OR^4}{\diagup}},\ \underset{-CH-}{\overset{R^5-N-R^6}{|}} \text{ and } R^7-N\overset{O}{\underset{O}{\diagup\diagdown}}N-R^8\ ;$$

wherein:

$R^2$ represents a hydrogen atom, an alkyl group having from 1 to 18 carbon atoms, an allyl group, a benzyl group, an aliphatic, aromatic, araliphatic or alicyclic acyl group having up to 18 carbon atoms, wherein the aromatic moiety is unsubstituted or substituted by one or more $C_1$-$C_4$ alkyl and/or hydroxy groups, or one of the groups of formula $$-CON\diagdown^{R^9}_{R^{10}},\ -P\diagdown^{O-}_{O-}\diagup^{R^{11}}_{R^{11}} \text{ and } -P(OR^{12})_2;$$

wherein:

$R^9$ represents a hydrogen atom or an alkyl group having from 1 to 4 carbon atoms;

$R^{10}$ represents an alkyl group having from 1 to 18 carbon atoms, a phenyl group which is optionally substituted by one or more methyl and/or chlorine substituents, a naphthyl group or a cyclohexyl group;

$R^{11}$ represents a hydrogen atom or an alkyl group having from 1 to 4 carbon atoms; and $R^{12}$ represents an alkyl group having from 1 to 4 carbon atoms, a phenyl group or a group of formula $$\underset{}{\overset{C(CH_3)_3}{\diagup\diagdown}}\!\!R^{13}$$

in which $R^{13}$ represents a hydrogen atom or an alkyl group having from 1 to 4 carbon atoms; $R^3$ and $R^4$ are the same or different and each represents an alkyl group having from 1 to 4 carbon atoms, or $R^3$ and $R^4$ together represent one of the groups of formula $$-CH-\underset{R^{14}}{\overset{R^{16}}{\underset{|}{C}}}-CH_2-\text{ and }-CH_2-\underset{R^{15}}{\overset{R^{17}}{\underset{|}{CH}}}-;$$

in which:

$R^{14}$ and $R^{15}$ are the same or different and each represents a hydrogen atom or an alkyl group having from 1 to 3 carbon atoms; and $R^{16}$ and $R^{17}$ are the same or different and each represents a hydrogen atom, an alkyl group having from 1 to 3 carbon atoms or a group of formula —$CH_2OR^{18}$;

in which $R^{18}$ represents a hydrogen atom, an alkyl group having from 1 to 4 carbon atoms, an aliphatic, aromatic, araliphatic or alicyclic acyl group having up to 18 carbon atoms, wherein the aryl moiety is optionally substituted by one or more $C_1$-$C_4$ alkyl and/or hydroxy groups, or a group of formula $$-CON\diagdown^{R^{19}}_{R^{20}}$$

in which $R^{19}$ is any one of the groups hereinbefore defined for $R^9$ and $R^{20}$ is any one of the groups hereinbefore defined for $R^{10}$;

$R^5$ represents an alkyl group having from 1 to 18 carbon atoms, a phenyl group which is optionally substituted by one or more $C_1$-$C_4$ alkyl and/or alkoxy substituents, a benzyl group or a cyclohexyl group;

$R^6$ represents an alkyl group having from 1 to 18 carbon atoms, a benzyl group or an aliphatic, aromatic, araliphatic or alicyclic acyl group having up to 18 carbon atoms, in which the aryl moiety optionally has one or more $C_1$-$C_4$ alkyl and/or hydroxy substituents; or $R^5$ and $R^6$ together represent a tetramethylene group, a pentamethylene group or a group of formula —$(CH_2)_2$—O—$(CH_2)_2$—;

$R^7$ represents a hydrogen atom, an alkyl group having from 1 to 18 carbon atoms, an allyl group, an acetyl group or a benzyl group; and $R^8$ represents an alkyl group having from 1 to 18 carbon atoms, an alkenyl group having 3 or 4 carbon atoms, a benzyl group or a group of formula

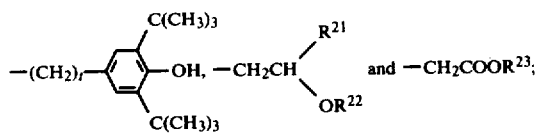

in which:

t represents 1, 2 or 3;

$R^{21}$ represents a hydrogen atom, a methyl group or a phenyl group;

$R^{22}$ represents a hydrogen atom, an alkyl group having from 1 to 8 carbon atoms, an allyl group, a benzyl group or an aliphatic, aromatic, araliphatic or alicyclic acyl group having up to 18 carbon atoms, wherein the aryl moiety optionally has one or more $C_1$-$C_4$ alkyl and/or hydroxy substituents; and $R^{23}$ represents an alkyl group having from 1 to 18 carbon atoms, an alkenyl group having 3 or 4 carbon atoms or a phenyl group;

l represents 2 or 3; and when l=2:

Y represents one of the groups of formula —$CH_2CH(OZ)CH_2$-[$OCH_2CH(OZ)CH_2$]$_2$—, —$CH_2CH(OZ)CH_2$-[$OCH_2CH(R^{24})$]$_m$—$OCH_2CH(OZ)CH_2$— and —$CH_2CH(OZ)CH_2$-[$OWO$—$CH_2CH(OZ)CH_2$]$_n$—;

wherein:

m and n each represent integers of from 1 to 10;

$R^{24}$ represents a hydrogen atom or a methyl group;

W represents one of the groups of formulae

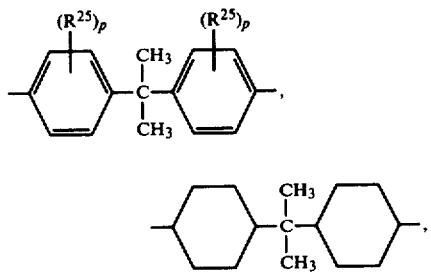

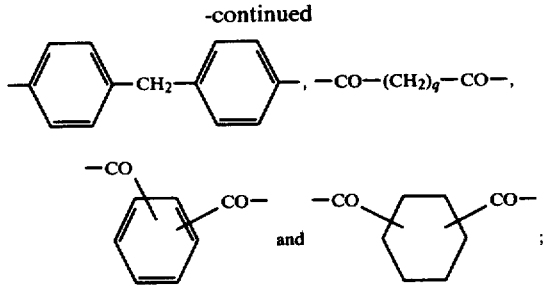

wherein:

p represents 0, 1 or 2;

$R^{25}$ represents a halogen atom; and q represents an integer of from 1 to 10; and Z represents any one of the groups defined for $R^2$;

when l=3:

Y represents one of the groups of formula

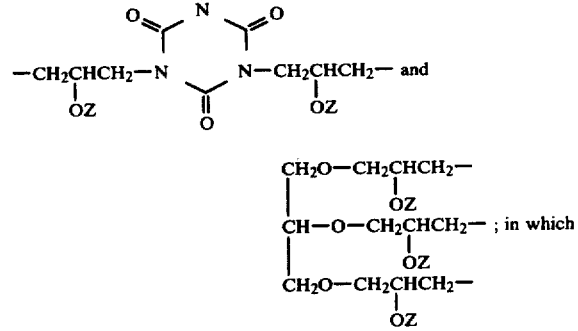

in which

Z is as defined above;

or an acid addition salt thereof.

2. A composition as claimed in claim 1, wherein the said polymer is a synthetic polymer.

3. A composition as claimed in claim 2, wherein the said synthetic polymer is an olefin polymer, a diene polymer, a styrene polymer or a polyurethane.

4. A composition as claimed in claim 1, wherein the said piperidine derivative or acid addition salt thereof is incorporated in an amount of from 0.01% to 5% by weight, based on the weight of the polymer.

* * * * *